(12) United States Patent
Pei et al.

(10) Patent No.: US 12,404,236 B2
(45) Date of Patent: Sep. 2, 2025

(54) NON-PEPTIDIC CELL-PENETRATING MOTIFS

(71) Applicant: Ohio State Innovation Foundation, Columbus, OH (US)

(72) Inventors: Dehua Pei, Columbus, OH (US); George Appiah Kubi, Columbus, OH (US); Ziqing Qian, Wellesley, MA (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 18/498,102

(22) Filed: Oct. 31, 2023

(65) Prior Publication Data
US 2024/0101509 A1    Mar. 28, 2024

Related U.S. Application Data

(63) Continuation of application No. 17/052,935, filed as application No. PCT/US2019/030915 on May 6, 2019, now Pat. No. 11,814,341.

(60) Provisional application No. 62/666,995, filed on May 4, 2018.

(51) Int. Cl.
| C07C 279/12 | (2006.01) |
| A61K 47/54 | (2017.01) |
| A61K 47/64 | (2017.01) |
| C07K 5/068 | (2006.01) |

(52) U.S. Cl.
CPC .......... *C07C 279/12* (2013.01); *A61K 47/542* (2017.08); *A61K 47/64* (2017.08); *C07K 5/06086* (2013.01)

(58) Field of Classification Search
None
See application file for complete search history.

(56) References Cited

U.S. PATENT DOCUMENTS

| 6,960,648 B2 | 11/2005 | Bonny |
| 7,862,807 B2 | 1/2011 | Goodman et al. |
| 8,623,833 B2 | 1/2014 | Rothbard et al. |
| 2002/0035243 A1 | 3/2002 | Imfeld et al. |
| 2002/0120100 A1 | 8/2002 | Bonny |
| 2003/0032594 A1 | 2/2003 | Bonny |
| 2019/0216752 A1 | 7/2019 | Im et al. |

FOREIGN PATENT DOCUMENTS

| EP | 1797901 | 6/2007 |
| WO | 2007071396 | 6/2007 |
| WO | 2017/083637 | 5/2017 |
| WO | 2018056530 | 3/2018 |

OTHER PUBLICATIONS

International Search Report and Written Opinion issued by the International Searching Authority (ISA/US) in PCT Application No. PCT/US2019/030915 on Jul. 15, 2019, 8 pages.

(Continued)

*Primary Examiner* — Renee Claytor
*Assistant Examiner* — Jennifer C Sawyer
(74) *Attorney, Agent, or Firm* — Meunier Carlin & Curfman LLC

(57) ABSTRACT

Disclosed are compounds that can penetrate the mitochondrial membrane and that are able to deliver cargo (e.g., therapeutic agents) specifically to the mitochondria.

16 Claims, 12 Drawing Sheets

(56) References Cited

OTHER PUBLICATIONS

International Preliminary Report on Patentability issued for Application No. PCT/US2019/030915, Nov. 19, 2020.
Extended European Search Report, issued May 18, 2022, received in connection with corresponding EP Patent Application No. 19796864.7.
Wu, Bo, et al. "Octa-guanidine morpholino restores dystrophin expression in cardiac and skeletal muscles and ameliorates pathology in dystrophic mdx mice." Molecular Therapy 17.5 (2009): 864-871.
Biswas, G., et al., "Synthesis of Ibuprofen Conjugated Molecular Transporter Capable of Enhanced Brain Penetration," Hindawi Journal of Chemistry, vol. 2017, Article ID 4746158, 2017, 10 pages.
Böttcher, Thomas, et al. "Synthesis and activity of biomimetic biofilm disruptors." Journal of the American Chemical Society 135.8 (2013): 2927-2930.
Calvo, Sarah E., and Vamsi K. Mootha. "The mitochondrial proteome and human disease." Annual review of genomics and human genetics 11 (2010): 25-44.
Cerrato, Carmine Pasquale, et al. "Novel cell-penetrating peptide targeting mitochondria." The FASEB Journal 29.11 (2015): 4589-4599.
Chinnery, P. F., et al. "Peptide nucleic acid delivery to human mitochondria." Gene therapy 6.12 (1999): 1919-1928.
Drysdale, Martin J., et al. "Targeting Hsp90 for the treatment of cancer." Current opinion in drug discovery & development 9.4 (2006): 483-495. Abstract.
Ernster, Lars, and Gottfried Schatz. "Mitochondria: a historical review." The Journal of cell biology 91.3 (1981): 227s-255s.
Fernández-Carneado, Jimena, et al. "Highly efficient, nonpeptidic oligoguanidinium vectors that selectively internalize into mitochondria." Journal of the American Chemical Society 127.3 (2005): 869-874.
Horton, Kristin L., et al. "Mitochondria-penetrating peptides." Chemistry & biology 15.4 (2008): 375-382.
Hoye, Adam T., et al. "Targeting mitochondria." Accounts of chemical research 41.1 (2008): 87-97.
Huang, Xinghua, et al. "Slipping synthesis of cucurbit [7] uril-based [2] rotaxane in organic environment." Tetrahedron Letters 53.47 (2012): 6414-6417.
Isidro-Llobet, Albert, Mercedes Alvarez, and Fernando Albericio. "Amino acid-protecting groups." Chemical reviews 109.6 (2009): 2455-2504.
Jean, Sae Rin, et al. "Peptide-mediated delivery of chemical probes and therapeutics to mitochondria." Accounts of chemical research 49.9 (2016): 1893-1902.
Kang, Byoung Heon, et al. "Combinatorial drug design targeting multiple cancer signaling networks controlled by mitochondrial Hsp90." The Journal of clinical investigation 119.3 (2009): 454-464.
Maiti, Kaustabh K., et al. "Guanidine-containing molecular transporters: sorbitol-based transporters show high intracellular selectivity toward mitochondria." Angewandte Chemie 119.31 (2007): 5984-5988.
Malty, Ramy H., et al. "Mitochondrial targets for pharmacological intervention in human disease." Journal of proteome research 14.1 (2015): 5-21.
Markovac, Anica, and Maurice P. LaMontagne. "Antimalarials. 12. Preparation of carbon isosteres of selected 4-pyridinemethanols as suppressive antimalarials." Journal of medicinal chemistry 23.11 (1980): 1198-1201.
Murphy, M. P. "Biochimica et Biophysica Acta Targeting lipophilic cations to mitochondria." Biochim. Biophys. Acta Bioenerg 1777 (2008): 1028-1031.
Pathak, Rakesh K., Nagesh Kolishetti, and Shanta Dhar. "Targeted nanoparticles in mitochondrial medicine." Wiley Interdisciplinary Reviews: Nanomedicine and Nanobiotechnology 7.3 (2015): 315-329.
Qian, Ziqing, et al. "Discovery and mechanism of highly efficient cyclic cell-penetrating peptides." Biochemistry 55.18 (2016): 2601-2612.
Qian, Ziqing, et al. "Early endosomal escape of a cyclic cell-penetrating peptide allows effective cytosolic cargo delivery." Biochemistry 53.24 (2014): 4034-4046.
Qian, Ziqing, et al. "Efficient delivery of cyclic peptides into mammalian cells with short sequence motifs." ACS chemical biology 8.2 (2013): 423-431.
Qian, Ziqing, Patrick G. Dougherty, and Dehua Pei. "Monitoring the cytosolic entry of cell-penetrating peptides using a pH-sensitive fluorophore." Chemical Communications 51.11 (2015): 2162-2165.
Stebbins, Charles E., et al. "Crystal structure of an Hsp90-geldanamycin complex: targeting of a protein chaperone by an antitumor agent." Cell 89.2 (1997): 239-250.
Toogood, Peter L. "Mitochondrial drugs." Current opinion in chemical biology 12.4 (2008): 457-463.
Weissig, V., G. G. M. D'Souza, and V. P. Torchilin. "DQAsome/DNA complexes release DNA upon contact with isolated mouse liver mitochondria." Journal of controlled release 75.3 (2001): 401-408.
Wipf, Peter, et al. "Mitochondrial targeting of selective electron scavengers: Synthesis and biological analysis of hemigramicidin—TEMPO conjugates." Journal of the American Chemical Society 127.36 (2005): 12460-12461.
Yamada, Yuma, and Hideyoshi Harashima. "Delivery of bioactive molecules to the mitochondrial genome using a membrane-fusing, liposome-based carrier, DF-MITO-Porter." Biomaterials 33.5 (2012): 1589-1595.
Zhao, Kesheng, et al. "Cell-permeable peptide antioxidants targeted to inner mitochondrial membrane inhibit mitochondrial swelling, oxidative cell death, and reperfusion injury." Journal of Biological Chemistry 279.33 (2004): 34682-34690.
Nair, Jyothi B., et al. "A Dual-Targeting Octaguanidine-Doxorubicin Conjugate Transporter for Inducing Caspase-Mediated Apoptosis on Folate-Expressing Cancer Cells." ChemMedChem 11.7 (2016): 702-712.
Supporting Information for : Nair, Jyothi B., et al. "A Dual-Targeting Octaguanidine-Doxorubicin Conjugate Transporter for Inducing Caspase-Mediated Apoptosis on Folate-Expressing Cancer Cells." ChemMedChem 11.7 (2016): 702-712.
STN abstract for Nair et al., 2016, 702-712.

(i)

(ii)

(iii)

FIG. 1B (con't)
(iv)
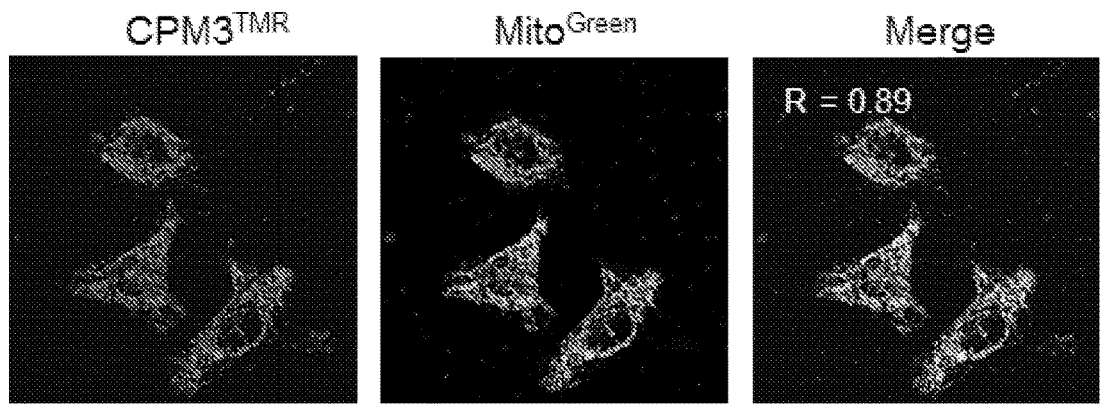
FIG. 2
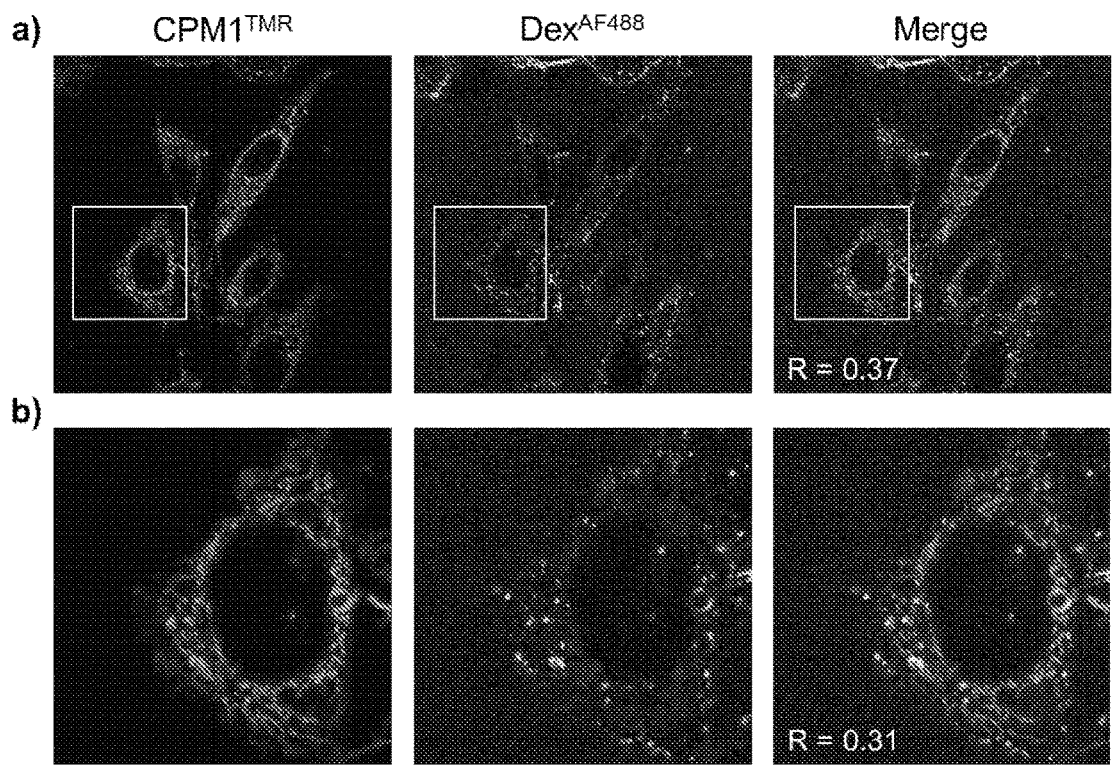

CPM1-TMR

CPM2-TMR

CPM-3-TMR

CPM4-TMR

A

B

NON-PEPTIDIC CELL-PENETRATING MOTIFS

CROSS-REFERENCE TO RELATED APPLICATIONS

This application claims the benefit of priority to U.S. Provisional Application No. 62/666,995, filed May 4, 2018, the entire contents of which are incorporated herein by reference in its entirety for all purposes.

STATEMENT REGARDING FEDERALLY FUNDED RESEARCH

This invention was made with government support under grant/contract numbers R01 GM110208 and R35 GM122459 awarded by the National Institutes of Health. The government has certain rights in the invention.

BACKGROUND

Mitochondria carry out a wide range of vital biochemical functions in eukaryotic cells including ATP production, calcium homeostasis, cell death, growth, differentiation, and catabolism and anabolism of secondary metabolites. Mitochondrial dysfunction is linked to many human diseases such as cardiovascular diseases (e.g., atherosclerosis, ischemia/reperfusion injury, heart failure, stroke), aging and neurodegenerative diseases (e.g., Alzheimer's disease, Parkinson's disease, Huntington's disease, amyotrophic lateral sclerosis, and Friedreich's ataxia), and metabolic diseases (e.g., diabetes and obesity). Therapeutic intervention of mitochondrial diseases is challenging, however, because a drug molecule must traverse the plasma as well as the two mitochondrial membranes before reaching the mitochondrial matrix. The problem is compounded by the fact that many therapeutic agents, such as peptides and nucleic acids, are not membrane-permeable.

Therefore, there exists a need in the art for compounds that are able to penetrate the mitochondrial membrane and compound that are able to deliver cargo (e.g., therapeutic agents) specifically to the mitochondria. The present disclosure addresses these needs.

SUMMARY

In some embodiments, the disclosure provides for compounds having a structure according to Formula I, or pharmaceutically acceptable salts or tautomers thereof:

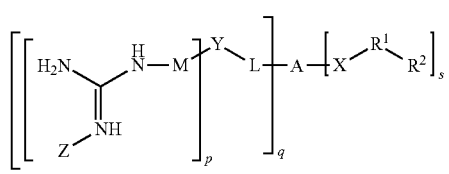

(I)

wherein:
A is a non-peptidic multivalent moiety;
each X is independently a first bonding group that links $R^1$ to A;
each Y is independently a bond or a second bonding group that links A to a guanidine or guanidinium group;
wherein guanidine or guanidinium group refers to the structure

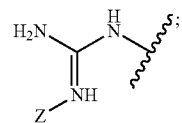

each Z is independently a lone pair, H, a halogen, CN, $NO_2$, $NH_2$, or alkyl;
each $R^1$ is independently a moiety comprising a hydrophobic residue;
each $R^2$ is independently absent or a moiety comprising a hydrophobic residue, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, each of which is optionally substituted, or $N^aR^b$, wherein $R^a$ and $R^b$ are independently selected from —H, alkyl, alkenyl, alkynyl, carbocyclyl, and heterocyclyl each of which are optionally substituted;
each L is independently a bond, or an alkylene, alkenylene, alkynylene, carbocyclyl, heterocyclyl, each of which are optionally substituted, or —$R^c$—$X^1$—$R^d$— wherein each of $R^c$ and $R^d$ are independently selected from alkylene, alkenylene, alkynylene, carbocyclyl, or heterocyclyl, each of which are optionally substituted, and $X^1$ is O, N, or S;
each M is independently a bond, or an alkylene, alkenylene, alkynylene, carbocyclyl, heterocyclyl, each of which are optionally substituted, or —$R^e$—$X^2$—$R^f$— wherein each of $R^e$ and $R^f$ are independently selected from alkylene, alkenylene, alkynylene, carbocyclyl, or heterocyclyl, each of which are optionally substituted, and $X^2$ is O, N, or S;
when L or Y, or both, is not a bond, p is an integer from 1 to 3, provided that when Y is an atom, the valence of Y is not violated;
q is an integer from 1 to 10;
when L and Y are each a bond, p is an integer from 1 to 10, and q is absent;
s is an integer from 1 to 3; and
optionally one or more cargo moieties, wherein at least one atom of Formula I is replaced by a cargo moiety or at least one lone pair in Formula I forms a bond to a cargo moiety.

In some embodiments, at least one atom of Formula I is replaced by a cargo moiety or at least one lone pair in Formula I forms a bond to a cargo moiety. In other embodiments, at least one cargo moiety is bonded to A. In yet other embodiments, at least one cargo moiety is bonded to $R^1$. In various embodiments, at least one cargo moiety is bonded to $R^2$.

In some embodiments of Formula I, at least one cargo moiety is bonded to A, $R^1$, or $R^2$ through a linker. In some embodiments, the linker comprises an amino acid, alkylene, alkenylene, alkynylene, carbocyclyl, heterocyclyl, or —$R^k$—$X^3$—$R^l$— wherein $R^k$ and $R^l$ are independently selected from alkylene, alkenylene, alkynylene, carbocyclyl, or heterocarbocyclyl, each of which are optionally substituted, and $X^3$ is O, N, or S In some embodiments, M is an alkylene.
In some embodiments, L is an alkylene.
In some embodiments of Formula I, A is a trivalent or tetravalent moiety. In some embodiments, A is a carbocyclyl, a heterocyclyl, an atom, or an amino acid. In some embodiments, A is an aryl or heteroaryl. In some embodiments, wherein A is nitrogen. In some embodiments, A is a nonpeptidic moiety comprising one or more residues of aspartic acid, glutamic acid, lysine or combinations thereof.

In some embodiments of Formula I, A is a non-polymeric multivalent moiety. In some embodiments, A is a pharmaceutically acceptable polymer moiety. In some embodiments, A is selected from carbohydrates, sugar alcohols, and polymeric alcohols. In some embodiments, A is a non-polymeric multivalent moiety. In certain embodiments, A is a non-polymeric alcohol. In certain embodiments, the non-polymeric alcohol is 2-hydroxy-1,3-propanediol, glycerol, thioglycerol, ethylene glycol.

In some embodiments, X comprises a bonding group selected from

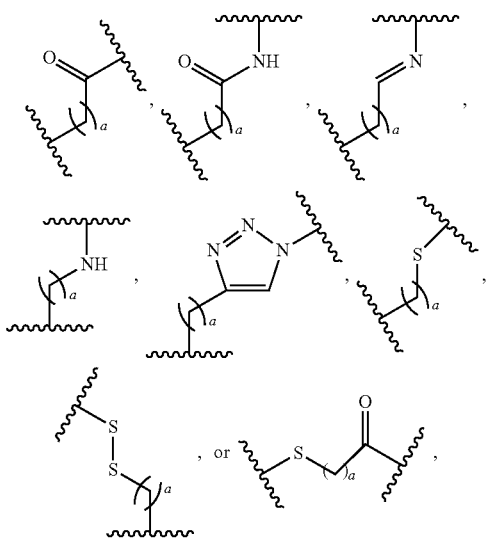

wherein each a is independently a number from 0 to 10.

In some embodiments, Y comprises a bonding group selected from N, S, —

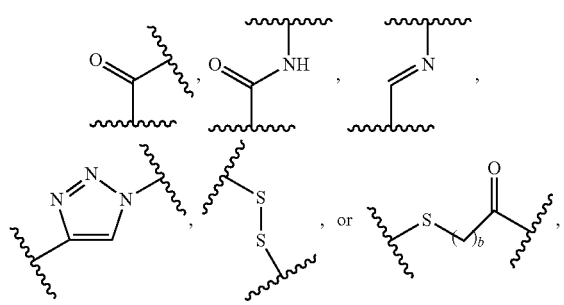

wherein each b is independently a number from 0 to 10.

In various embodiments, each $R^1$ independently comprises a hydrophobic residue selected from alkyl, alkenyl, alkynyl, carbocyclic, heterocyclic, aryl, or heteroaryl. In other embodiments, each $R^1$ is independently a hydrophobic residue comprising an aromatic ring. In some embodiments, $R^1$ comprises an amino acid residue, or analog thereof, having an aromatic side chain. In some embodiments, $R^1$ comprises an amino acid residue selected from the group consisting of phenylalanine, tryptophan, naphthylalanine, phenylglycine, homophenylalanine, tyrosine, cyclohexylglycine, piperidine-2-carboxylic acid, cyclohexylalanine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, and 3-(1,1'-biphenyl-4-yl)-alanine, each of which is optionally substituted with one or more substituents.

In various embodiments, each $R^2$ independently comprises a hydrophobic residue selected from alkyl, alkenyl, alkynyl, carbocyclic, heterocyclic, aryl, or heteroaryl. In other embodiments, each $R^2$ is independently a hydrophobic residue comprising an aromatic ring. In some embodiments, $R^2$ comprises an amino acid residue having a hydrophobic side chain. In some embodiments, the hydrophobic side chain is an aromatic side chain. In some embodiments, $R^2$ comprises an amino acid residue selected from the group consisting of phenylalanine, tryptophan, naphthylalanine, phenylglycine, homophenylalanine, tyrosine, cyclohexylglycine, piperidine-2-carboxylic acid, cyclohexylalanine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, and 3-(1,1'-biphenyl-4-yl)-alanine, each of which is optionally substituted with one or more substituents.

In some embodiments, p is 2 or 3.
In some embodiments, Y is N and p is 2.
In some embodiments, q is 2 or 3.
In some embodiments, s is 1.
In some embodiments, Z is H or a lone pair.

In some embodiments, of Formula I, when Y and L are each a bond, q is absent and the sum of p and s is an integer in the range of from 2 to 13. In some embodiments, the sum of p and s is an integer in the range of from 3 to 6. In other embodiments, the sum of p and s is 2. In yet other embodiments, the sum of p and s is 3. In still other embodiments, the sum of p and s is 4. In certain embodiments, the sum of p and s is 5. In other certain embodiments, the sum of p and s is 6. In still other certain embodiments, the sum of p and s is 7. In yet other certain embodiments, the sum of p and s is 8. In various embodiments, the sum of p and s is 9. In other various embodiments, the sum of p and s is 10. In still other various embodiments, the sum of p and s is 11. In yet other various embodiments, the sum of p and s is 12. In another embodiment, the sum of p and s is 13. In specific embodiments, the sum of p and s is an integer in the range of from 2 to 13, wherein s is 1. In other specific embodiments, the sum of p and s is an integer in the range of from 3 to 6, wherein s is 1

In some embodiments, of Formula I, when Y, L, or both is not a bond, the sum of q and s is an integer in the range of from 2 to 13. In some embodiments, the sum of q and s is an integer in the range of from 3 to 6. In other embodiments, the sum of q and s is 2. In yet other embodiments, the sum of q and s is 3. In still other embodiments, the sum of q and s is 4. In certain embodiments, the sum of q and s is 5. In other certain embodiments, the sum of q and s is 6. In still other certain embodiments, the sum of q and s is 7. In yet other certain embodiments, the sum of q and s is 8. In various embodiments, the sum of q and s is 9. In other various embodiments, the sum of q and s is 10. In still other various embodiments, the sum of q and s is 11. In yet other various embodiments, the sum of q and s is 12. In another embodiment, the sum of q and s is 13. In specific embodiments, the sum of q and s is an integer in the range of from 2 to 13, wherein s is 1. In other specific embodiments, the sum of q and s is an integer in the range of from 3 to 6, wherein s is 1.

In some embodiments of Formula I, the sum of p and s is an integer in the range of from 3 to 6. In other embodiments, the sum of p and s is 3 or 4.

In some embodiments of Formula I, the sum of q and s is an integer in the range of from 3 to 6. In other embodiments, the sum of q and s is 3 or 4.

In some embodiments, the present disclosure provides for compounds according to Formula II, or pharmaceutically acceptable salts or tautomers thereof:

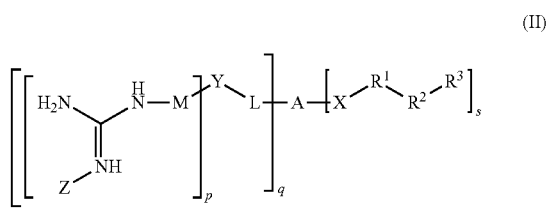

(II)

wherein
A is a non-peptidic multivalent moiety;
each X is independently a first bonding group that links $R^1$ to A;
each Y is independently a bond or a second bonding group that links A to a guanidine or guanidinium group; wherein
guanidine or guanidinium group refers to the structure

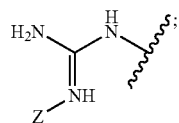

each Z is independently a lone pair, H, halogen, CN, $NO_2$, $NH_2$, or alkyl;
each $R^1$ is independently a moiety comprising a hydrophobic residue;
each $R^2$ is independently absent, a moiety comprising a hydrophobic residue, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, each of which is optionally substituted, or $NR^aR^b$, wherein $R^a$ and $R^b$ are independently selected from —H, alkyl, alkenyl, alkynyl, carbocyclyl, and heterocyclyl each of which are optionally substituted;
each $R^3$ is independently a cargo moiety, —H, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, each of which are optionally substituted, or $NR^iR^j$, wherein $R^i$ and $R^j$ are independently selected from —H, alkyl, alkenyl, alkynyl, carbocyclyl, and heterocyclyl each of which are optionally substituted;
each L is independently a bond, or an alkylene, alkenylene, alkynylene, carbocyclyl, heterocyclyl, each of which are optionally substituted, or —$R^c$—$X^1$—$R^d$— wherein each of $R^c$ and $R^d$ are independently selected from alkylene, alkenylene, alkynylene, carbocyclyl, or heterocyclyl, each of which are optionally substituted, and $X^1$ is O, N, or S;
each M is independently a bond, or an alkylene, alkenylene, alkynylene, carbocyclyl, heterocyclyl, each of which are optionally substituted, or —$R^e$—$X^2$—$R^f$— wherein each of $R^e$ and $R^f$ are independently selected from alkylene, alkenylene, alkynylene, carbocyclyl, or heterocyclyl, each of which are optionally substituted, and $X^2$ is O, N, or S;
when L or Y, or both, is not a bond, p is an integer from 1 to 3, provided that when Y is an atom, the valence of Y is not violated;
q is an integer from 1 to 10;
when L and Y are each a bond, p is an integer from 1 to 10, and q is absent; and
s is an integer from 1 to 3.

In some embodiments, M is an alkylene.
In some embodiments, L is an alkylene.
In some embodiments of Formula II, A is a trivalent or tetravalent moiety. In some embodiments, A is a carbocyclyl, a heterocyclyl, an atom, or an amino acid. In some embodiments, A is an aryl or heteroaryl. In some embodiments, wherein A is nitrogen. In some embodiments, A is a non-peptidic moiety comprising one or more residues of aspartic acid, glutamic acid, lysine or combinations thereof.

In some embodiments of Formula II, A is a non-polymeric multivalent moiety. In some embodiments, A is a pharmaceutically acceptable polymer moiety. In some embodiments, A is selected from carbohydrates, sugar alcohols, and polymeric alcohols. In some embodiments, A is a non-polymeric multivalent moiety. In certain embodiments, A is a non-polymeric alcohol. In certain embodiments, the non-polymeric alcohol is 2-hydroxy-1,3-propanediol, glycerol, thioglycerol, ethylene glycol.

In some embodiments, X comprises a bonding group selected from

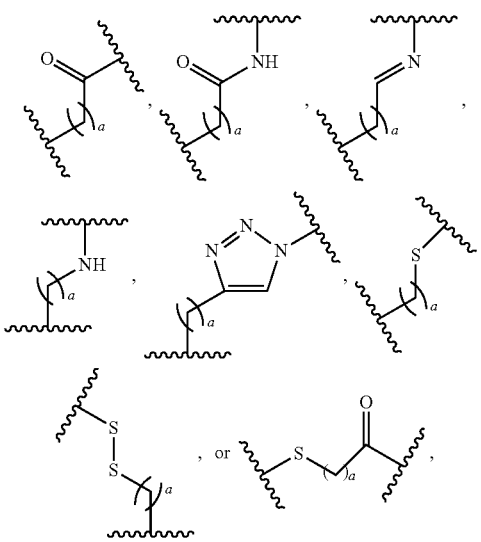

wherein each a is independently a number from 0 to 10.
In some embodiments, Y comprises a bonding group selected from N, S, —

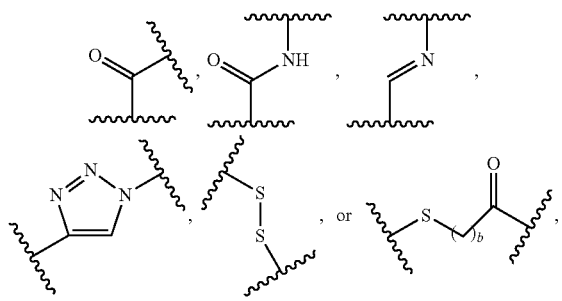

wherein each b is independently a number from 0 to 10.

In various embodiments, each $R^1$ independently comprises a hydrophobic residue selected from alkyl, alkenyl, alkynyl, carbocyclic, heterocyclic, aryl, or heteroaryl. In other embodiments, each $R^1$ is independently a hydrophobic residue comprising an aromatic ring. In some embodiments, $R^1$ comprises an amino acid residue, or analog thereof, having an aromatic side chain. In some embodiments, $R^1$ comprises an amino acid residue selected from the group consisting of phenylalanine, tryptophan, naphthylalanine, phenylglycine, homophenylalanine, tyrosine, cyclohexylglycine, piperidine-2-carboxylic acid, cyclohexylalanine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, and 3-(1,1'-biphenyl-4-yl)-alanine, each of which is optionally substituted with one or more substituents.

In various embodiments, each $R^2$ independently comprises a hydrophobic residue selected from alkyl, alkenyl, alkynyl, carbocyclic, heterocyclic, aryl, or heteroaryl. In other embodiments, each $R^2$ is independently a hydrophobic residue comprising an aromatic ring. In some embodiments, $R^2$ comprises an amino acid residue having a hydrophobic side chain. In some embodiments, the hydrophobic side chain is an aromatic side chain. In some embodiments, $R^2$ comprises an amino acid residue selected from the group consisting of phenylalanine, tryptophan, naphthylalanine, phenylglycine, homophenylalanine, tyrosine, cyclohexylglycine, piperidine-2-carboxylic acid, cyclohexylalanine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, and 3-(1,1'-biphenyl-4-yl)-alanine, each of which is optionally substituted with one or more substituents. When $R^2$ is an amino acid (or analog thereof), the termini not covalently bonded to $R^1$ may be protected with any suitable protecting groups, some of which are listed in $R^3$, or the cargo may be conjugated to said termini.

In some embodiments, p is 2 or 3.
In some embodiments, Y is N and p is 2.
In some embodiments, q is 2 or 3.
In some embodiments, s is 1.
In some embodiments, Z is H or a lone pair.
In some embodiments, of Formula II, when Y and L are each a bond, q is absent and the sum of p and s is an integer in the range of from 2 to 13. In some embodiments, the sum of p and s is an integer in the range of from 3 to 6. In other embodiments, the sum of p and s is 2. In yet other embodiments, the sum of p and s is 3. In still other embodiments, the sum of p and s is 4. In certain embodiments, the sum of p and s is 5. In other certain embodiments, the sum of p and s is 6. In still other certain embodiments, the sum of p and s is 7. In yet other certain embodiments, the sum of p and s is 8. In various embodiments, the sum of p and s is 9. In other various embodiments, the sum of p and s is 10. In still other various embodiments, the sum of p and s is 11. In yet other various embodiments, the sum of p and s is 12. In another embodiment, the sum of p and s is 13. In specific embodiments, the sum of p and s is an integer in the range of from 2 to 13, wherein s is 1. In other specific embodiments, the sum of p and s is an integer in the range of from 3 to 6, wherein s is 1

In some embodiments, of Formula II, when Y, L, or both is not a bond, the sum of q and s is an integer in the range of from 2 to 13. In some embodiments, the sum of q and s is an integer in the range of from 3 to 6. In other embodiments, the sum of q and s is 2. In yet other embodiments, the sum of q and s is 3. In still other embodiments, the sum of q and s is 4. In certain embodiments, the sum of q and s is 5. In other certain embodiments, the sum of q and s is 6. In still other certain embodiments, the sum of q and s is 7. In yet other certain embodiments, the sum of q and s is 8. In various embodiments, the sum of q and s is 9. In other various embodiments, the sum of q and s is 10. In still other various embodiments, the sum of q and s is 11. In yet other various embodiments, the sum of q and s is 12. In another embodiment, the sum of q and s is 13. In specific embodiments, the sum of q and s is an integer in the range of from 2 to 13, wherein s is 1. In other specific embodiments, the sum of q and s is an integer in the range of from 3 to 6, wherein s is 1.

In some embodiments of Formula II, the sum of p and s is an integer in the range of from 3 to 6. In other embodiments, the sum of p and s is 3 or 4.

In some embodiments of Formula II, the sum of q and s is an integer in the range of from 3 to 6. In other embodiments, the sum of q and s is 3 or 4.

In some embodiments, the compounds of Formula I have a structure according to Formula III, or pharmaceutically acceptable salts or tautomers thereof:

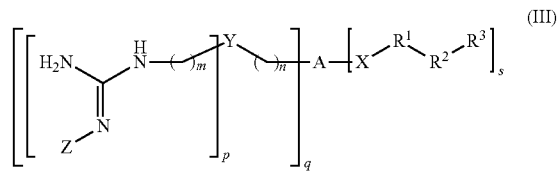

wherein:
A, X, Y, Z, $R^1$, p, q, and s are defined above;
each $R^2$ is independently a bond or a moiety comprising an aromatic ring;
each $R^3$ is independently a cargo moiety;
each m is independently an integer from 0 to 10; and
each n is independently an integer from 0 to 6.
In some embodiments, n is 1, 2, or 3.
In other embodiments, m is 3, 4, 5, 6, or 7.
In some embodiments, p is 2 or 3.
In certain embodiments, Y is N and p is 2.
In certain other embodiments, q is 2 or 3.
In specific embodiments, s is 1.
In some embodiments, the compounds of Formula I and/or II have a structure according to Formula IV, or pharmaceutically acceptable salts or tautomers thereof:

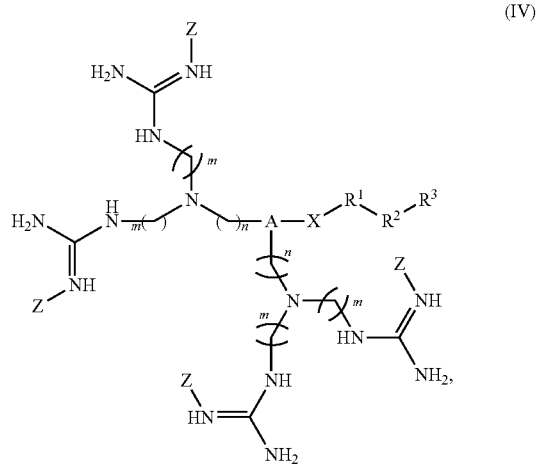

wherein:
A, X, Z, $R^1$, $R^2$, $R^3$, m and n are defined above.
In some embodiments, A is aryl, heteroaryl, or nitrogen.
In particular embodiments, the compounds of the present disclosure (e.g., the compounds according to Formula I, II, III, or IV) have one of the following structures:

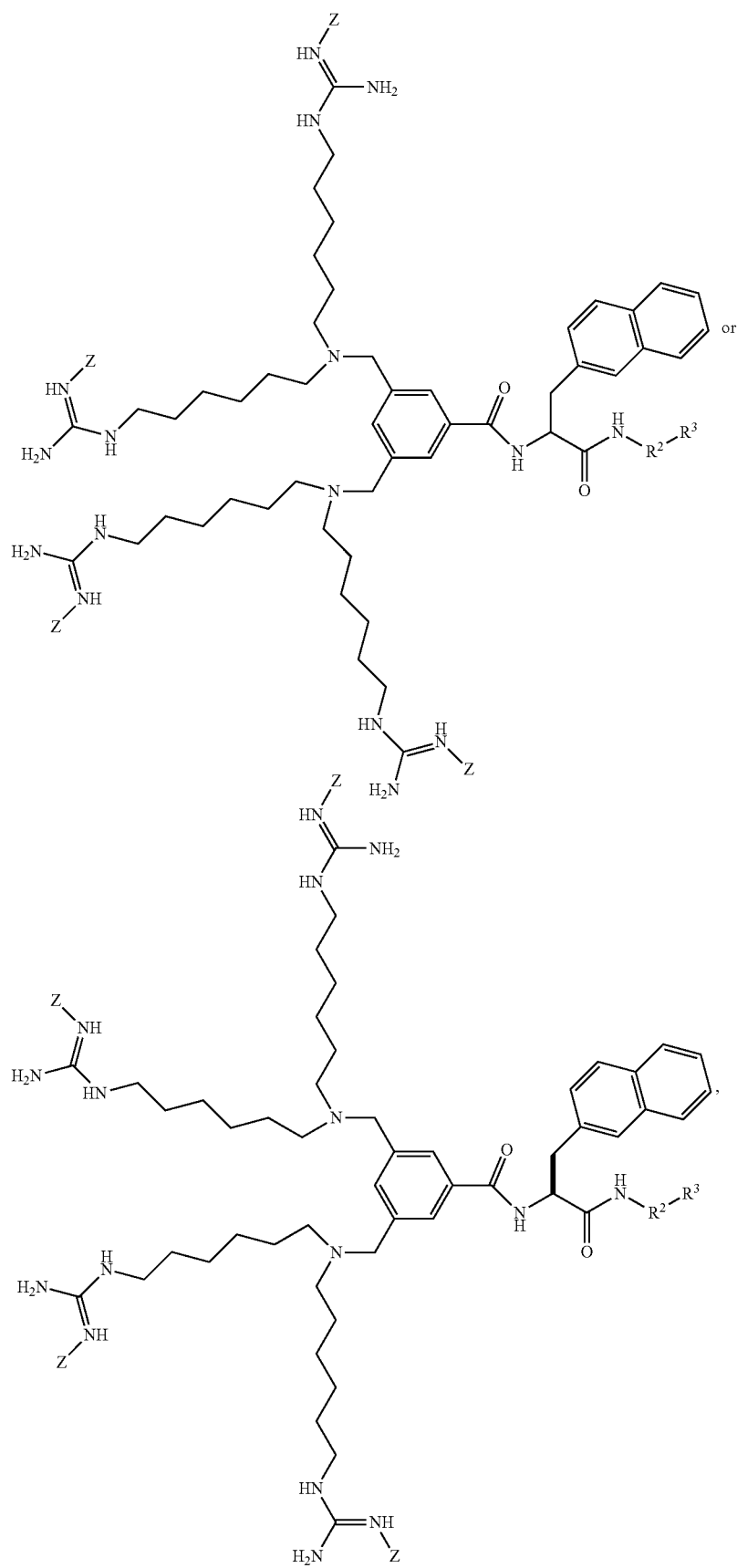
or pharmaceutically acceptable salts or tautomers thereof.

In some embodiments, the compounds of the present disclosure (e.g., the compounds of Formula I, II, III, or IV) have one of the following structures:

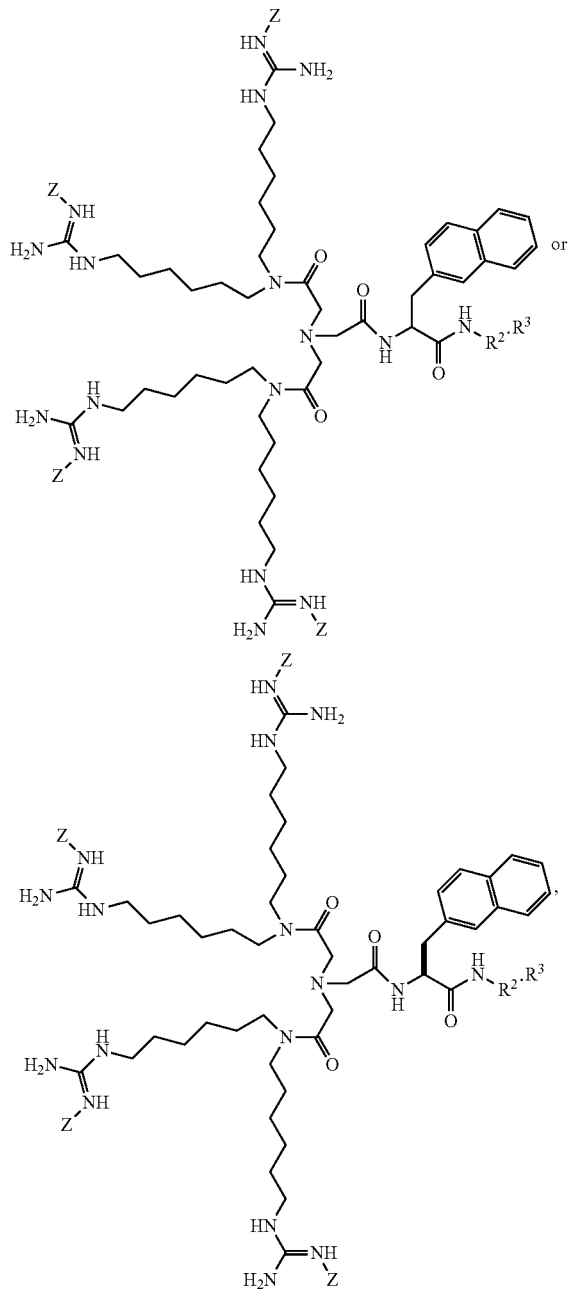

or pharmaceutically acceptable salts or tautomers thereof.

In various embodiments of the present disclosure, the cargo moiety comprises a therapeutic agent.

In various embodiments, a pharmaceutical composition comprising a compound of the present disclosure is provided.

In various embodiments, the present disclosure provides for methods of delivering a therapeutic agent to the mitochondria of cell, comprising contacting the cell with a compound or pharmaceutical composition disclosed herein.

In some embodiments, the present disclosure provides for methods of treating a disease, comprising administering a compound or pharmaceutical composition disclosed herein.

BRIEF DESCRIPTION OF FIGURES

FIG. 2 shows the lack of co-localization between CPM1$^{TMR}$ and endosomal marker, AlexaFluor488-labeled dextrin (Dex$^{AF488}$). HeLa cells were treated with 2 μM CPM1$^{TMR}$ and Dex$^{AF488}$ for 2 h and then imaged by confocal microscopy without fixation. Panel b) shows the expansion of the boxed areas in a). R values represent Pearson's correlation coefficients, which indicate the degree of co-localization between the TMR and AlexaFluor488 signals.

DETAILED DESCRIPTION

Definitions

Figure 1A:
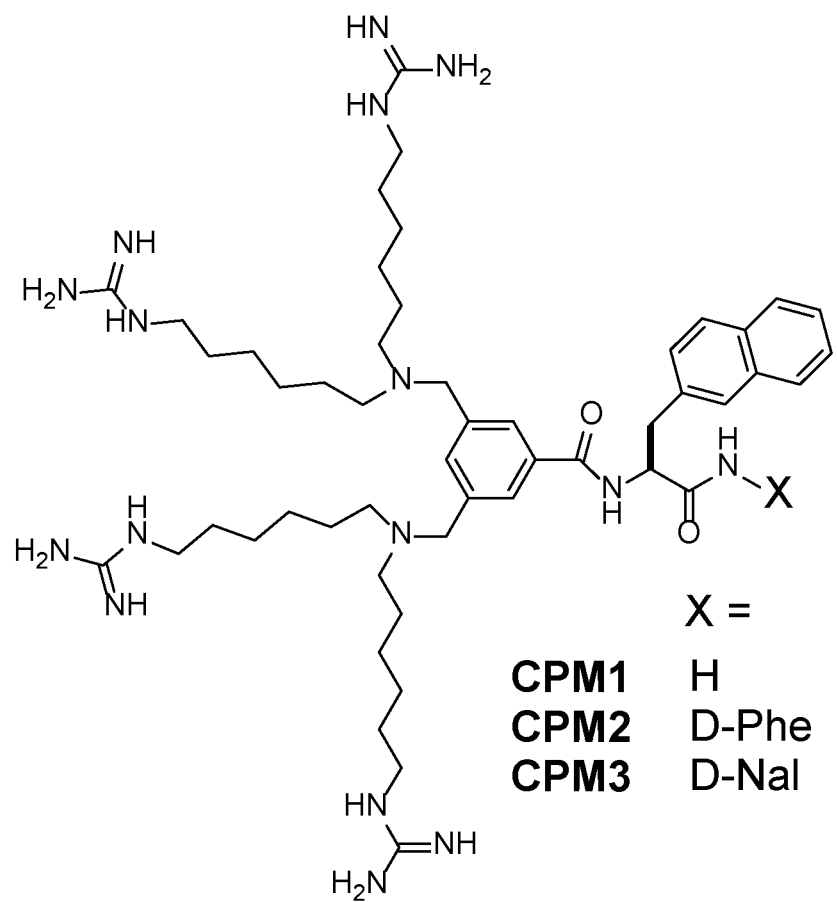
FIG. 1A shows the chemical structures of cell-penetrating motifs (CPMs) 1-3. CPM2 and CPM3 incorporated the hydrophobic amino acids D-phenylalanine (D-Phe) and D-naphthylalanine (D-Nal), respectively.

"Alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. Unless stated otherwise specifically in the specification, an alkylene chain can be optionally substituted as described herein.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. Unless stated otherwise specifically in the specification, an alkenylene chain can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain, having from two to forty carbon atoms, and having one or more carbon-carbon triple bonds. Non-limiting examples of $C_2$-$C_{40}$ alkynylene include ethynylene, propargylene and the like. Unless stated otherwise specifically in the specification, an alkynylene chain can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Unless stated otherwise specifically in the specification, the carbocyclyl can be a monocyclic, bicyclic, tricyclic or tetracyclic ring system, which can include fused or bridged ring systems Carbocyclic rings include aryls and cycloalkyl, cycloalkenyl, and cycloalkynyl as defined herein. In some embodiments, the carbocyclyl is monovalent and is attached to the result of molecule through a single bond. In some embodiments, the carbocyclyl is divalent and is independently attached to two moieties through single bonds. Unless stated otherwise specifically in the specification, a carbocyclyl group can be optionally substituted.

"Cycloalkyl" refers to a stable non-aromatic monocyclic or polycyclic fully saturated hydrocarbon having from 3 to 40 carbon atoms and at least one ring, wherein the ring consists solely of carbon and hydrogen atoms, which can include fused or bridged ring systems. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. In some embodiments, the cycloalkyl is monovalent and is attached to the result of molecule through a single bond. In some embodiments, the cycloalkyl is divalent and is independently attached to two moieties through single bonds. Unless otherwise stated specifically in the specification, a cycloalkyl group can be optionally substituted.

"Cycloalkenyl" refers to a stable non-aromatic monocyclic or polycyclic hydrocarbon having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyls include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. In some embodiments, cycloalkenyl is divalent and is attached, directly or indirectly, to the CPP through a single bond and, directly or indirectly, through a single bond. In some embodiments, the cycloalkenyl is monovalent and is attached to the result of molecule through a single bond. In some embodiments, the cycloalkenyl is divalent and is independently attached to two moieties through single bonds. Unless otherwise stated specifically in the specification, a cycloalkenyl group can be optionally substituted.

"Cycloalkynyl" refers to a stable non-aromatic monocyclic or polycyclic hydrocarbon having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyls include, for example, cycloheptynyl, cyclooctynyl, and the like. In some embodiments, the cycloalkynyl is monovalent and is attached to the result of molecule through a single bond. In some embodiments, the cycloalkynyl is divalent and is independently attached to two moieties through single bonds. Unless otherwise stated specifically in the specification, a cycloalkynyl group can be optionally substituted.

"Aryl" refers to a hydrocarbon ring system comprising hydrogen, 6 to 40 carbon atoms and at least one aromatic ring. For purposes of this disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is monovalent and is attached to the result of molecule through a single bond. In some embodiments, the aryl is divalent and is independently attached to two moieties through single bonds. Unless stated otherwise specifically in the specification, an aryl group can be optionally substituted.

"Heterocyclyl," "heterocyclic ring" or "heterocycle" refers to a stable 3- to 22-membered ring system which consists of two to fourteen carbon atoms and from one to eight heteroatoms selected from the group consisting of nitrogen, oxygen and sulfur. Heterocyclyl or heterocyclic rings include heteroaryls as defined below. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl is monovalent and is attached to the rest of the molecule through a single bond. In some embodiments, the heterocyclyl is divalent and is independently attached to two moieties single bonds. Unless stated otherwise specifically in the specification, a heterocyclyl group can be optionally substituted.

"Heteroaryl" refers to a 5- to 22-membered aromatic ring comprising hydrogen atoms, one to fourteen carbon atoms, one to eight heteroatoms selected from the group consisting of nitrogen, oxygen and sulfur, and at least one aromatic ring. For purposes of this disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). In some embodiments, the heteroaryl is monovalent and is attached to the result of molecule through a single bond. In some embodiments, the heteroaryl is divalent and is independently attached to two moieties through single bonds. Unless stated otherwise specifically in the specification, a heteroaryl group can be optionally substituted.

The term "substituted" used herein means any of the above groups (i.e., alkylene, alkenylene, alkynylene, aryl, carbocyclyl, cycloalkyl, cycloalkenyl, cycloalkynyl, heterocyclyl, heteroaryl, and/or ether) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =SO$_2$R$_g$, and —SO$_2$NR$_g$R$_h$. "Substituted" also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more hydrogen atoms on any of the above groups are replaced by a substituent listed in this paragraph, and the substituent then forms a covalent bond with the CPM or cargo moiety.

As used herein, "bonding group" refers to a multivalent moiety that covalently bonds at least two components of the CPM (e.g., the multifunctional moiety A to the moiety comprising an aromatic residue or to a guanidine and/or a guanidinium group). In some embodiments, the bonding group can be cyclic (e.g., triazole) or acyclic (e.g., amide or amine) moiety. The bonding group can be coupled to the rest of the molecule in any suitable arrangement. In some embodiments, the bonding group is divalent, trivalent, or tetravalent.

Multivalent refers to a moiety that has several cites at which attachment can occur. As used herein, "multivalent moiety" refers to a moiety comprising two or more sites at which A, X, Y, L, M, guanidine or guanidinium groups, and/or cargo can be attached. The multivalent moiety can have 2, 3, 4, 5, 6, 7, 8, 9, 10, 11, 12, or 13 sites of attachment. At each site of attachment, a lone pair, hydrogen atom, leaving group (e.g., halogen, hydroxy, —OTS, —OMs, —ONs, —OTf, alkoxy, —OSO$_2$R, etc.) or other suitable moiety can be substituted by any of the aforementioned options. In some embodiments, the multivalent moiety is divalent, trivalent, or tetravalent. Multivalent and multifunctional may be used interchangeably. Similarly, trivalent and trifunctional can be used interchangeably, as can tetrafunctional and trifunctional.

As used herein, the symbol

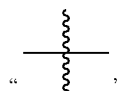

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

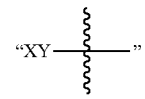

indicates that the chemical entity "XY" is bonded to another chemical entity via the point of attachment bond, but the other chemical entity is not depicted. Furthermore, the specific point of attachment to the non-depicted chemical entity can be specified by inference. For example, the compound CH$_3$—R$^3$, wherein R$^3$ is H or

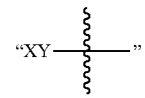

infers that when the point of attachment bond is the same bond as the bond by which R$^3$ is depicted as being bonded to CH$_3$.

A residue of a chemical species, as used herein, refers to a derivative of a moiety that is present in a particular product. For example, in some embodiments, an aromatic residue in a component may refer to one or more —(C$_6$H$_5$)$_n$ units present in a component. Similarly, an amino acid residue refers to a component with part of an amino acid incorporated therein, and such residues may be referred to herein interchangeably as an amino acid or an amino acid residue. For example, a residue of naphthylalanine is represented by the following structure:

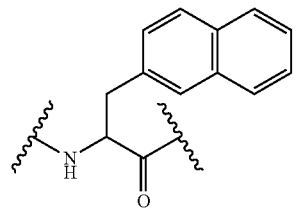 [SMILES: *NC(Cc1ccc2ccccc2c1)C(*)=O]

As used herein, the term "non-peptidic" refers to a moiety having not more than two amino acids linked in sequence by a peptide bond. To put it another way, "non-peptidic" can refer to a moiety that has no amino acids (e.g., an aromatic ring), a moiety comprising one amino acod, or a moiety comprising two amino acids. But, "non-peptidic" does not encompass a moiety comprising three or more amno acids linked sequence, such as Arg-Arg-Nal.

As used herein, an "analog" of an amino acid refers to a compound that is structurally similar but not identical to an amino acid. For example, an analog of napthylalanine encompasses compounds in which side chain is elongated by one or more hydrocarbon groups.

As used herein the terms "treating" or "treatment" includes prevention; delay in onset; diminution, eradication, or delay in exacerbation of signs or symptoms after onset;

prevention of relapse; and ameliorating one or more conditions associated with a disease or illness disclosed herein.

As used herein, "therapeutically effective" refers to an amount of CPM which confers a therapeutic effect on a patient. In some embodiments, the therapeutically effective amount is an amount sufficient to treat a disease, including, but not limited to a mitochondrial disease.

Compounds

Disclosed herein are compounds comprising a cell penetrating motif (CPM). A "cell penetrating motif" or "CPM" refers to any motif which is capable of penetrating a cell membrane. In some embodiments, the cell penetrating motif penetrates the cell membrane and localizes in the cytosol. In other embodiments, after cytosolic entry, the CPM is also capable of localizing in subcellular structures such as the mitochondria. The CPMs described herein comprise guanidine or guanidinium groups of arginines and hydrophobic groups, such as the aromatic rings of naphthylalanine, and these groups were found to facilitate cellular uptake. In some embodiments, the CPM have 2 or more guanidine and/or guanidinium groups (e.g., 2, 3, 5, 6, 7, 8, 9, 10 or more), and one or more hydrophobic groups (e.g., 1, 2, 3, 5, 6, 7, 8, 9, 10 or more). Further, any hydrogen on the CPM can be replaced by a bond to a cargo moiety to provide for intracellular (e.g., mitochondrial) delivery of the cargo moiety.

In some embodiments, the CPMs comprise a plurality of guanidine and/or guanidinium groups (2 or more, e.g., 3, 4, 5, 6, 7, 8, 9, 10 or more) anchored to a scaffold (e.g., an aromatic ring, such as a benzene ring). In some embodiments, a hydrophobic group (e.g., an aromatic hydrophobic amino acid including, but not limited to, naphthylalanine (Nal)) can be appended to the scaffold to render the CPM amphipathic, a feature that can facilitate cytosolic entry. Advantageously, cargo can be attached at any suitable position and delivered to the intracellular space of the cell, including the mitochondria. In some embodiments, to enable cargo attachment and minimize any potential mutual interference between CPM and the cargo, a flexible linker, e.g., miniPEG-Lys, is added to a carboxyl group of a hydrophobic residue (see Examples in FIGS. 4 and 6-8).

In some embodiments, the disclosure provides for a compound having a structure according to Formula I, or pharmaceutically acceptable salts or tautomers thereof:

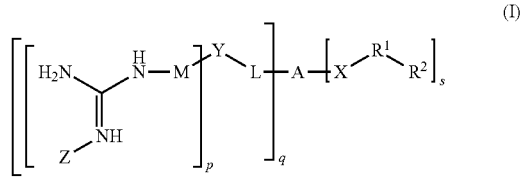

(I)

wherein:

A is a non-peptidic multivalent moiety;

each X is independently a first bonding group that links $R^1$ to A;

each Y is independently a bond or a second bonding group that directly or indirectly links A to a guanidine or guanidinium group; wherein guanidine or guanidinium group refers to the structure

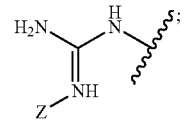

each Z is independently a lone pair, H, halogen, CN, $NO_2$, $NH_2$, or alkyl (when Z is a lone pair, said group is referred to as a guanidine group; when Z is halogen, CN, $NO_2$, $NH_2$, or alkyl, said group is referred to as a guanidinium group);

each $R^1$ is independently a moiety comprising a hydrophobic residue;

each $R^2$ is independently absent, a moiety comprising a hydrophobic residue, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, each of which is optionally substituted, or $NR^aR^b$, wherein $R^a$ and $R^b$ are independently selected from —H, alkyl, alkenyl, alkynyl, carbocyclyl, and heterocyclyl each of which are optionally substituted;

each L is independently a bond, or an alkylene, alkenylene, alkynylene, carbocyclyl, heterocyclyl, each of which are optionally substituted, or —$R^c$—$X^1$—$R^d$— wherein each of $R^c$ and $R^d$ are independently selected from alkylene, alkenylene, alkynylene, carbocyclyl, or heterocyclyl, each of which are optionally substituted, and $X^1$ is O, N, or S;

each M is independently a bond, or an alkylene, alkenylene, alkynylene, carbocyclyl, heterocyclyl, each of which are optionally substituted, or —$R^e$—$X^2$—$R^f$— wherein each of $R^e$ and $R^f$ are independently selected from alkylene, alkenylene, alkynylene, carbocyclyl, or heterocyclyl, each of which are optionally substituted, and $X^2$ is O, N, or S;

when L or Y, or both, is not a bond (i.e., when L or Y, or both, are any of the groups described herein other than a bond), p is an integer from 1 to 3, provided that when Y is an atom, the valence of Y is not violated;

q is an integer from 1 to 10;

when L and Y are each a bond, p is an integer from 1 to 10, and q is absent;

s is an integer from 1 to 3; and optionally one or more cargo moieties, wherein at least one atom of Formula I is replaced by a cargo moiety or at least one lone pair in Formula I forms a bond to a cargo moiety.

In some embodiments, the compound of Formula I optionally comprises one or more cargo moieties, wherein a hydrogen atom or lone pair is replaced by a cargo moiety. In some embodiments, at least one cargo moiety is bonded to A. In some embodiments, at least one cargo moiety is bonded to $R^1$. In some embodiments, at least one cargo moiety is bonded to $R^2$.

In some embodiments, the cargo moiety is bonded to A, $R^1$, or $R^2$ through a linker. In some embodiments, the linker comprises an amino acid, alkylene, alkenylene, alkynylene, carbocyclyl, heterocyclyl, or —$R^k$—$X^3$—$R^l$— wherein $R^k$ and $R^l$ are independently selected from alkylene, alkenylene, alkynylene, carbocyclyl, or heterocarbocyclyl, each of which are optionally substituted, and $X^3$ is O, N, or S.

In some embodiments, A is a multivalent moiety. In some embodiments, A is a trivalent or tetravalent moiety. In some embodiments, A is an alkyl, a carbocyclyl, a heterocyclyl, an atom, or an amino acid. In some embodiments, A is an aryl or heteroaryl. In some embodiments, wherein A is nitrogen. In some embodiments, A is a non-peptidic moiety comprising one or more residues of aspartic acid, glutamic acid, lysine or combinations thereof.

The connectivity of the multivalent moiety A within a compound of Formula I can vary depending on the nature of the L, Y, and M groups specified. Thus, in various aspects of the present disclosure, the multivalent moiety A can be directly bonded to either L, Y, M or a guanidine/guanidinium group. In some embodiments, when L is present as a group other than a bond, the multivalent moiety A is directly bonded to L in a compound of Formula I. In other embodiments, when L is a bond and Y is a second bonding group, A is directly bonded to Y in a compound of Formula I. Under conditions where L or Y, or both is not a bond, the valence of A is determined by the sum of q and s. In still other embodiments, a compound of Formula I is provided where Y and L, but not M, are each a bond, such that A is necessarily directly bonded to one or more M moieties. In yet other embodiments, each of Y, L, and M is defined as a bond, such that A is necessarily directly bonded to one or more guanidine and/or guanidinium moieties. Under conditions where at least Y and L are each a bond, the valence of A is determined by the sum of p and s.

In some embodiments, the compounds disclosed herein can be prepared by the appropriate substitution of one or more —OH groups on a precursor (e.g., $A(OH)_n$) to form one or more corresponding moieties bonded to A. Non-limiting examples of suitable compounds of formula $A(OH)_n$ include 2-hydroxy-1,3-propanediol, glycerol, thioglycerol, ethylene glycol, polyethylene glycol, polyvinylalcohol, other pharmaceutically acceptable polymers, and the like. Other examples of $A(OH)_n$ include carbohydrates, sugar alcohols, polymeric alcohols, and the like. Still other examples of $A(OH)_n$ include polysaccharides such as cellulose or starch, or modified forms thereof (e.g., esters and/or ethers thereof). In one embodiment, when A is derived from glycerol, the hydrogen on two of the three OH groups on glycerol may be substituted with a bis(guanidinoalkyl)amine, via formation of carbamate bonding groups, and the hydrogen on the third OH group may be substituted with an amino acid of a short peptide, via formation of a carbamate bonding group.

Non-limiting examples of sugar alcohols include mannitol, sorbitol, xylitol, maltitol, arabitol, ribitol, dulcitol, iditol, isomalt, lactitol, erythritol, and the like. Non-limiting examples of carbohydrates include monosaccharides, disaccharides, oligosaccharides, polysaccharides, celluloses, modified cellulosics, starches, and the like. Further examples of carbohydrates include 5- and 6-membered ring monosaccharides such as ribose, furanose, and mannose, disaccharides such lactose, sucrose, maltose, agrose, polysaccharides and oligosaccharides such as dextrins and maltodextrins, and modified cellulosics such as microcrystalline cellulose, silicified microcrystalline cellulose, mannitol-microcrystalline cellulose, hydroxypropylcellulose, L-hydroxypropylcellulose (low substituted), low molecular weight hydroxypropyl methylcellulose (HPMC) (e.g. Methocel E, F and K from Dow Chemical, Metolose SH from Shin-Etsu, Ltd), hydroxyethylcellulose, sodium carboxymethylcellulose, carboxymethyl hydroxyethylcellulose and other cellulose derivatives.

As noted above, multivalent moiety A has multiple sites of attachment. In some embodiments, the percentage of sites occupied relative to the total available cites of attachment is in the range of from about 10% to about 100%, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges therebetween.

In some embodiments of Formula I, A is a non-polymeric multivalent moiety. In some embodiments, A is a pharmaceutically acceptable polymer moiety. In some embodiments, A is selected from carbohydrates, sugar alcohols, and polymeric alcohols. In some embodiments, A is a non-polymeric multivalent moiety. In certain embodiments, A is a non-polymeric alcohol. In certain embodiments, the non-polymeric alcohol is 2-hydroxy-1,3-propanediol, glycerol, thioglycerol, ethylene glycol.

In some embodiments, each X is independently a first bonding group that links $R^1$ to A. In various embodiments, X comprises a bonding group selected from:

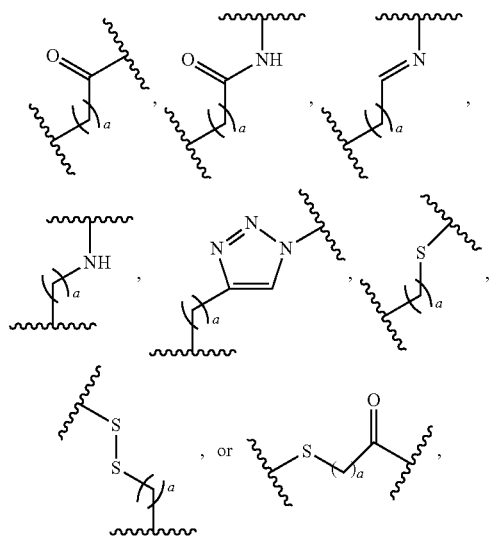

wherein each a is independently number from 0 to 10, e.g., 0, 1, 2, 3, 4, 5, 6, 7, 8, 9, and 10, inclusive of all values and subranges therebetween. In specific embodiments, X is

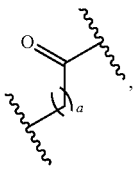

wherein a is 0. In other specific embodiments, X is

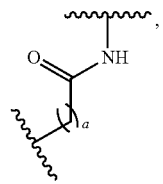

wherein a is 0.

In some embodiments, each Y is independently absent or a second bonding group that directly or indirectly links A to a guanidine or guanidinium group. In some embodiments, Y is selected from:

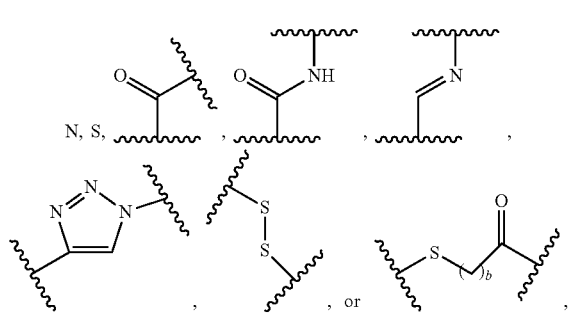

wherein each b is independently a number from 0 to 10, e.g., 0, 1, 2, 3, 4, 5, 6, 7, 8, 9, and 10, inclusive of all values and subranges therebetween. In certain embodiments, Y is absent. In other embodiments, Y is N.

In some embodiments, each $R^1$ independently comprises a hydrophobic residue selected from alkyl, alkenyl, alkynyl, carbocyclic, heterocyclic, aryl, or heteroaryl. In some embodiments, $R^1$ is a residue of an amino acid which has a hydrophobic side chain. In various embodiments of $R^1$, the residue comprises a non-aromatic hydrophobic amino acid. In certain embodiments, each non-aromatic hydrophobic amino acid is independently selected from glycine, alanine, valine, leucine, isoleucine, methionine, proline, cyclohexylalanine, piperidine-2-carboxylic acid, or norleucine, each of which is optionally substituted with one or more substituents. In other embodiments, each $R^1$ is independently a hydrophobic residue comprising an aromatic ring. In various embodiments, each $R^1$ is independently a moiety comprising a hydrophobic aromatic residue. In some embodiments, each $R^1$ is a moiety comprising a hydrophobic aromatic ring. $R^1$ can include one or more aromatic rings, including fused rings. In some embodiments, the hydrophobic residue in $R^2$ has a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the hydrophobic residue in $R^2$ has a SASA SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$, at least about 350 Å$^2$, at least about 360 Å$^2$, at least about 370 Å$^2$, at least about 380 Å$^2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, $R^1$ is an amino acid residue, or analog thereof, having an aromatic side chain. In certain embodiments of $R^1$, the aromatic hydrophobic amino acid is naphthylalanine, phenylglycine, homophenylalanine, phenylalanine, tryptophan, or tyrosine, each of which is optionally substituted with one or more substituents. In certain embodiments, $R^1$ is an amino acid selected from the group consisting of phenylalanine, tryptophan, naphthylalanine, phenylglycine, homophenylalanine, tyrosine, cyclohexylalanine, piperidine-2-carboxylic acid, cyclohexylglycine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, and 3-(1,1'-biphenyl-4-yl)-alanine, each of which is optionally substituted with one or more substituents. In specific embodiments, $R^1$ is naphthylalanine, which is optionally substituted. In other specific embodiments, $R^1$ is phenylalanine, which is optionally substituted. When $R^1$ is an amino acid (or analog thereof), the cargo may be conjugated to the termini of $R^1$ (either the N- or C-termini of $R^1$ depending on how $R^1$ is coupled to A) or the termini may be protected with any suitable protecting groups, some of which are listed in $R^2$.

In various embodiments, each $R^2$ is independently absent, a moiety comprising a hydrophobic residue, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, or $NR^aR^b$, wherein $R^a$ and $R^b$ are independently selected from —H, alkyl, alkenyl, alkynyl, carbocyclyl, and heterocyclyl each of which are optionally substituted. When $R^2$ is absent, $R^1$ is terminated with an appropriate atom. For example $R^2$ is absent and $R^1$ is an amino acid residue, the amino acid reside may be terminated with H, or it may have a protecting group, such as an alkyl (Suitable amino acid-protecting groups are described in Isidro-Albert et al. "Amino Acid-Protecting Groups" Chem. Rev. 2009, 6, 2455-2504, which is herein incorporated by reference in its entirety). In various other embodiments, each $R^2$ independently comprises a hydrophobic residue selected from alkyl, alkenyl, alkynyl, carbocyclic, heterocyclic, aryl, or heteroaryl. In some embodiments, $R^2$ is a residue of an amino acid which has a hydrophobic side chain. In various embodiments of $R^2$, the residue comprises a non-aromatic hydrophobic amino acid. In certain embodiments, each hydrophobic amino acid is independently selected from glycine, alanine, valine, leucine, isoleucine, methionine, proline, cyclohexylalanine, piperidine-2-carboxylic acid, or norleucine, each of which is optionally substituted with one or more substituents. When $R^2$ is an amino acid (or analog thereof), the termini not covalently bonded to $R^1$ may be protected with any suitable protecting groups, some of which are listed in $R^3$, or the cargo may be conjugated to said termini.

In other embodiments, each $R^2$ is independently a hydrophobic residue comprising an aromatic ring. In some embodiments, the hydrophobic residue comprising an aromatic ring is an amino acid having a hydrophobic side chain. Non-limiting examples of aromatic hydrophobic amino acids include naphthylalanine, phenylglycine, homophenylalanine, phenylalanine, tryptophan, or tyrosine, each of which is optionally substituted with one or more substituents. In some embodiments, each $R^2$ is a moiety comprising a hydrophobic aromatic ring. $R^2$ can include one or more aromatic rings, including fused rings. In some embodiments, the hydrophobic residue in $R^2$ has a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the hydrophobic residue in $R^2$ has a SASA SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$, at least about 350 Å$^2$, at least about 360 Å$^2$, at least about 370 Å$^2$, at least about 380 Å$^2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$.

In some embodiments, R$^2$ is a residue of an amino acid which has a hydrophobic side chain. In certain embodiments, R$^2$ is an amino acid selected from the group consisting of phenylalanine, tryptophan, naphthylalanine, phenylglycine, homophenylalanine, tyrosine, cyclohexylalanine, piperidine-2-carboxylic acid, cyclohexylglyine, 3-(3-benzothienyl)-alanine, 3-(2-quinolyl)-alanine, O-benzylserine, 3-(4-(benzyloxy)phenyl)-alanine, S-(4-methylbenzyl) cysteine, N-(naphthalen-2-yl)glutamine, and 3-(1,1'-biphenyl-4-yl)-alanine, each of which is optionally substituted with one or more substituents. In specific embodiments, R$^2$ is naphthylalanine, which is optionally substituted. In other specific embodiments, R$^2$ is phenylalanine, which is optionally substituted.

In various embodiments, each L is independently a bond, or an alkylene, alkenylene, alkynylene, carbocyclyl, heterocyclyl, or —R$^c$—X$^1$—R$^d$— wherein each of R$^c$ and R$^d$ are independently selected from alkylene, alkenylene, alkynylene, carbocyclyl, or heterocyclyl, each of which are optionally substituted, and X$^1$ is O, N, or S. In some embodiments, L is an alkylene.

In various embodiments, each M is independently a bond, or an alkylene, alkenylene, alkynylene, carbocyclyl, heterocyclyl, or —R$^e$—X$^2$—R$^f$— wherein each of R$^e$ and R$^f$ are independently selected from alkylene, alkenylene, alkynylene, carbocyclyl, or heterocyclyl, each of which are optionally substituted, and X$^2$ is O, N, or S. In some embodiments, M is an alkylene.

In various embodiments, p is an integer from 1 to 3, provided that when Y is an atom, the valence of Y is not violated. In some embodiments, when L or Y, or both, is not a bond, p is an integer from 1 to 3, provided that when Y is an atom, the valence of Y is not violated. In some embodiments p is 2 or 3. In certain embodiments, p is 2. In certain other embodiments, p is 3.

In some embodiments, q is an integer from 1 to 10, e.g., 1, 2, 3, 4, 5, 6, 7, 8, 9, and 10, inclusive of all values and subranges therebetween. In certain embodiments, q is 2 or 3. In specific embodiments, q is 2. In other embodiments, when L and Y are each a bond, p is an integer from 1 to 10, and q is absent In some embodiments, s is an integer from 1 to 3. In specific embodiments, s is 1.

In some embodiments, of Formula I, when Y and L are each a bond, q is absent and the sum of p and s is an integer in the range of from 2 to 13, e.g., 2, 3, 4, 5, 6, 7, 8, 9, 10, 11, 12, and 13, inclusive of all values and subranges therebetween. In some embodiments, the sum of p and s is an integer of from 3 to 6. In other embodiments, the sum of p and s is 2. In yet other embodiments, the sum of p and s is 3. In still other embodiments, the sum of p and s is 4. In certain embodiments, the sum of p and s is 5. In other certain embodiments, the sum of p and s is 6. In still other certain embodiments, the sum of p and s is 7. In yet other certain embodiments, the sum of p and s is 8. In various embodiments, the sum of p and s is 9. In other various embodiments, the sum of p and s is 10. In still other various embodiments, the sum of p and s is 11. In yet other various embodiments, the sum of p and s is 12. In another embodiment, the sum of p and s is 13. In specific embodiments, the sum of p and s is an integer in the range of from 2 to 13, wherein s is 1. In other specific embodiments, the sum of p and s is an integer in the range of from 3 to 6, wherein s is 1

In some embodiments, of Formula I, when Y, L, or both is not a bond, the sum of q and s is an integer in the range of from 2 to 13. In some embodiments, the sum of q and s is an integer of from 3 to 6. In other embodiments, the sum of q and s is 2. In yet other embodiments, the sum of q and s is 3. In still other embodiments, the sum of q and s is 4. In certain embodiments, the sum of q and s is 5. In other certain embodiments, the sum of q and s is 6. In still other certain embodiments, the sum of q and s is 7. In yet other certain embodiments, the sum of q and s is 8. In various embodiments, the sum of q and s is 9. In other various embodiments, the sum of q and s is 10. In still other various embodiments, the sum of q and s is 11. In yet other various embodiments, the sum of q and s is 12. In another embodiment, the sum of q and s is 13. In specific embodiments, the sum of q and s is an integer in the range of from 2 to 13, wherein s is 1. In other specific embodiments, the sum of q and s is an integer in the range of from 3 to 6, wherein s is 1.

In some embodiments of Formula I, the sum of p and s is an integer in the range of from 3 to 6. In other embodiments, the sum of p and s is 3 or 4.

In some embodiments of Formula I, the sum of q and s is an integer in the range of from 3 to 6. In other embodiments, the sum of q and s is 3 or 4.

In some embodiments of Formula I, Z is H, halogen, CN, NO$_2$, NH$_2$, or alkyl. As noted above, when Z is H, halogen, CN, NO$_2$, NH$_2$, or alkyl, the compounds of Formula I comprise a guanidinium group defined by

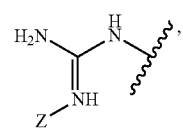

which has a positive charge. Therefore, in some embodiments, the charged compounds of Formula I further comprise a counterion (i.e., an anion) that includes, but is not limited to halide (e.g., chloride, bromide, or iodide), phosphate, hydrogen phosphate, dihydrogen phosphate, sulfate, hydrogen sulfate, acetate, formate, trifluoroacetate, mesylate, besylate, oxalate, fumarate, lactate, maleate, malonate, citrate, and hexafluorophosphate.

In some embodiments, the present disclosure provides for compounds according to Formula II, or pharmaceutically acceptable salts or tautomers thereof:

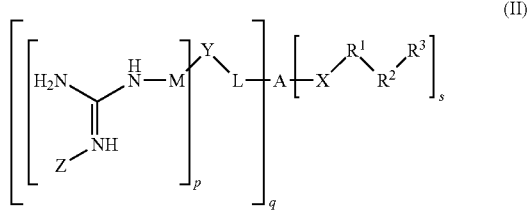
(II)

wherein:
A is a non-peptidic multivalent moiety;
each X is independently a first bonding group that links $R^1$ to A;
each Y is independently a bond or a second bonding group that directly or indirectly links A to a guanidine or guanidinium group; wherein

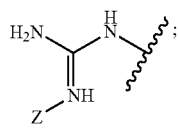

guanidine or guanidinium group refers to the structure
each Z is independently a lone pair, H, halogen, CN, $NO_2$, $NH_2$, or alkyl;
each $R^1$ is independently a moiety comprising a hydrophobic residue;
each $R^2$ is independently absent, a moiety comprising a hydrophobic residue, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, each of which is optionally substituted, or $NR^aR^b$, wherein $R^a$ and $R^b$ are independently selected from —H, alkyl, alkenyl, alkynyl, carbocyclyl, and heterocyclyl each of which are optionally substituted;
each $R^3$ is independently a cargo moiety, —H, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, each of which are optionally substituted, or $NR^iR^j$, wherein $R^i$ and $R^j$ are independently selected from —H, alkyl, alkenyl, alkynyl, carbocyclyl, and heterocyclyl each of which are optionally substituted;
each L is independently a bond, or an alkylene, alkenylene, alkynylene, carbocyclyl, heterocyclyl, each of which are optionally substituted, or —$R^c$—$X^1$—$R^d$— wherein each of $R^c$ and $R^d$ are independently selected from alkylene, alkenylene, alkynylene, carbocyclyl, or heterocyclyl, each of which are optionally substituted, and $X^1$ is O, N, or S;
each M is independently a bond, or an alkylene, alkenylene, alkynylene, carbocyclyl, heterocyclyl, each of which are optionally substituted, or —$R^e$—$X^2$—$R^f$— wherein each of $R^e$ and $R^f$ are independently selected from alkylene, alkenylene, alkynylene, carbocyclyl, or heterocyclyl, each of which are optionally substituted, and $X^2$ is O, N, or S;
when L or Y, or both, is not a bond, p is an integer from 1 to 3, provided that when Y is an atom, the valence of Y is not violated;
q is an integer from 1 to 10;
when L and Y are each a bond, p is an integer from 1 to 10, and q is absent; and
s is an integer from 1 to 3.

In various embodiments, A is a multivalent moiety. In some embodiments, A is a trivalent or tetravalent moiety. In other embodiments, A is an alkyl, a carbocyclyl, a heterocyclyl, an atom, or an amino acid. In still other embodiments, A is an aryl, heteroaryl, or nitrogen. In yet other embodiments, A is an aryl or heteroaryl. In some embodiments, the aryl or heteroaryl is selected from phenyl, naphthyl, phenanthryl, pyridyl, pyrimidyl, triazinyl, quinolinyl, isoquinolinyl, indolinyl, benzoxazolyl, and benzothiazolyl. In further embodiments, A is nitrogen. In various other embodiments, A is a non-peptidic moiety comprising one or more residues of aspartic acid, glutamic acid, lysine or combinations thereof.

The connectivity of the multivalent moiety A within a compound of Formula II can vary depending on the nature of the L, Y, and M groups specified. Thus, in various aspects of the present disclosure, the multivalent moiety A can be bonded to either L, Y, M or a guanidine/guanidinium group. In some embodiments, when L is present as a group other than a bond, the multivalent moiety A is directly bonded to L in a compound of Formula II. In other embodiments, when L is a bond and Y is a second bonding group, A is directly bonded to Y in a compound of Formula II. Under conditions where L or Y, or both is not a bond, the valence of A is determined by the sum of q and s. In still other embodiments, a compound of Formula II is provided where Y and L, but not M, are each a bond, such that A is necessarily directly bonded to one or more M moieties. In yet other embodiments, each of Y, L, and M is defined as a bond, such that A is necessarily directly bonded to one or more guanidine and/or guanidinium moieties. Under conditions where at least Y and L are each a bond, the valence of A is determined by the sum of p and s.

In some embodiments of Formula II, A is a non-polymeric multivalent moiety. In some embodiments, A is a pharmaceutically acceptable polymer moiety. In some embodiments, A is selected from carbohydrates, sugar alcohols, and polymeric alcohols. In some embodiments, A is a non-polymeric multivalent moiety. In certain embodiments, A is a non-polymeric alcohol. In certain embodiments, the non-polymeric alcohol is 2-hydroxy-1,3-propanediol, glycerol, thioglycerol, ethylene glycol.

In some embodiments, each X is independently a first bonding group that links $R^1$ to A. In various embodiments, X comprises a bonding group selected from:

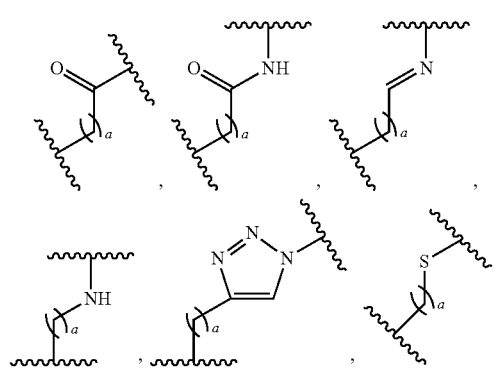

-continued

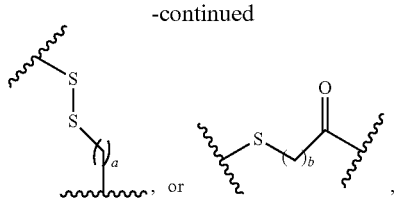

wherein each a is independently number from 0 to 10, e.g., 0, 1, 2, 3, 4, 5, 6, 7, 8, 9, and 10, inclusive of all values and subranges therebetween. In specific embodiments, X is

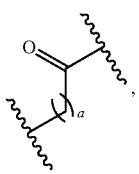

wherein a is 0. In other specific embodiments, X is

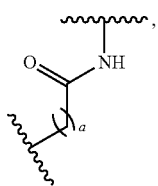

wherein a is 0.

In some embodiments, each Y is independently a bond or a second bonding group that directly or indirectly links A to a guanidine or guanidinium group. In some embodiments, Y is selected from:

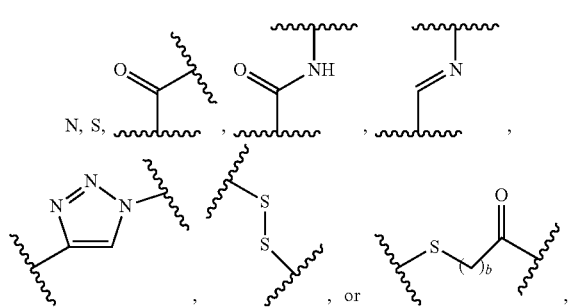

wherein each b is independently a number from 0 to 10, e.g., 0, 1, 2, 3, 4, 5, 6, 7, 8, 9, and 10, inclusive of all values and subranges therebetween. In certain embodiments, Y is absent. In other embodiments, Y is N.

In some embodiments, each $R^1$ independently comprises a hydrophobic residue selected from alkyl, alkenyl, alkynyl, carbocyclic, heterocyclic, aryl, or heteroaryl. In some embodiments, $R^1$ is a residue of an amino acid which has a hydrophobic side chain. In various embodiments of $R^1$, the residue comprises a non-aromatic hydrophobic amino acid. In certain embodiments, each non-aromatic hydrophobic amino acid is independently selected from glycine, alanine, valine, leucine, isoleucine, methionine, proline, cyclohexylalanine, piperidine-2-carboxylic acid, or norleucine, each of which is optionally substituted with one or more substituents. In other embodiments, each $R^1$ is independently a hydrophobic residue comprising an aromatic ring. In various embodiments, each $R^1$ is independently a moiety comprising a hydrophobic aromatic residue. In some embodiments, $R^1$ is an amino acid residue, or analog thereof, having an aromatic side chain. In certain embodiments of $R^1$, the aromatic hydrophobic amino acid is naphthylalanine, phenylglycine, homophenylalanine, phenylalanine, tryptophan, or tyrosine, each of which is optionally substituted with one or more substituents. In certain embodiments, $R^1$ is an amino acid selected from the group consisting of phenylalanine, tryptophan, naphthylalanine, phenylglycine, homophenylalanine, tyrosine, cyclohexylalanine, piperidine-2-carboxylic acid, cyclohexylglycine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, and 3-(1,1'-biphenyl-4-yl)-alanine, each of which is optionally substituted with one or more substituents. In specific embodiments, $R^1$ is naphthylalanine, which is optionally substituted. In other specific embodiments, $R^1$ is phenylalanine, which is optionally substituted. When $R^1$ is an amino acid (or analog thereof), the cargo may be conjugated to the termini of $R^1$ (either the N- or C-termini of $R^1$ depending on how $R^1$ is coupled to A) or the termini may be protected with any suitable protecting groups, some of which are listed in $R^2$.

In some embodiments, each $R^1$ is a moiety comprising a hydrophobic aromatic ring. $R^1$ can include one or more aromatic rings, including fused rings. In some embodiments, the hydrophobic residue in $R^1$ has a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the hydrophobic residue in $R^2$ has a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$, at least about 350 Å$^2$, at least about 360 Å$^2$, at least about 370 Å$^2$, at least about 380 Å$^2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$.

In various embodiments, each $R^2$ is independently absent, a moiety comprising a hydrophobic residue, alkyl, alkenyl, alkynyl, carbocyclyl, heterocyclyl, —C(O)alkyl, —C(O)alkenyl, —C(O)alkynyl, —C(O)-carbocyclyl, —C(O)-heterocyclyl, or $NR^aR^b$, wherein $R^a$ and $R^b$ are independently selected from —H, alkyl, alkenyl, alkynyl, carbocyclyl, and heterocyclyl each of which are optionally substituted. In various other embodiments, each $R^2$ independently comprises a hydrophobic residue selected from alkyl, alkenyl, alkynyl, carbocyclic, heterocyclic, aryl, or heteroaryl. In some embodiments, $R^2$ is a residue of an amino acid which has a hydrophobic side chain. In various embodiments of $R^2$, the residue comprises a non-aromatic hydrophobic amino acid. In certain embodiments, each hydrophobic amino acid is independently selected from glycine, alanine, valine, leucine, isoleucine, methionine, proline, cyclohexylalanine, piperidine-2-carboxylic acid, or norleucine, each of which is optionally substituted with one or more substituents. In other embodiments, each $R^2$ is independently a hydrophobic residue which comprises an aromatic ring. In some embodiments, the hydrophobic residue comprising an aromatic ring is an amino acid having an aromatic side chain. Non-limiting examples of such amino acids include an amino acid selected from the group consisting of phenylalanine, tryptophan, naphthylalanine, phenylglycine, homophenylalanine, tyrosine, cyclohexylalanine, piperidine-2-carboxylic acid, cyclohexylglycine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, and 3-(1,1'-biphenyl-4-yl)-alanine, each of which is optionally substituted with one or more substituents. In specific embodiments, $R^2$ is naphthylalanine, which is optionally substituted. In other specific embodiments, $R^2$ is phenylalanine, which is optionally substituted. When $R^2$ is an amino acid (or analog thereof), the termini not covalently bonded to $R^1$ may be protected with any suitable protecting groups, some of which are listed in $R^3$, or the cargo may be conjugated to said termini.

In some embodiments, each $R^2$ is a moiety comprising a hydrophobic aromatic ring. $R^2$ can include one or more aromatic rings, including fused rings. In some embodiments, the hydrophobic residue in $R^2$ has a SASA of at least about 200 $Å^2$, at least about 210 $Å^2$, at least about 220 $Å^2$, at least about 240 $Å^2$, at least about 250 $Å^2$, at least about 260 $Å^2$, at least about 270 $Å^2$, at least about 280 $Å^2$, at least about 290 $Å^2$, at least about 300 $Å^2$, at least about 310 $Å^2$, at least about 320 $Å^2$, or at least about 330 $Å^2$. In some embodiments, the hydrophobic residue in $R^2$ has a SASA of at least about 200 $Å^2$, at least about 210 $Å^2$, at least about 220 $Å^2$, at least about 240 $Å^2$, at least about 250 $Å^2$, at least about 260 $Å^2$, at least about 270 $Å^2$, at least about 280 $Å^2$, at least about 290 $Å^2$, at least about 300 $Å^2$, at least about 310 $Å^2$, at least about 320 $Å^2$, or at least about 330 $Å^2$, at least about 350 $Å^2$, at least about 360 $Å^2$, at least about 370 $Å^2$, at least about 380 $Å^2$, at least about 390 $Å^2$, at least about 400 $Å^2$, at least about 410 $Å^2$, at least about 420 $Å^2$, at least about 430 $Å^2$, at least about 440 $Å^2$, at least about 450 $Å^2$, at least about 460 $Å^2$, at least about 470 $Å^2$, at least about 480 $Å^2$, at least about 490 $Å^2$, greater than about 500 $Å^2$, at least about 510 $Å^2$, at least about 520 $Å^2$, at least about 530 $Å^2$, at least about 540 $Å^2$, at least about 550 $Å^2$, at least about 560 $Å^2$, at least about 570 $Å^2$, at least about 580 $Å^2$, at least about 590 $Å^2$, at least about 600 $Å^2$, at least about 610 $Å^2$, at least about 620 $Å^2$, at least about 630 $Å^2$, at least about 640 $Å^2$, greater than about 650 $Å^2$, at least about 660 $Å^2$, at least about 670 $Å^2$, at least about 680 $Å^2$, at least about 690 $Å^2$, or at least about 700 $Å^2$.

In various embodiments, each $R^3$ is independently a cargo moiety, carbocyclyl, heterocyclyl, —H, alkyl, alkenyl, alkynyl, —C(O)alkyl, —C(O)alkenyl, —C(O)alkynyl, —C(O)-carbocyclyl, —C(O)-heterocyclyl, or $NR^iR^j$, wherein $R^i$ and $R^j$ are independently selected from —H, alkyl, alkenyl, alkynyl, carbocyclyl, and heterocyclyl each of which are optionally substituted.

In various embodiments, each L is independently a bond, or an alkylene, alkenylene, alkynylene, carbocyclyl, heterocyclyl, or —$R^c$—$X^1$—$R^d$— wherein each of $R^c$ and $R^d$ are independently selected from alkylene, alkenylene, alkynylene, carbocyclyl, or heterocyclyl, each of which are optionally substituted, and $X^1$ is O, N, or S. In some embodiments, L is an alkylene.

In various embodiments, each M is independently a bond, or an alkylene, alkenylene, alkynylene, carbocyclyl, heterocyclyl, or —$R^e$—$X^2$—$R^f$— wherein each of $R^e$ and $R^f$ are independently selected from alkylene, alkenylene, alkynylene, carbocyclyl, or heterocyclyl, each of which are optionally substituted, and $X^2$ is O, N, or S. In some embodiments, M is an alkylene.

In various embodiments, p is an integer from 1 to 3, provided that when Y is an atom, the valence of Y is not violated. In other embodiments, when L or Y, or both, is not a bond, p is an integer from 1 to 3, provided that when Y is an atom, the valence of Y is not violated In some embodiments p is 2 or 3. In certain embodiments, p is 2. In certain other embodiments, p is 3.

In some embodiments, q is an integer from 1 to 10, e.g., 1, 2, 3, 4, 5, 6, 7, 8, 9, and 10, inclusive of all values and subranges therebetween. In certain embodiments, q is 2 or 3. In specific embodiments, q is 2. In other embodiments, when L and Y are each a bond, p is an integer from 1 to 10, and q is absent.

In some embodiments, s is an integer from 1 to 3. In specific embodiments, s is 1.

In some embodiments, of Formula II, when Y and L are each a bond, q is absent and the sum of p and s is an integer in the range of from 2 to 13, e.g., 2, 3, 4, 5, 6, 7, 8, 9, 10, 11, 12, and 13, inclusive of all values and subranges therebetween. In some embodiments, the sum of p and s is an integer in the range of from 3 to 6. In other embodiments, the sum of p and s is 2. In yet other embodiments, the sum of p and s is 3. In still other embodiments, the sum of p and s is 4. In certain embodiments, the sum of p and s is 5. In other certain embodiments, the sum of p and s is 6. In still other certain embodiments, the sum of p and s is 7. In yet other certain embodiments, the sum of p and s is 8. In various embodiments, the sum of p and s is 9. In other various embodiments, the sum of p and s is 10. In still other various embodiments, the sum of p and s is 11. In yet other various embodiments, the sum of p and s is 12. In another embodiment, the sum of p and s is 13. In specific embodiments, the sum of p and s is an integer in the range of from 2 to 13, wherein s is 1. In other specific embodiments, the sum of p and s is an integer in the range of from 3 to 6, wherein s is 1

In some embodiments, of Formula II, when Y, L, or both is not a bond, the sum of q and s is an integer in the range of from 2 to 13, e.g., 2, 3, 4, 5, 6, 7, 8, 9, 10, 11, 12, and 13, inclusive of all values and subranges therebetween. In some embodiments, the sum of q and s is an integer in the range of from 3 to 6. In other embodiments, the sum of q and s is 2. In yet other embodiments, the sum of q and s is 3. In still other embodiments, the sum of q and s is 4. In certain embodiments, the sum of q and s is 5. In other certain embodiments, the sum of q and s is 6. In still other certain embodiments, the sum of q and s is 7. In yet other certain embodiments, the sum of q and s is 8. In various embodiments, the sum of q and s is 9. In other various embodiments, the sum of q and s is 10. In still other various embodiments, the sum of q and s is 11. In yet other various embodiments, the sum of q and s is 12. In another embodiment, the sum of q and s is 13. In specific embodiments, the sum of q and s is an integer in the range of from 2 to 13, wherein s is 1. In other specific embodiments, the sum of q and s is an integer in the range of from 3 to 6, wherein s is 1.

In some embodiments of Formula II, the sum of p and s is an integer in the range of from 3 to 6. In other embodiments, the sum of p and s is 3 or 4.

In some embodiments of Formula II, the sum of q and s is an integer in the range of from 3 to 6. In other embodiments, the sum of q and s is 3 or 4.

In various embodiments, the present disclosure provides for compounds having a structure according to Formula III or pharmaceutically acceptable salts or tautomers thereof:

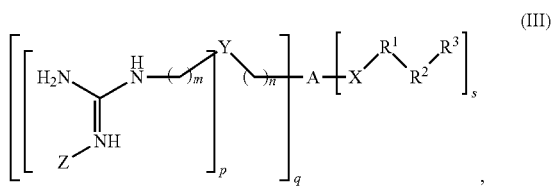

(III)

wherein A, X, Y, Z, $R^1$, $R^2$, $R^3$, p, q, and s are as defined above.

In some embodiments, each m is independently an integer from 0 to 10, e.g., 0, 1, 2, 3, 4, 5, 6, 7, 8, 9, and 10, inclusive of all values and subranges therebetween. In other embodiments, each m is independently 4, 5, 6, 7, or 8. In other embodiments, m is 3, 4, 5, 6, or 7. In specific embodiments, m is 6. In other specific embodiments, m is 7. In certain other embodiments, m is 5.

In some embodiments, each n is independently an integer from 0 to 6, e.g., 0, 1, 2, 3, 4, 5, 6, inclusive of all values and subranges therebetween. In other embodiments, each n is independently 1, 2, or 3. In specific embodiments, n is 1. In other specific embodiments, n is 2.

In certain embodiments, Y is N, m is 6, and n is 1. In certain embodiments, Y is N, m is 5, and n is 1. In certain embodiments, Y is N, m is 7, and n is 1.

In certain embodiments, Y is N and p is 2. In certain other embodiments, Y is N, p is 2, and s is 1.

In certain embodiments, Y is N, p is 2, and q is 2. In certain other embodiments, Y is N, p is 2, q is 2, and s is 1.

In various embodiments, the present disclosure provides a structure according to Formula IV or pharmaceutically acceptable salts or tautomers thereof:

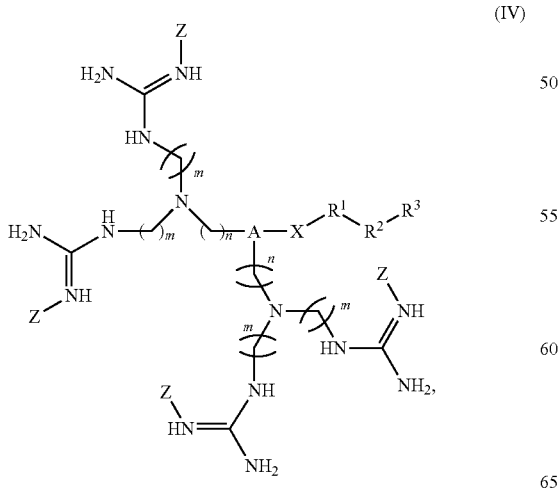

(IV)

where A, X, Z, $R^1$, $R^2$, $R^3$, m, and n are as defined above.

In various embodiments of Formula IV, A is a trivalent or tetravalent moiety. In some embodiments, A is a carbocyclyl, heterocyclyl, an atom, or an amino acid.

In various embodiments, the compound of Formula IV is a compound of Formula IV-A to IV-C or pharmaceutically acceptable salt or tautomer thereof:

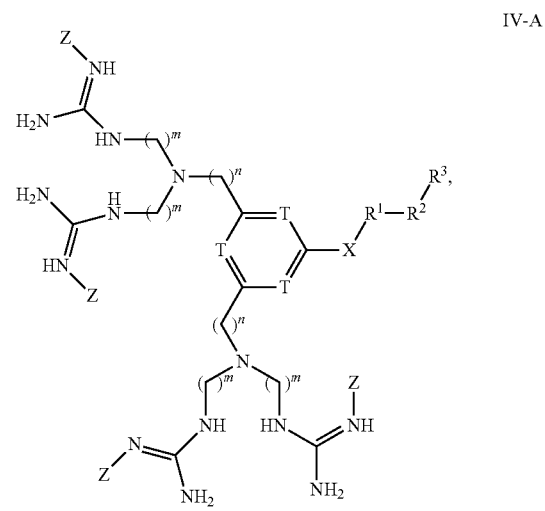

IV-A

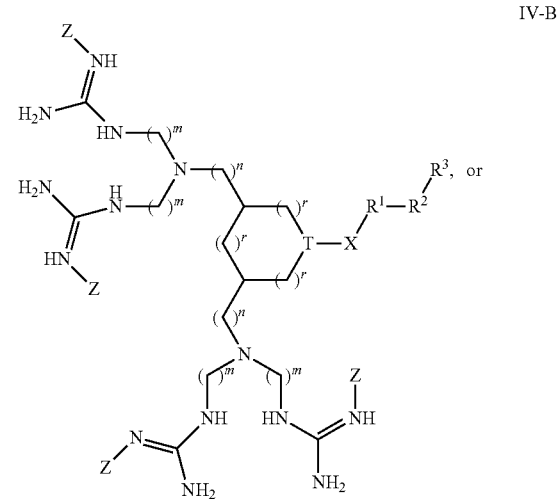

IV-B

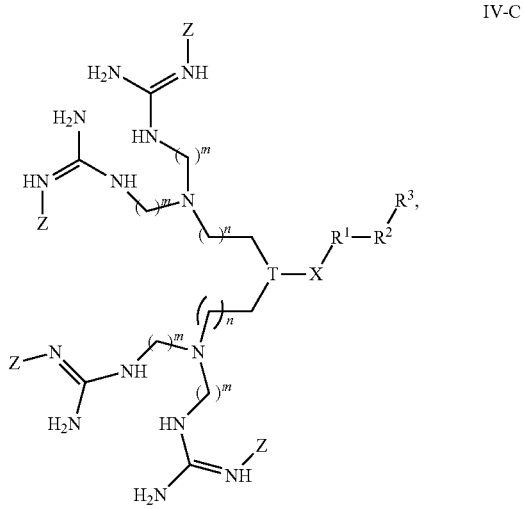

IV-C wherein X, Z, $R^1$, $R^2$, $R^3$, m, and n are as defined above; T is CH or N; and r is each independently selected from 0, 1, 2, or 3.
In various embodiments of Formulas I to IV, the present disclosure provides compounds having the following structures:
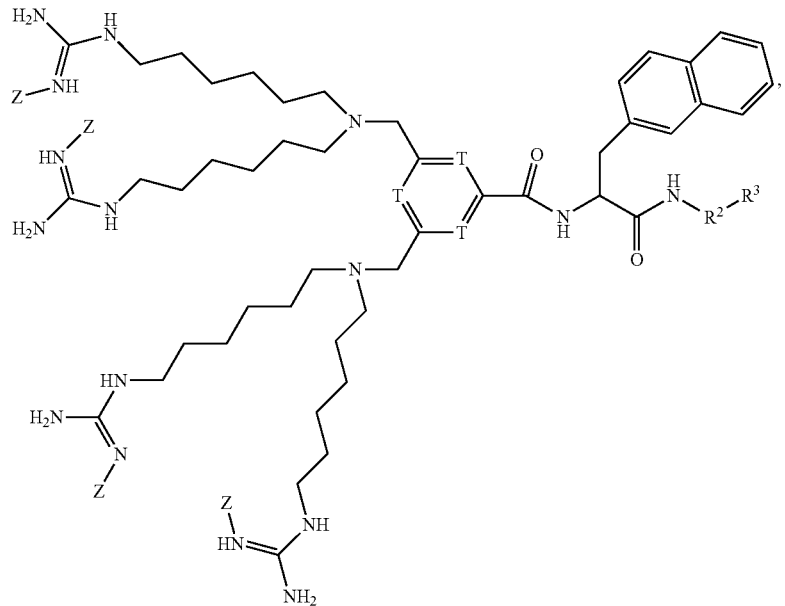
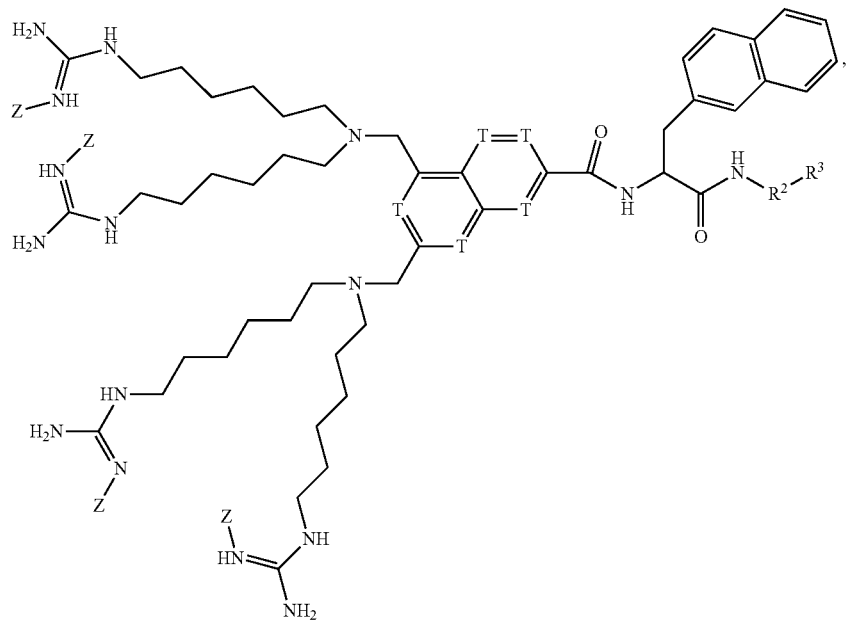

-continued
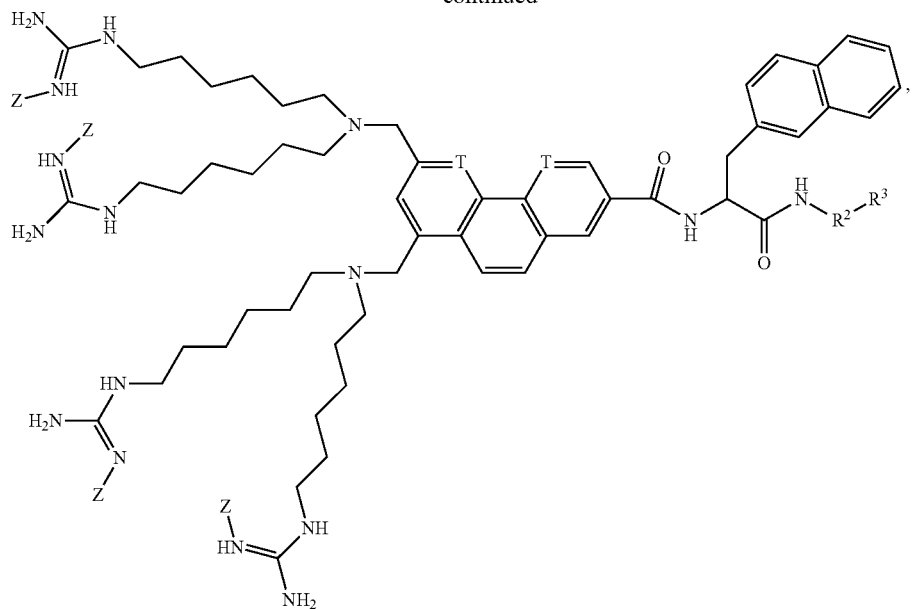
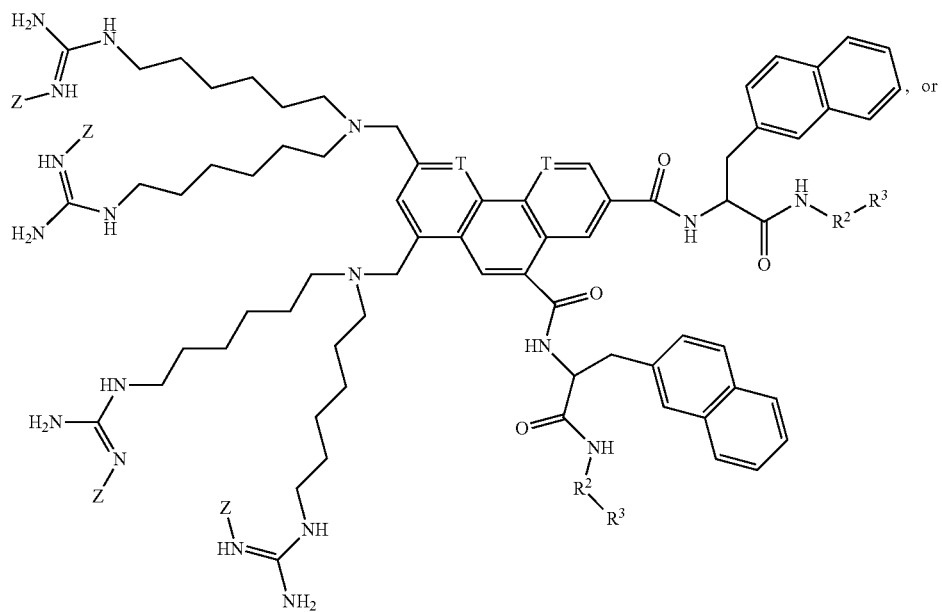

-continued
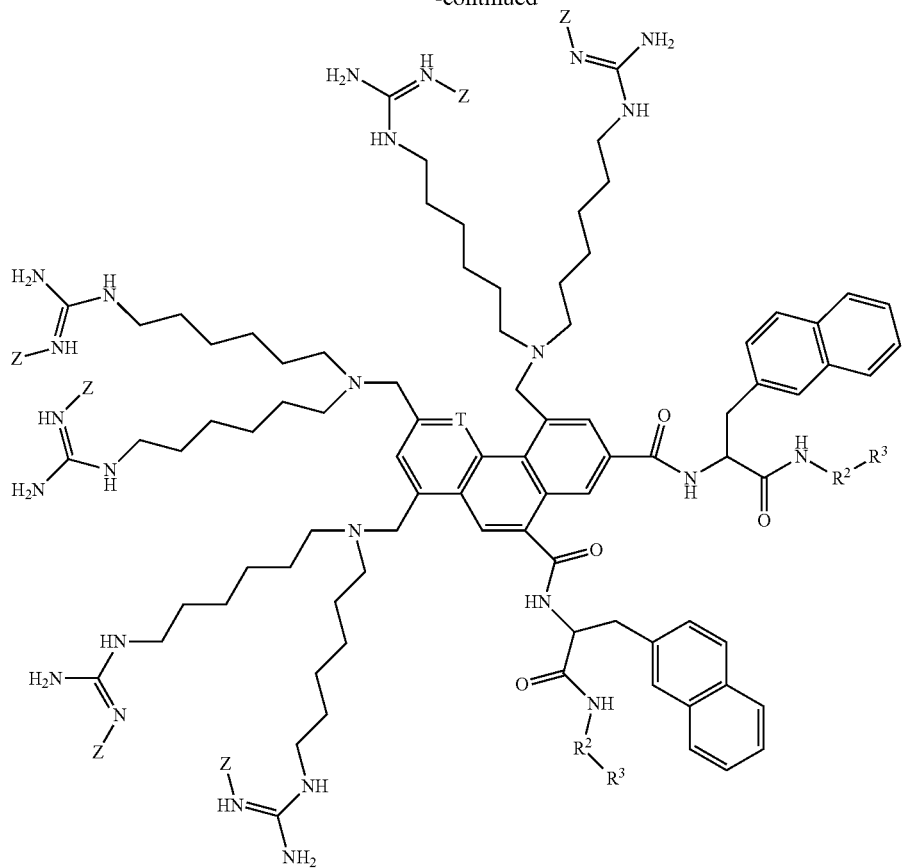
or pharmaceutically acceptable salts or tautomers thereof, wherein Z is defined above; each T is independently CH or N; $R^2$ is a bond or a moiety comprising an aromatic ring; and $R^3$ is a cargo moiety.
In various embodiments of Formulas I to IV, the present disclosure provides compounds having the following structures:
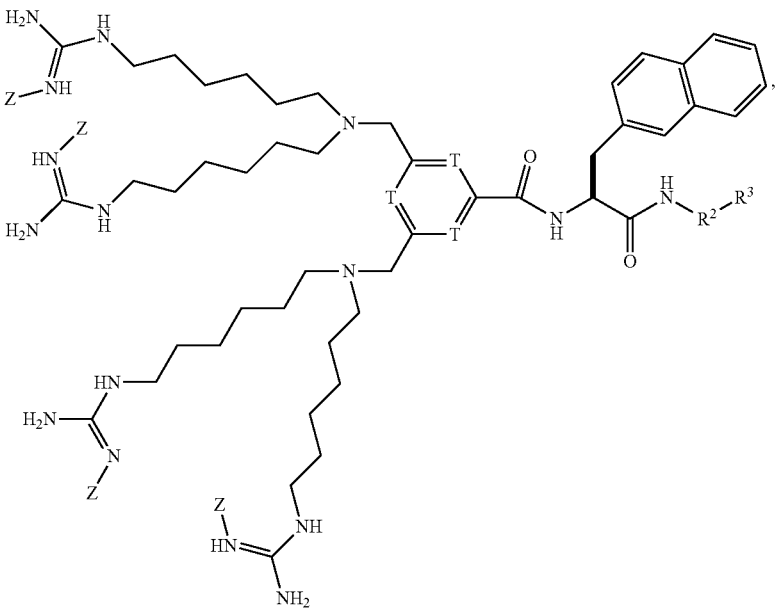

-continued
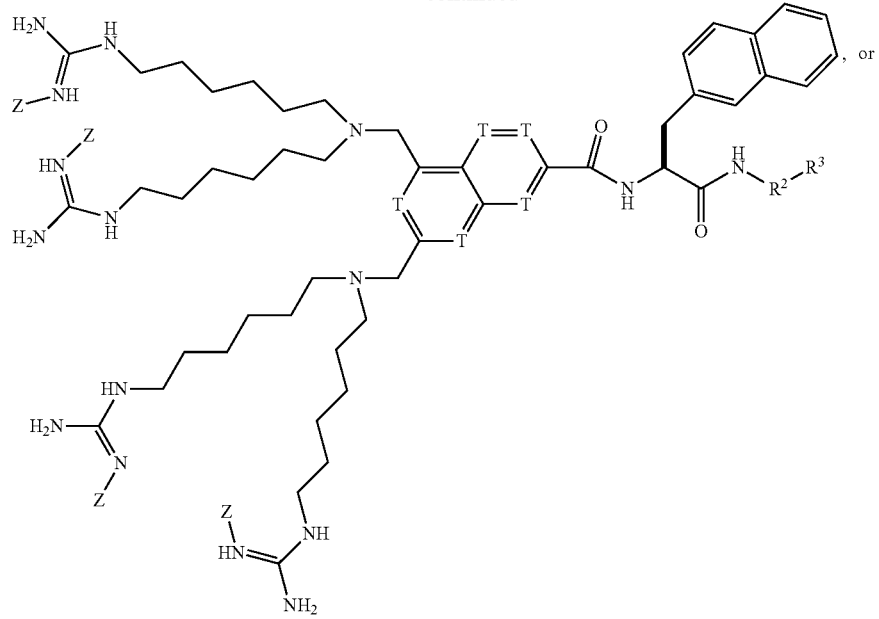
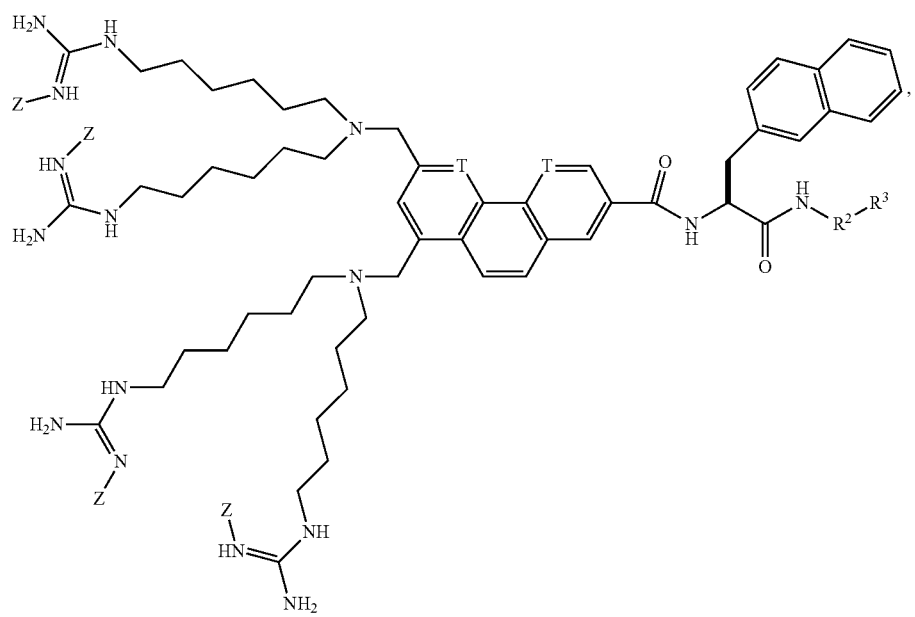
or pharmaceutically acceptable salts or tautomers thereof, wherein Z is defined above; each T is independently CH or N; $R^2$ is a bond or a moiety comprising an aromatic ring; and $R^3$ is a cargo moiety.

In some embodiments, the present disclosure provides a compound having the following structure:

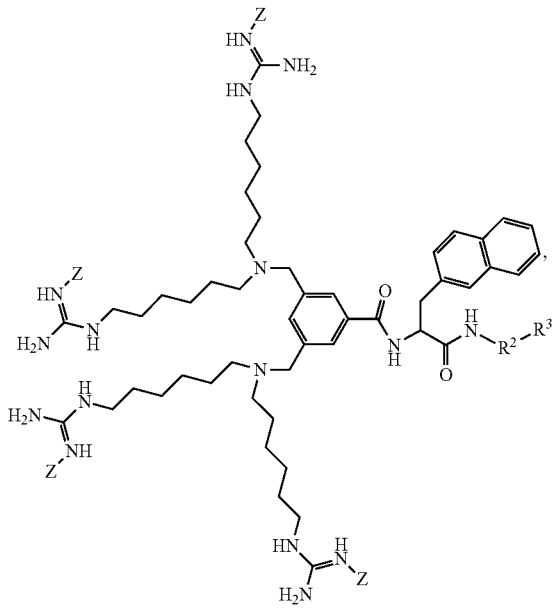

or pharmaceutically acceptable salts or tautomers thereof, wherein Z is defined as above; $R^2$ is a bond or a moiety comprising an aromatic ring; and $R^3$ is absent or a cargo moiety.

In some embodiments, the present disclosure provides a compound having the following structure:

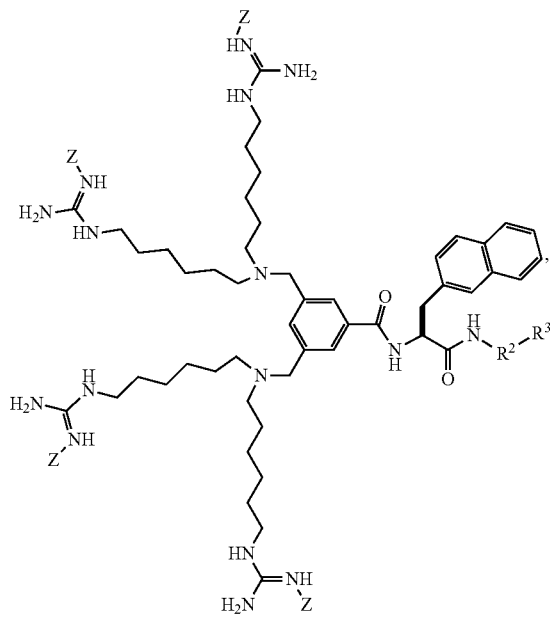

or pharmaceutically acceptable salts or tautomers thereof, wherein Z is defined as above; $R^2$ is a bond or a moiety comprising an aromatic ring; and $R^3$ is absent or a cargo moiety.

In some embodiments, the present disclosure provides a compound having the following structure:

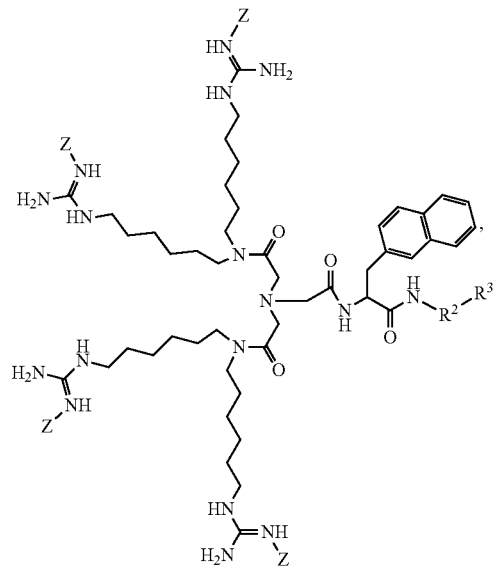

or pharmaceutically acceptable salts or tautomers thereof, wherein Z is defined as above; $R^2$ is a bond or a moiety comprising an aromatic ring; and $R^3$ is absent or a cargo moiety.

In some embodiments, the present disclosure provides a compound having the following structure:

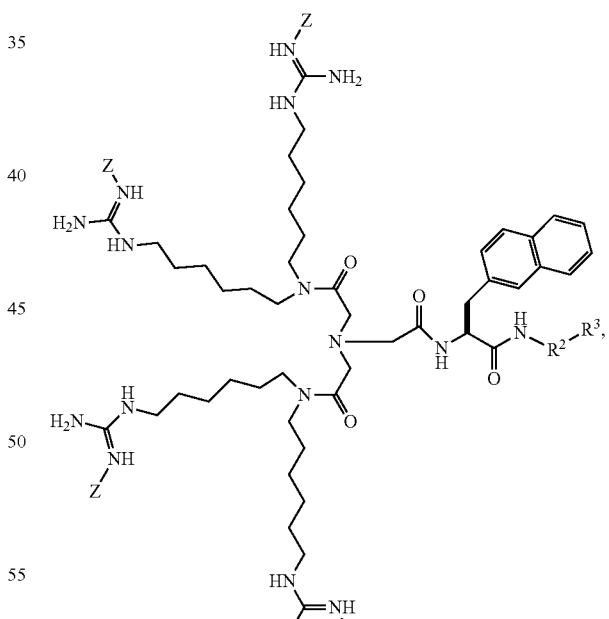

or pharmaceutically acceptable salts or tautomers thereof, wherein Z is defined as above; $R^2$ is a bond or a moiety comprising an aromatic ring; and $R^3$ is absent or a cargo moiety.

In some embodiments, the present disclosure provides a compound having the following structure:

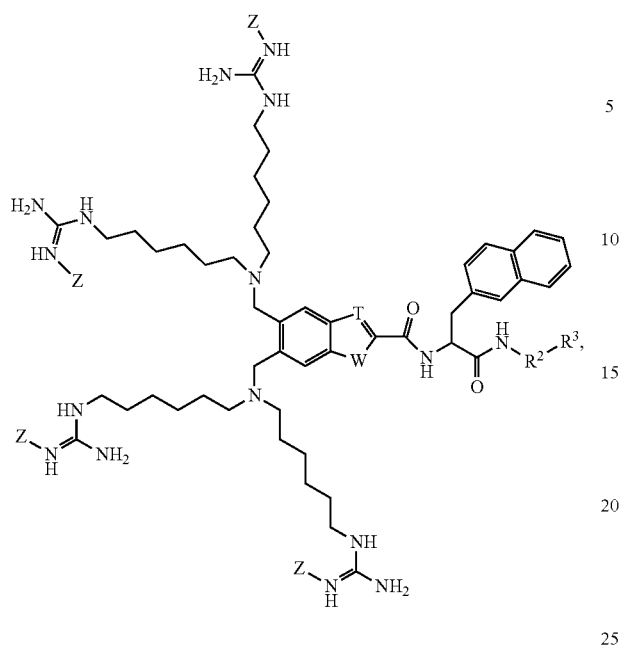

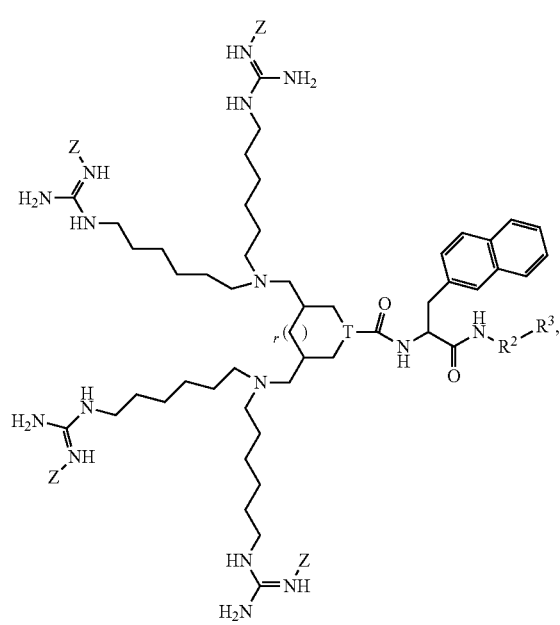

or pharmaceutically acceptable salts or tautomers thereof, wherein Z is defined above; T is CH or N; W is O, S, or NH; R² is a bond or a moiety comprising an aromatic ring; and R³ is absent or a cargo moiety.

In some embodiments, the present disclosure provides a compound having the following structure:

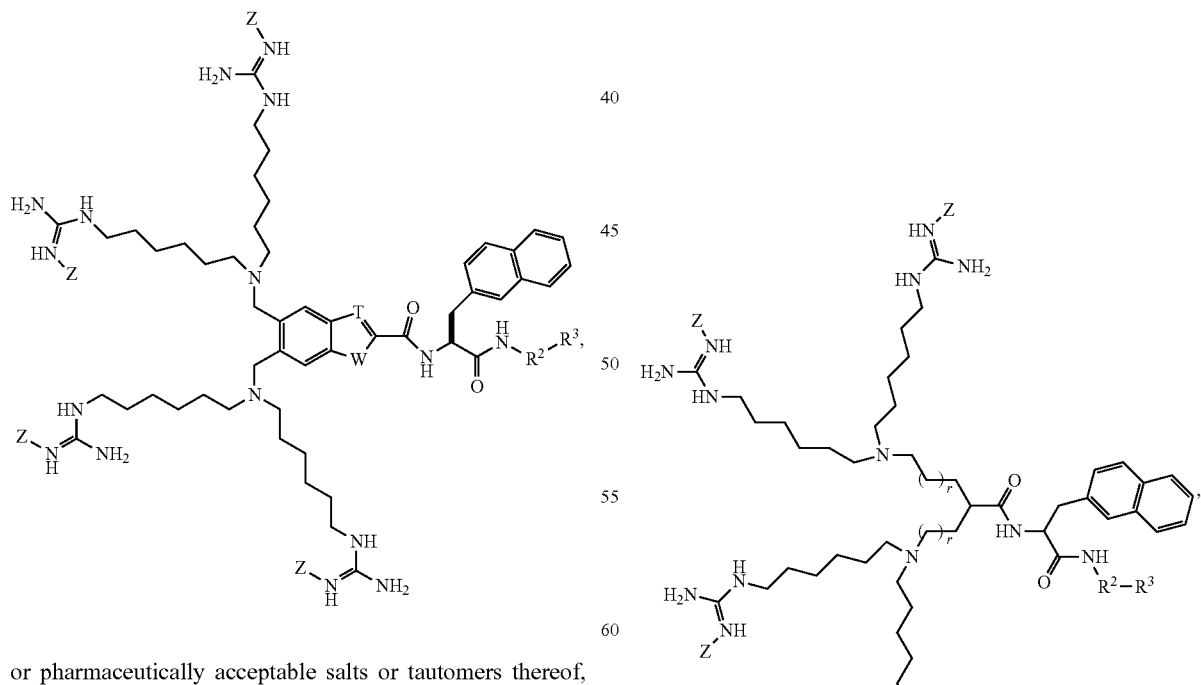

or pharmaceutically acceptable salts or tautomers thereof, wherein Z is defined above; T is CH or N; W is O, S, or NH; R² is a bond or a moiety comprising an aromatic ring; and R³ is absent or a cargo moiety.

In some embodiments, the present disclosure provides a compound having the following structure:

47
-continued
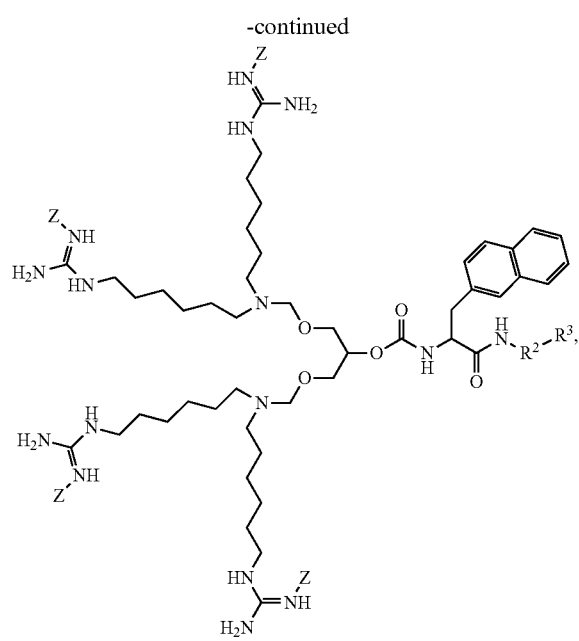
48
-continued
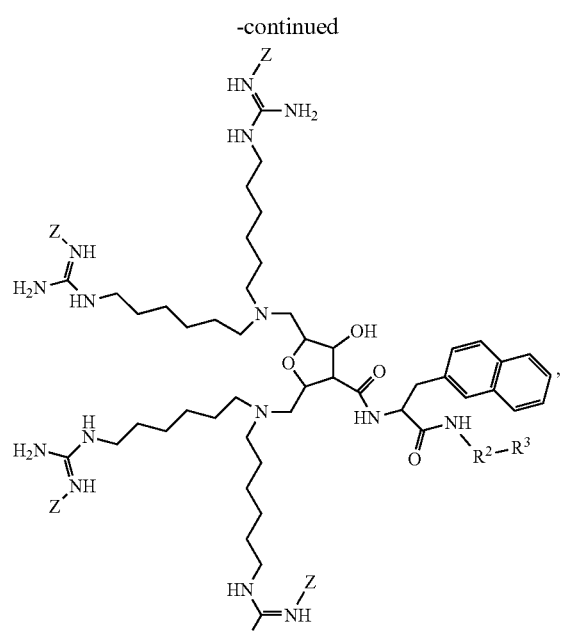
or pharmaceutically acceptable salts or tautomers thereof, wherein Z is defined above; T is CH or N; r is independently selected from 0, 1, 2, or 3; $R^2$ is a bond or a moiety comprising an aromatic ring; and $R^3$ is absent or a cargo moiety.
In some embodiments, the present disclosure provides a compound having the following structure:
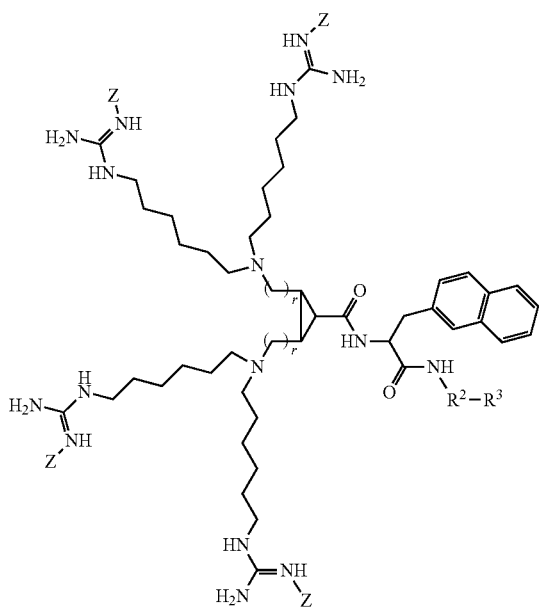
, or
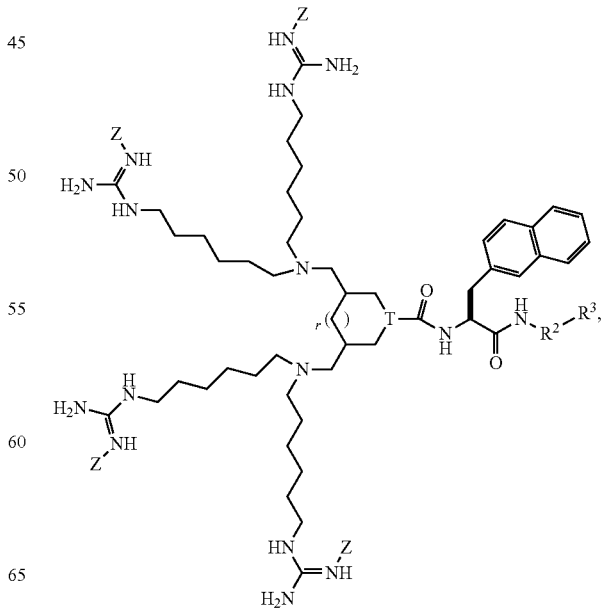

49
-continued

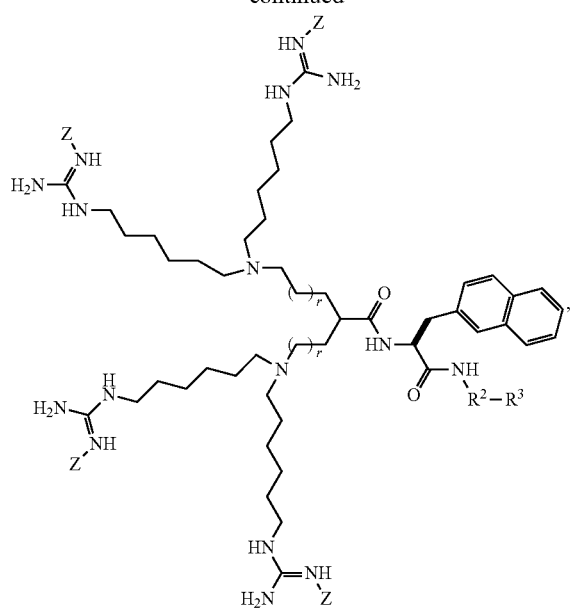

50
-continued

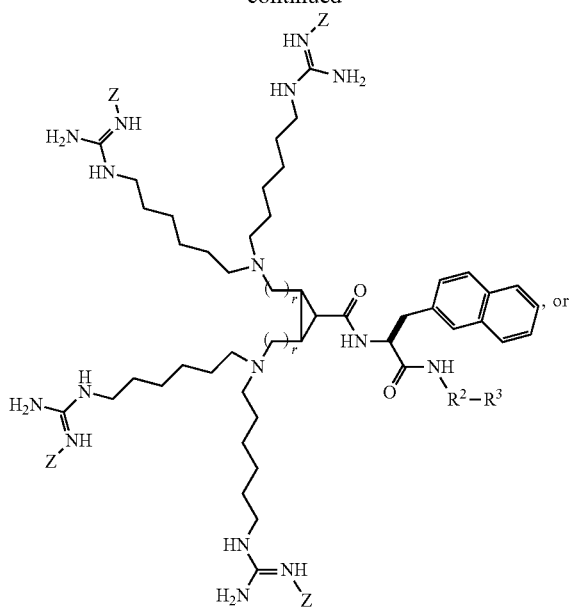

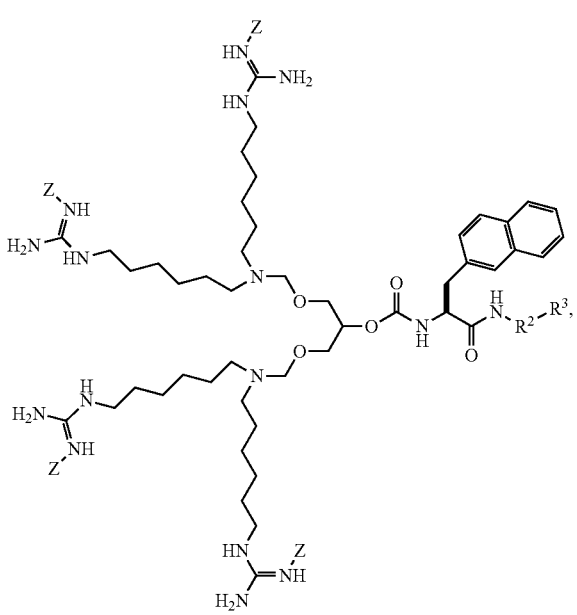

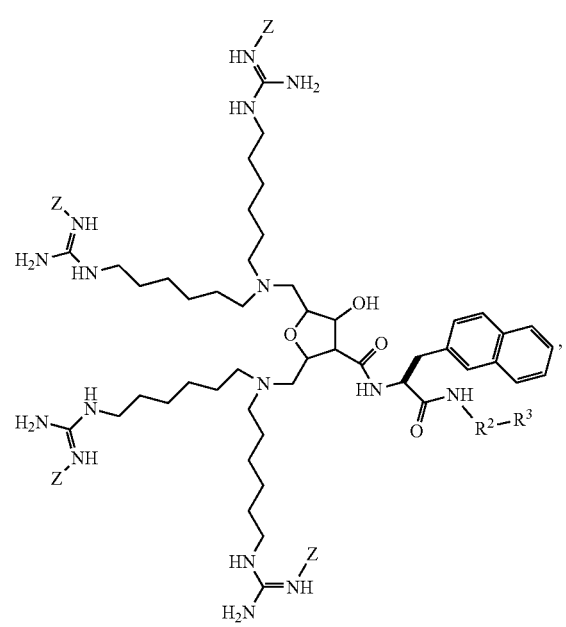

or pharmaceutically acceptable salts or tautomers thereof, wherein Z is defined above; T is CH or N; r is independently selected from 0, 1, 2, or 3; $R^2$ is a bond or a moiety comprising an aromatic ring; and $R^3$ is absent or a cargo moiety.

In some embodiments, r is 0 or 1. In certain embodiments, r is 0. In specific embodiments, r is 1. In other specific embodiments, r is 2. In further embodiments, r is 3.

In some embodiments, the present disclosure provides a compound having the following structure:

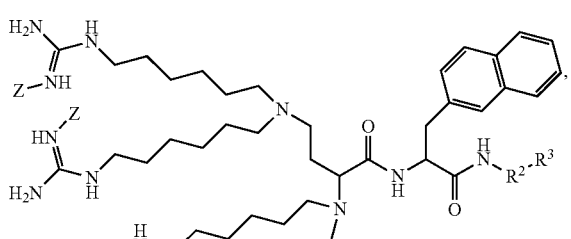
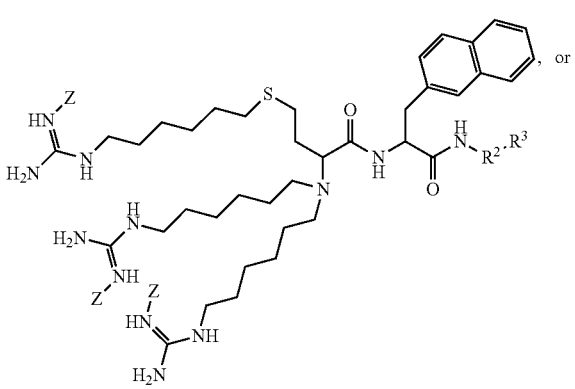
, or
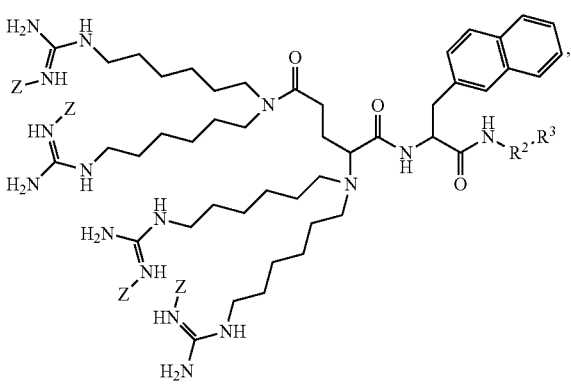
,
or pharmaceutically acceptable salts or tautomers thereof, wherein r and Z are defined above; $R^2$ is a bond or a moiety comprising an aromatic ring; and $R^3$ is absent or a cargo moiety.
In some embodiments, the present disclosure provides a compound having the following structure:
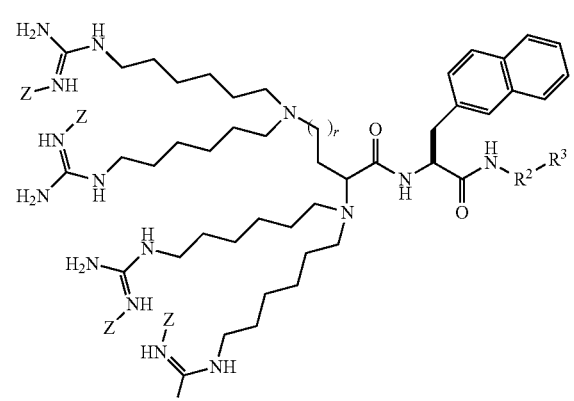
,
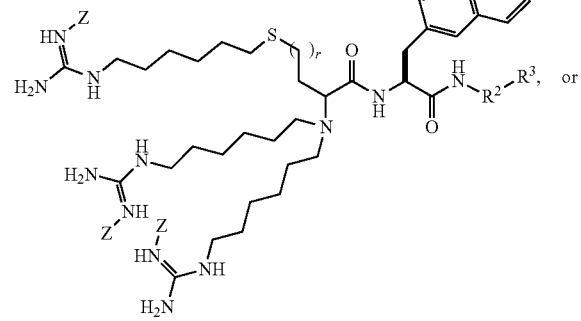
, or

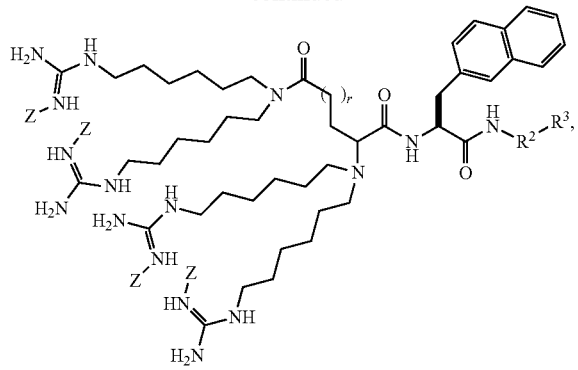

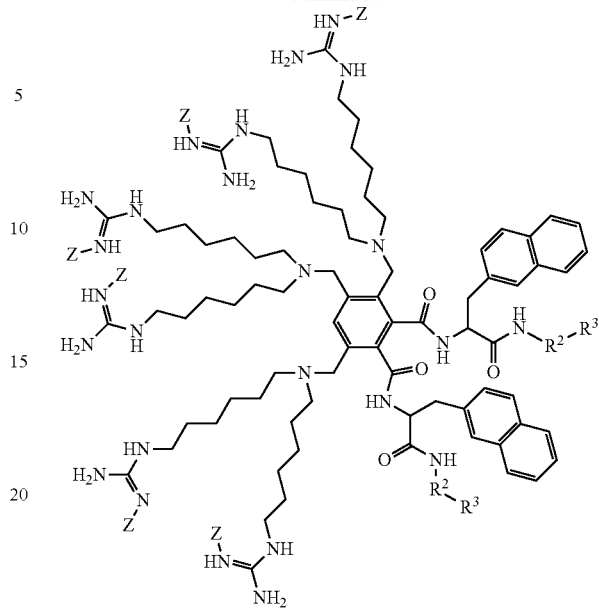

or pharmaceutically acceptable salts or tautomers thereof, wherein r and Z are defined above; $R^2$ is a bond or a moiety comprising an aromatic ring; and $R^3$ is absent or a cargo moiety.

In various embodiments of Formulas I to IV, the present disclosure provides compounds having the following structures:

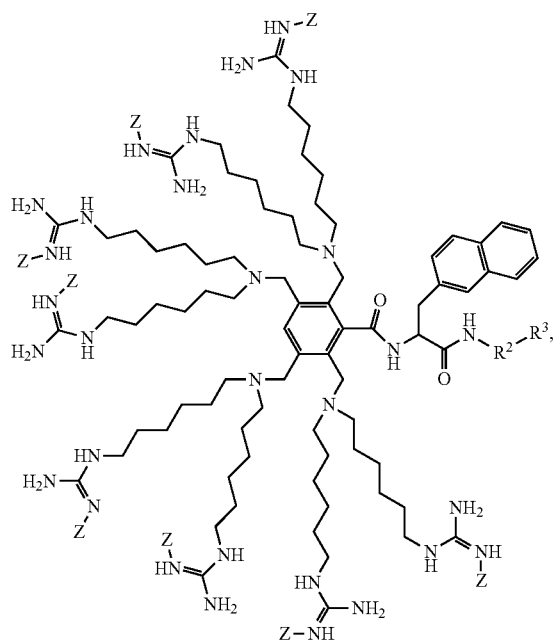

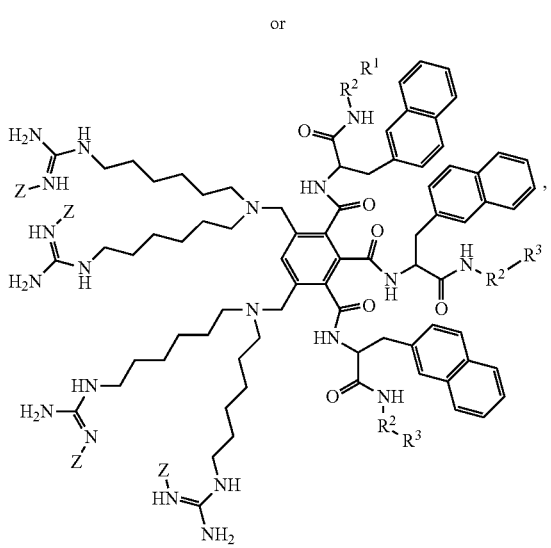

or or pharmaceutically acceptable salts or tautomers thereof, wherein Z is defined above; $R^2$ is a bond or a moiety comprising an aromatic ring; and $R^3$ is absent or a cargo moiety.

In various embodiments of Formulas I to IV, the present disclosure provides a compound having the following structures:

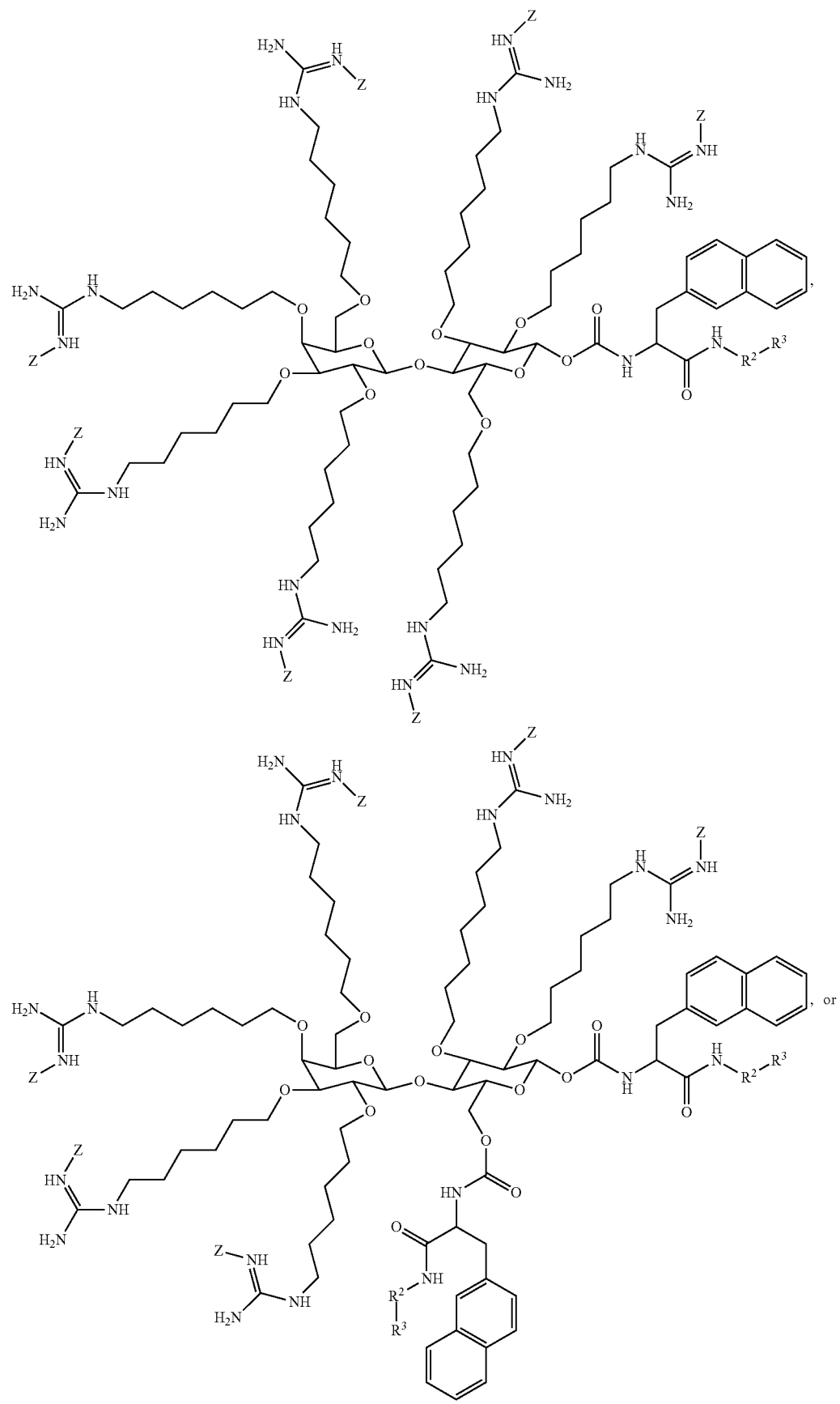

-continued

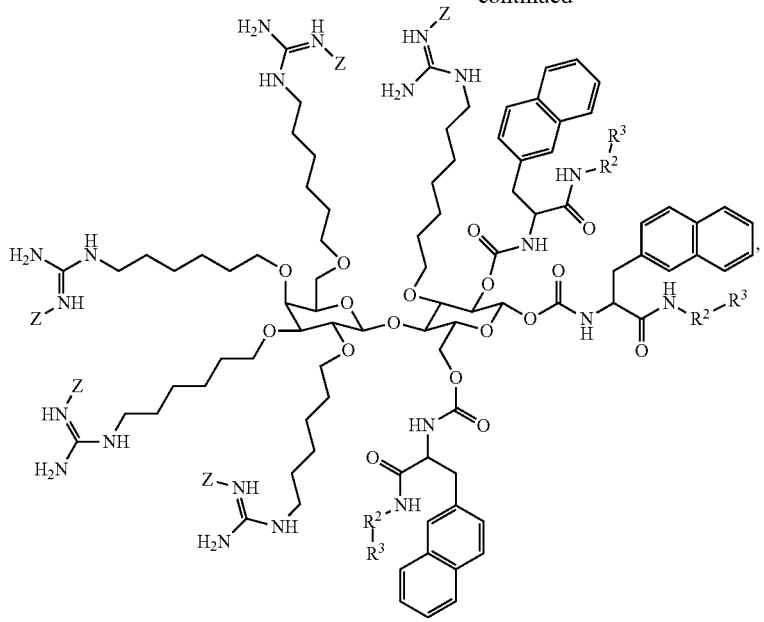

or pharmaceutically acceptable salts or tautomers thereof, wherein Z is defined above; $R^2$ is a bond or a moiety comprising an aromatic ring; and $R^3$ is absent or a cargo moiety.

As noted above, the compounds of the present disclosure possess one or more guanidine moieties, which can each independently be present in a protonated guanidinium form. In some embodiments, the percentage of guanidinium moieties to the total combined number of guanidine and guanidinium moieties in each CPM is in the range of from about 10% to about 100%, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges therebetween.

In various embodiments of the present disclosure, compounds are provided having a cargo moiety comprising a therapeutic agent.

In various embodiments, a pharmaceutical composition comprising a compound of the present disclosure is provided.

Cargo

The cargo moiety may be any moiety which is suitable for intracellular delivery. In particular embodiments, the cargo moiety is suitable for mitochondrial delivery.

The cargo moiety can comprise any cargo of interest, for example a detectable moiety, a therapeutic moiety, and the like, or any combination thereof. In some embodiments, the cargo can be conjugated to the rest of the molecule through a linker. Thus, all references to "cargo moiety" or "cargo" herein may include a linker moiety.

In some examples, the cargo moiety can comprise one or more additional amino acids (e.g., K, UK, TRV); a linker (e.g., bifunctional linker LC-SMCC); coenzyme A; phosphocoumaryl amino propionic acid (pCAP); 8-amino-3,6-dioxaoctanoic acid (miniPEG); L-2,3-diaminopropionic acid (Dap or J); L-β-naphthylalanine; L-pipecolic acid (Pip); sarcosine; trimesic acid; 7-amino-4-methylcourmarin (Amc); fluorescein isothiocyanate (FITC); L-2-naphthylalanine; norleucine; 2-aminobutyric acid; or combinations thereof. The aforementioned groups provide suitable sites for conjugation of therapeutic agents and/or detectable moieties. In some embodiments, the linker comprises an amino acid, alkylene, alkenylene, alkynylene, carbocyclyl, heterocyclyl, or $-R^k-X^3-R^l-$ wherein $R^k$ and $R^l$ are independently selected from alkylene, alkenylene, alkynylene, carbocyclyl, or heterocarbocyclyl, each of which are optionally substituted, and $X^3$ is O, N, or S.

Detectable Moiety

The detectable moiety can comprise any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiments, the label is detectable without the addition of further reagents.

In some embodiments, the detectable moiety is a biocompatible detectable moiety, such that the compounds can be suitable for use in a variety of biological applications. "Biocompatible" and "biologically compatible", as used herein, generally refer to compounds that are, along with any metabolites or degradation products thereof, generally non-toxic to cells and tissues, and which do not cause any significant adverse effects to cells and tissues when cells and tissues are incubated (e.g., cultured) in their presence.

The detectable moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru (dpp)$_3$); Ru (II) tris (1,10-phenanthroline) (Ru(phen)$_3$), tris(2,2'-bipyridine)ruthenium (II) chloride hexahydrate (Ru(bpy)$_3$); erythrosine B; fluorescein; fluorescein isothiocyanate (FITC); eosin; iridium (III) ((N-methyl-benzimidazol-2-yl-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitrophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxyfluorecsein; carboxynaphthofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; dioctadecylcycloxacarbocyanine; fluorenylmethyloxycarbonyl chloride; 7-amino-4-methylcourmarin (Amc); green fluorescent protein (GFP); and derivatives or combinations thereof.

In some examples, the detectable moiety can comprise Rhodamine B (Rho), fluorescein isothiocyanate (FITC), 7-amino-4-methylcourmarin (Amc), green fluorescent protein (GFP), or derivatives or combinations thereof.

Therapeutic Moiety

In some examples, the cargo moiety comprises one or more therapeutic moieties. Therapeutic moiety refers to a group that when administered to a subject will reduce one or more symptoms of a disease or disorder.

The therapeutic moiety can comprise a wide variety of drugs, including antagonists, for example enzyme inhibitors, and agonists, for example a transcription factor which results in an increase in the expression of a desirable gene product (although as will be appreciated by those in the art, antagonistic transcription factors can also be used), are all included. In addition, therapeutic moiety includes those agents capable of direct toxicity and/or capable of inducing toxicity towards healthy and/or unhealthy cells in the body. Also, the therapeutic moiety can be capable of inducing and/or priming the immune system against potential pathogens.

In some embodiments, the therapeutic moiety is a peptide, protein, antibody, small molecule, oligonucleotide. As used herein, "small molecule' refers to a compound that has a molecular weight of about 1000 Daltons or less. In some embodiments, the therapeutic moiety is not able to permeate the one or both of the mitochondrial membranes (i.e., the therapeutic moiety is "membrane impermeable"). The therapeutic moiety can, for example, comprise an anticancer agent, antiviral agent, antimicrobial agent, anti-inflammatory agent, immunosuppressive agent, anesthetics, or any combination thereof.

The therapeutic moiety can comprise an anticancer agent. Example anticancer agents include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, $C_{225}$, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, —Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Oraprd, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR.

In some examples, the therapeutic moiety can comprise an antiviral agent, such as ganciclovir, azidothymidine (AZT), lamivudine (3TC), etc.

In some examples, the therapeutic moiety can comprise an antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

Methods of Making

The compounds described herein can be prepared in a variety of ways known to one skilled in the art of organic synthesis or variations thereon as appreciated by those skilled in the art. Optimum reaction conditions can vary with the particular reactants or solvents used, but such conditions can be determined by one skilled in the art. Synthetic techniques can be found, for example, in Cary and Sundberg, Advanced Organic Chemistry, Part B: Reactions and Synthesis, 5$^{th}$ Ed. Springer, 2007, and Corey and Cheng, The Logic of Chemical Synthesis, 4$^{th}$ Ed., Wiley and Sons, 1995, each of which is herein incorporated by reference in its entirety. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The compounds described herein can be prepared from readily available starting materials. The starting materials and reagents used in preparing the disclosed compounds and compositions are either available from commercial suppliers such as Aldrich Chemical Co., (Milwaukee, WI), Acros Organics (Morris Plains, NJ), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, IL), Schering Plough (Kenilworth, NJ), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopentyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for aspartic acid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N, N, N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCI), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxyacetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxyacetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thioanisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

As discussed above, the compounds of the disclosure (e.g., compounds according to Formula I, II, III, and IV) comprise bonding groups, which represent the resultant chemical moiety formed after a component of the compound (e.g., guanidinium group, $R^1$, etc.) is attached to the multivalent scaffold A. Non-limiting examples of the bonding group X that attaches the moiety comprising an aromatic ring to the multivalent scaffold include

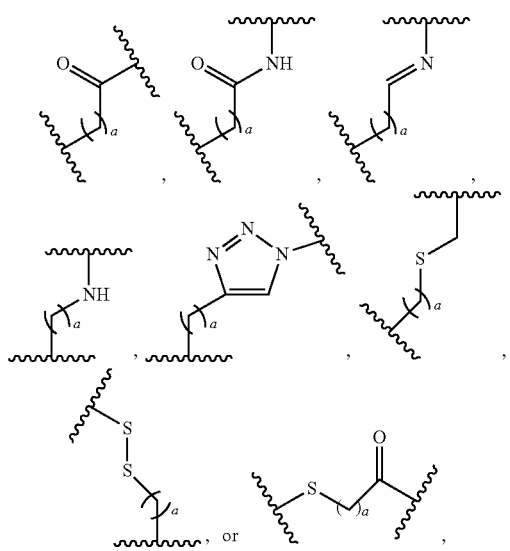

wherein each a is independently number from 0 to 10. Non-limiting examples of the bonding group Y that attaches the guanidinium group to the multivalent scaffold include —N—, —S—, —

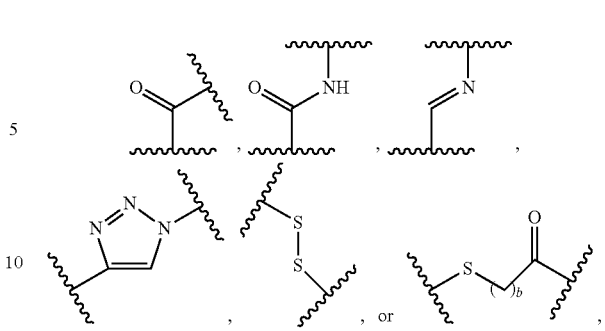

wherein each b is independently a number from 0 to 10.

Such bonding groups can be formed according to reactions that are well known in the art of synthetic organic chemistry, e.g., by subjecting a precursor of A bearing a functional group which is capable of undergoing a reaction with a functional group on a precursor of $R^1$ to appropriate reaction conditions to form X. For example, the precursor of A may bear a carboxylic acid or acyl halide, and the precursor of $R^1$ may bear an amino group, and these components may be allowed to react under appropriate conditions to form an amide group which binds A and $R^1$. As another example, the precursor of A may bear a nitrile group and the precursor of $R^1$ may bear an alkynyl group, and these components may be allowed to react under appropriate conditions to form a triazole group which binds which A and $R^1$.

Compositions and Methods of Administration

In various embodiments, the present disclosure provides for methods of delivering a therapeutic agent to the mitochondria of cell, comprising contacting the cell with a compound or pharmaceutical composition disclosed herein.

In some embodiments, the present disclosure provides for methods of treating a disease, comprising administering a compound or pharmaceutical composition disclosed herein.

In certain embodiments, the methods are for treating a mitochondrial disease.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and non-aqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Synthesis of Non-Peptidic Cell-Penetrating Motifs

Scheme 1. General Approach to Synthesis of CPMs

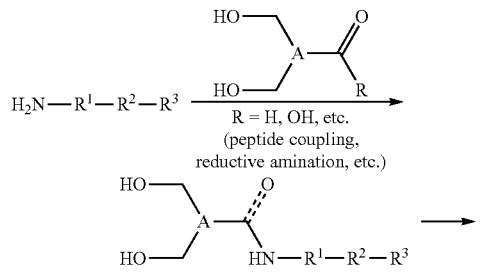

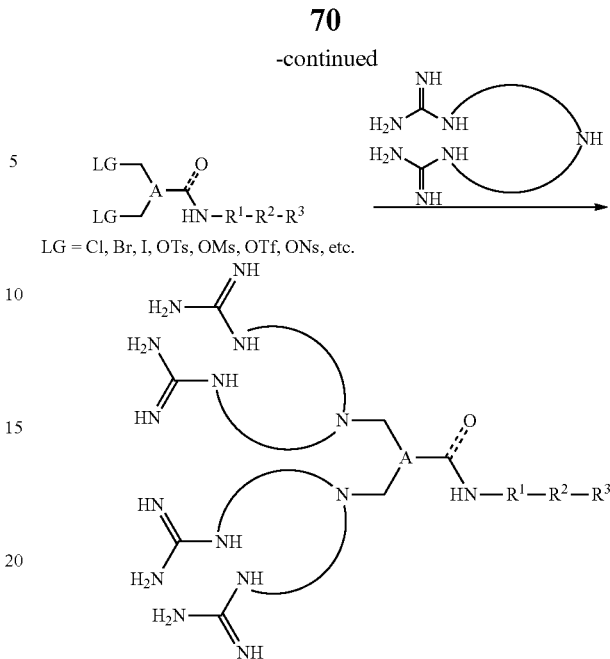

A variety of non-peptide multivalent moieties can be utilized in the CPMs of the present disclosure. One of skill in the art would recognize a number of known methods for accomplishing the assembly of such compounds. As exemplified in Scheme 1 for a representative trivalent A moiety, a carboxyl group (COR) can serve as a precursor to a bonding group useful in linking A to $R^1$. Numerous other functional groups can be envisioned for this purpose as well. To facilitate linkage to the guanidine/guanidinium groups, hydroxyl moieties appended to A can be converted to a suitable leaving group (LG) and further functionalized with guanidine/guanidinium-containing moieties to provide CPMs described herein. Below are specific examples for the preparation of CPM1-3 that illustrate the concepts highlighted in Scheme 1.

CPM1 was readily synthesized on solid phase, starting with the miniPEG-Lys linker (Scheme 2). After the sequential addition of Fmoc-Nal and 3,5-bis(bromomethyl)benzoic acid (Bmb) by standard peptide chemistry, the four guanidinium groups were installed by treating the resin-bound Bmb moiety with excess 1,1'-(azanediylbis(hexane-6,1-diyl))diguanidine under mildly basic condition (pH 9). CPM1 was cleaved from the resin and deprotected (at the lysine side chain) by treatment with trifluoroacetic acid (TFA).

Scheme 2. Overview of Synthetic Route

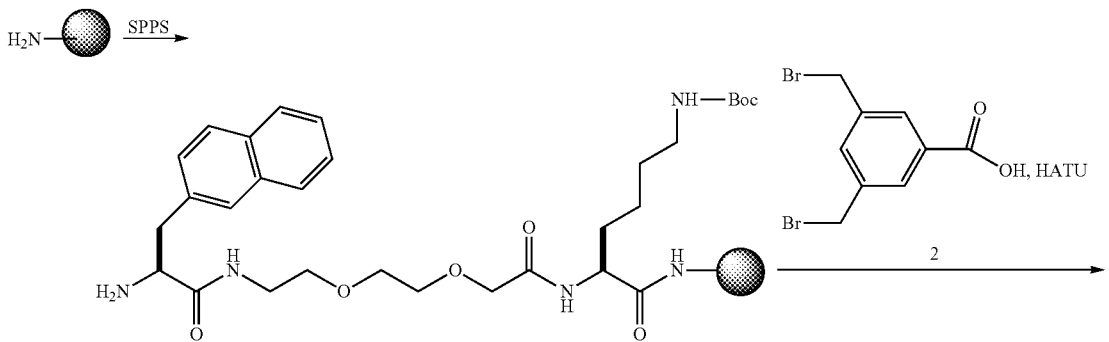

-continued

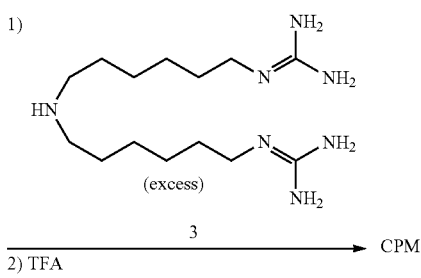

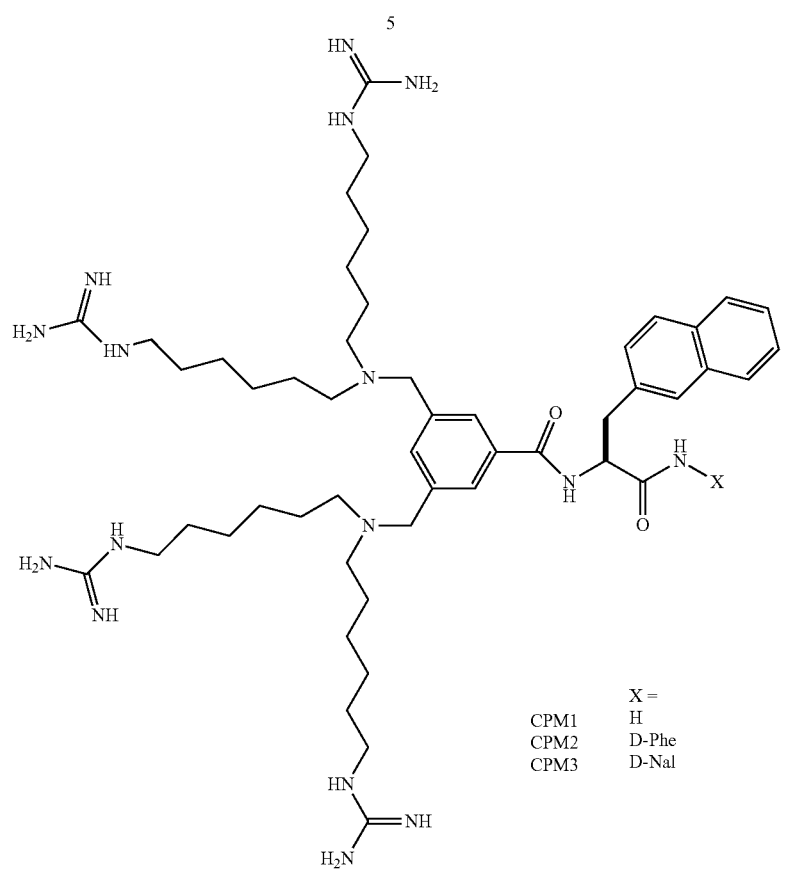

| | X = |
|---|---|
| CPM1 | H |
| CPM2 | D-Phe |
| CPM3 | D-Nal |

Scheme 3. Synthetic Route for Preparing 3,5-bis(bromomethyl)benzoic acid (2)

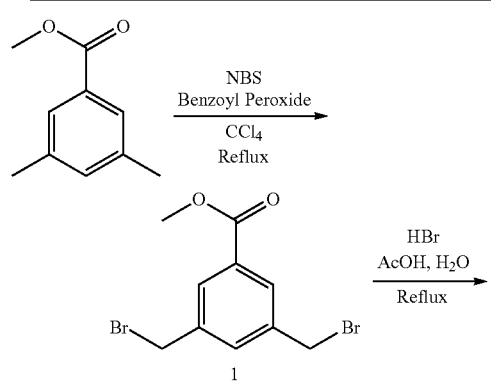

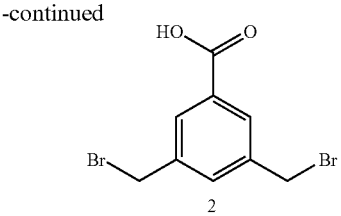

Synthesis of Methyl-3,5-bis(bromomethyl)benzoate (1)

This compound was prepared based on literature procedure with minor modifications as described below. Methyl-3,5-dimethylbenzoate (1.0 g, 6.09 mmol), N-bromosuccinimide (2.16 g, 12.2 mmol), and benzoyl peroxide (29.5 mg, 0.12 mmol) were dissolved in 10 mL of carbon tetrachloride.

The mixture was refluxed (with stirring) for 3 h. The reaction mixture was allowed to cool to 25° C. and filtered and the filtrate was washed with 6 mL of water. The organic layer was dried with anhydrous sodium sulfate and concentrated under reduced pressure. The pale yellow residue was re-suspended in 50 mL of petroleum ether and kept at 4° C. for 48 h. The precipitated product was purified by column chromatography on silica gel and eluted with 15:1 (v/v) hexane/ethyl acetate. The product was obtained as white crystalline solid (564 mg, 1.76 mmol, 29% yield). $^1$H NMR (300 MHz, CDCl$_3$) δ=7.99 (s, 2H) 7.62 (s, 1H) 4.50 (s, 4H) 3.94 (s, 3H).

Synthesis of 3,5-Bis(bromomethyl)benzoic Acid (2)

This compound was prepared based on literature procedure with minor modifications as described below. Methyl 3,5-bis(bromomethyl)benzoate (560 mg, 1.74 mmol) was suspended in 11 mL of 3:2 (v/v) acetic acid/water. A hydrogen bromide solution (33% in AcOH; 11 mL) was added and the mixture was refluxed for 20 h. The mixture was allowed to cool and poured over 40 mL of ice cold water. The precipitate was filtered and washed twice with cold water. A light brown solid (308 mg, 1 mmol, 57% yield) was obtained as product. $^1$H NMR (300 MHz, CDCl$_3$) δ=8.07 (s, 2H) 7.69 (s, 1H) 4.52 (s, 4H).

Scheme 4. Synthetic Route for Preparing 1,1′(Azanediylbis(hexane-6,1-diyl))diguanidine (3)

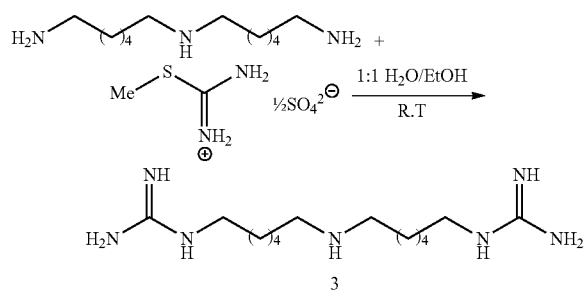

Synthesis of 1,1-(Azanediylbis(hexane-6,1-diyl))diguanidine (3)

This compound was prepared based on literature procedure with minor modifications as described below. Bis(hexamethylene)triamine (1.08 g, 5 mmol) was added to a solution of S-methylisothiourea sulfate (1.39 g, 10 mmol) in 7 mL of 1:1 water/ethanol and the mixture was stirred for 16 h at ambient temperature. The white crystalline precipitate formed was filtered and washed with ethanol. The crude product was re-dissolved in 30 mL of distilled water at 60° C. and isopropanol (3 mL) was carefully layered on top of the solution. After overnight standing at 4° C., the product crystallized as fine white crystals, which were isolated by filtration (1.06 g, 3.55 mmol, 71% yield). $^1$H NMR (300 MHz, D$_2$O) δ=3.21 (t, J=7.0 4H) 3.05 (t, J=7.9 Hz, 4H) 1.70 (br, 4H) 1.63 (t, J=6.4 Hz, 4H) 1.42 (br, 8H)

Synthesis of 2-Nal-miniPEG-Lys (4)

Coupling of the Fmoc-amino acids and Rink amide linker were carried out following standard Fmoc-based solid phase peptide synthesis. A typical coupling reaction used 4 equiv. of Fmoc-amino acid, 4 equiv. of 2-(7-aza-1H-benzotriazole-1-yl)-1,1,3,3-tetramethyluronium hexafluorophosphate (HATU), and 8 equiv. of N,N-diisopropylethylamine (DIPEA) for 45 min in DMF at ambient temperature. Rink amide linker was coupled onto TentaGel resin to permit final release of CPMs with amidated C-terminus. Fmoc-Lys (Boc)-OH, Fmoc-miniPEG-OH and Fmoc-2-Nal-OH were then sequentially installed. Removal of the N-terminal Fmoc group, provided the free amine 4 for further functionalization.

General Synthesis of CPMs

Amine 4 was acylated with 3 equiv. 3,5-bis(bromomethyl) benzoic acid (2) using 3 equiv. HATU and 6 equiv. DIPEA in DMF for 0.5 hr. Next, 10 equiv. of 1,1′-(azanediylbis (hexane-6,1-diyl))diguanidine (3) was dissolved in pH 9, 0.5 M sodium bicarbonate/acetonitrile (2:1, v/v) mixture and mixed with the resin for 3 h at 50° C. After extensive washings with water, DMF, and DCM, the CPM was released from the resin with TFA/water/triisopropylsilane/ 1,3-dimethoxybenzene (92.5:2.5:2.5:2.5, v/v) for 3 h. The crude CPM was purified by reversed-phase HPLC equipped with a 018 column, eluted with a linear gradient of 10-50% acetonitrile in HPLC water containing 0.05% TFA. The same method was used to prepare other CPMs and their conjugates as well as $(F_xr)_3$-conjugated peptides.

Synthesis of TPP-Conjugated Peptides

The TPP-conjugated peptide was synthesized also on Rink amide resin (0.43 mmol/g). The peptide ananan-mini-PEG-K were installed using solid phase peptide synthesis as described above, the N-terminal amine was then acylated with 4 equiv. of 6-bromohexanoic acid, 4 equiv. of HATU, and 8 equiv. of DIPEA in DMF for 0.5 hr. Next, the resin was reacted with 4 equiv. of triphenylphosphine in DMF for 10 h at 70° C. After exhaustive washing with DMF and DCM, the TPP-conjugated peptide was released and purified as described above.

Procedure for Fluorescent Labeling 1 mg of the purified compound was incubated with 1.2 equiv. of 5(6)-carboxynaphthofluorescein, or 5(6)-carboxytetremethylrhodamine, or 5(6)-carboxyfluorescein using 1.2 equiv. of N,N′-diisopropylcarbodiimide and 0.1 equiv. 4-(dimethylamino)pyridine in DMF for 1 h. The labeled product was purified again by reversed-phase HPLC equipped with a C$_{18}$ column. The authenticity and purity of the product (>95%) was assessed by reversed-phase HPLC equipped with an analytical C$_{18}$ column and high-resolution MALDI-TOF mass spectrometry.

Procedure for Preparing Geldanamycin (GA)-Containing CPMs (CPM3-GA)

MiniPEG-Cys linker was coupled at the C-terminus of CPM3 by mixing together 1 mg CPM3-miniPEG-Cys (0.721 μmol), 0.55 mg of 17-GMB-APA-GA (0.721 μmol), 20 μL DMF and 50 μL of PBS and reacting for 2 h. The mixture was purified using reverse phase HPLC on C$_{18}$ column. The authenticity and purity of the product (>95%) was assessed by reversed-phase HPLC equipped with an analytical C$_{18}$ column and high-resolution MALDI-TOF mass spectrometry.

Example 2

Evaluation of Biological Properties of Non-Peptidic Cell-Penetrating Motifs

CPM Entry into Mammalian Cytosol

Methods

Cell culture: HeLa cells were maintained in media consisting of DMEM, 10% fetal bovine serum (FBS) and 1% penicillin/streptomycin. Cells were cultured in a humidified incubator at 37° C. in the presence of 5% $CO_2$.

Flow cytometry: HeLa cells were cultured in 12-well plates ($1.5 \times 10^5$ cells per well) a day before the experiment, the cells were incubated with various concentrations of naphthofluorescein-labeled compounds in DMEM with 1% FBS at 37° C. for 2 h. The cells were washed with PBS twice, harvested with 0.25% trypsin, mixed with DMEM containing 10% FBS, pelleted by centrifuge at 200 g for 5 min. The cell pellet were washed twice with PBS and resuspended in PBS. Cells were analyzed on a BD FACS LSR II flow cytometry at 633 nm laser excitation and fluorescence emission in the APC channel.

Confocal microscopy imaging: HeLa cells ($5 \times 10^4$ cells) were seeded in a 35 mm glass-bottomed microwell dish (MatTek) and cultured for 24 h. Cells were gently washed twice with PBS and treated for 2 h with 2 μM tetramethyl-rhodamin-(Rho-) or fluorescein-(FL-) labeled CPM and their conjugates in phenol red-free DMEM supplemented with 1% FBS and 1% penicillin/streptomycin. Fifteen minutes prior to imaging, cells were treated with final concentration of 100 nM MitoTracker™ Green or MitoTracker™ Red. Before imaging, cells were gently washed three times with PBS and once with cell growth medium. Live cells without fixation were imaged on a Nikon AIR live-cell confocal microscope equipped with 100× oil objective. Pearson's coefficiency was analyzed with NIS-Elements AR.

Evaluation of Cytosolic Entry and Mitochondrial Targeting for CPM1

Figure 1B:
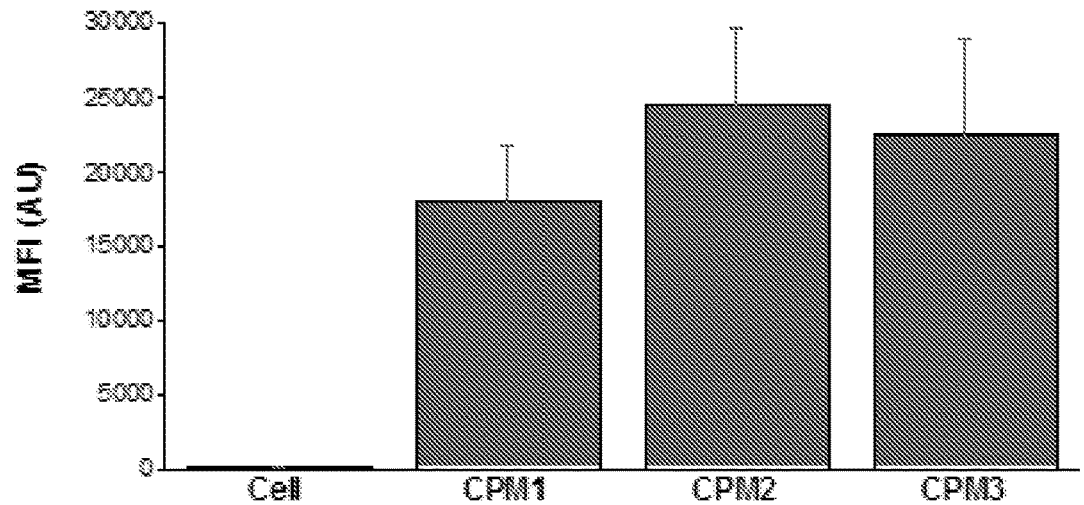
FIG. 1B shows the Cytosolic entry and mitochondrion localization of CPMs. i) Comparison of the cytosolic entry efficiency of CPM1-4 as analyzed by flow cytometry analysis of HeLa cells after 2 h treatment with 5 μM NF-labeled CPM1-4 or CPP9. The MFI values reported are the mean±SD of three independent experiments. ii) Live-cell confocal microsopic images of HeLa cells after 2 h treatment with 2 μM CPM1$^{TMR}$ (red) and 15 min incubation with MitoTracker Green. A merged image is shown on the right with the R value representing Pearson's correlation coefficient for co-localization. iii) Same as ii) but with CPM2. iv) Same as ii) but with CPM3.
Figure 1B:
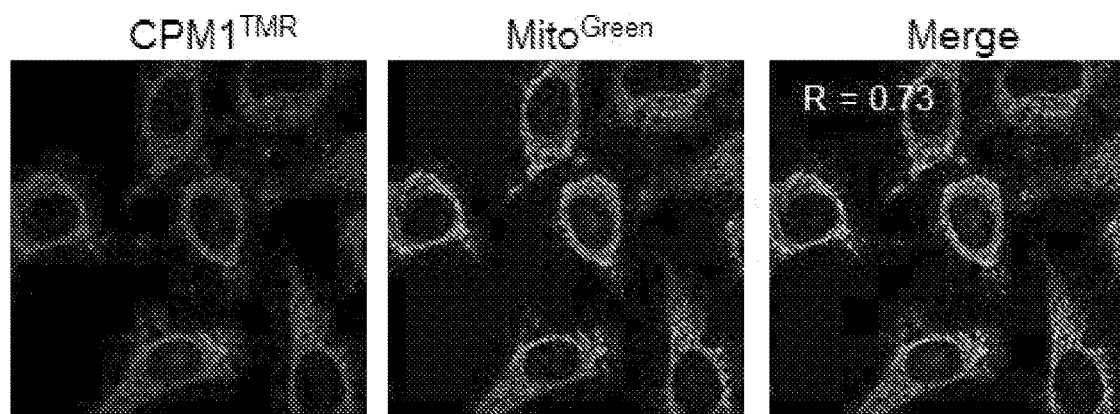
Figure 1B:

To test whether CPM1 can enter the cytosol of mammalian cells, it was labeled with a pH-sensitive dye, naphthofluorescein (NF; pKa=7.8), which is highly fluorescent inside the neutral cytosol and nucleus of eukaryotic cells, but essentially non-fluorescent when entrapped inside the acidic endosomal/lysosomal compartments (pH 4.5-6.5).[19] Flow cytometry analysis of HeLa cells treated for 2 h with 5 μM CPM1 NF produced a relative mean fluorescence intensity (MFI) of 179% [relative to $CPP9^{NF}$ (100%)] (FIG. 1B(i)), indicating that CPM1 efficiently enters the cytosol.

Figure 3:
FIG. 3 shows the co-localization of fluorescein-labeled CPM1 (CPM1$^{FL}$) and MitoTracker Red in HeLa cells. HeLa cells were treated for 2 h with 2 μM CPM1$^{FL}$ and then for 15 min with MitoTracker Red before being subjected to live-cell confocal microscopic imaging. A Pearson's correlation coefficient of 0.70 was observed.

To further confirm cytosolic entry, CPM1 was next labeled with a pH-insensitive dye, tetramethylrhodamine (TMR), and examined HeLa cells treated with 2 μM $CPM1^{TMR}$ by live-cell confocal microscopy. Surprisingly, $CPM1^{TMR}$ exhibited almost exclusively punctate fluorescence in the cytoplasmic region (FIG. 1B(ii)). Without being bound by a particular theory, this finding can be explained if after cytosolic entry, CPM1 is subsequently localized to subcellular structures such as the mitochondria, since some lipophilic cations had previously been shown to accumulate inside the mitochondrial matrix. Indeed, co-incubation of $CPM1^{TMR}$ treated HeLa cells with a mitochondrion-specific dye (MitoTracker Green) showed co-localization of $CPM1^{TMR}$ and MitoTracker Green, with a Pearson's correlation coefficient of 0.73 (FIG. 1B(iv)). In contrast, the $CPM1^{TMR}$ fluorescence had little overlap with that of an endosomal marker, FITC-labeled cyclodextrin, showing a correlation coefficient of 0.37 (FIG. 2). Additionally, the specific type of fluorophore does not impact the mitochondrial localization of CPM1, as fluorescein-labeled CPM1 showed a comparable level of co-localization with MitoTracker Red, with a correlation coefficient of 0.70 (FIG. 3).

Evaluation of Cytosolic Entry and Mitochondrial Targeting for CPM2 and CPM 3

Figure 4:
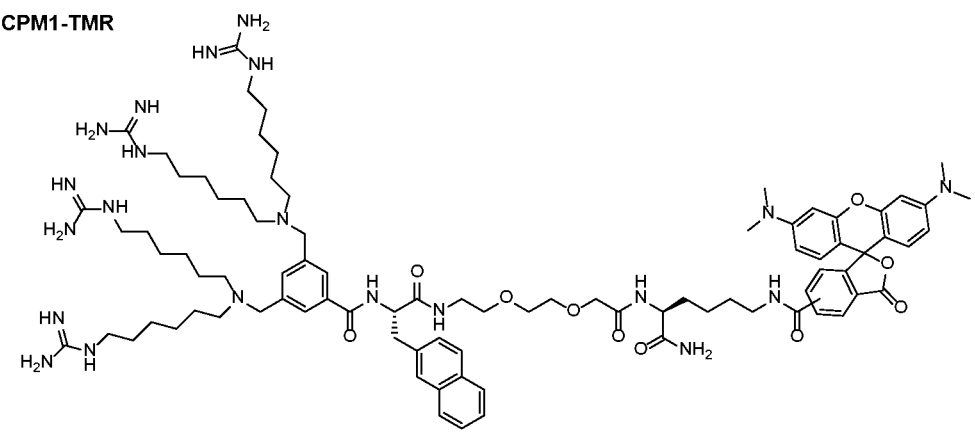
FIG. 4 shows the structures of CPM1$^{TMR}$, CPM2$^{TMR}$, CPM3$^{TMR}$, and the control CPM4$^{TMR}$. CPM2$^{TMR}$ and CPM3$^{TMR}$ each incorporate an additional hydrophobic amino acid. TMR=tetramethylrhodamine, a pH-insensitive dye.
Figure 4:
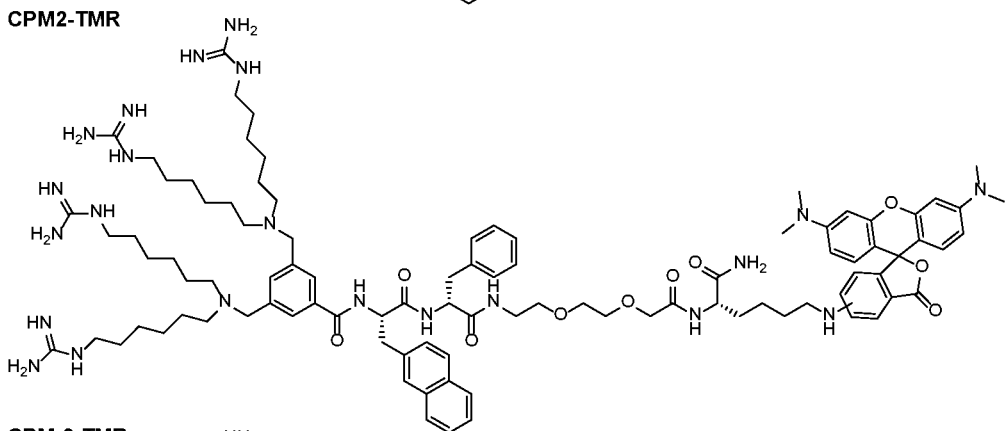
Figure 4:
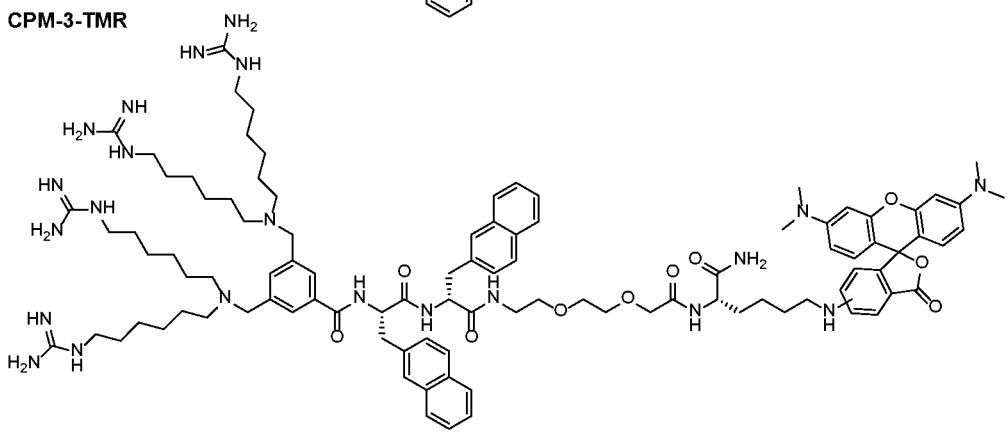
Figure 4:
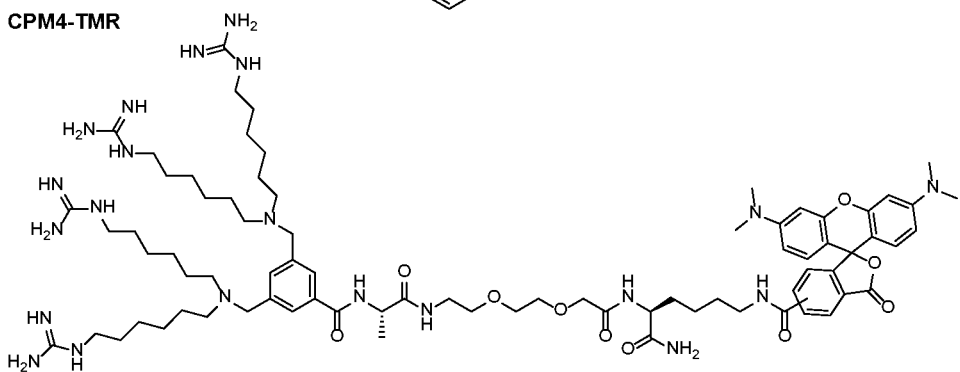

The impact on cytosolic entry efficiency and/or mitochondrial-targeting specificity of adding a second hydrophobic group onto the CPM was evaluated. D-phenylalanine (D-Phe) or D-Nal was added to the CPM1 structure to give CPM2 and CPM3, respectively (Scheme 2). The alternating stereochemical configuration of the two hydrophobic residues can improve the cytosolic entry efficiency of cyclic CPPs, while incorporation of a D-amino acid can improve the proteolytic stability of the CPMs. As a control, CPM4 was also generated, which is structurally similar to CPM1, except that the D-Nal residue was replaced with an alanine (FIG. 4).

Figure 5:
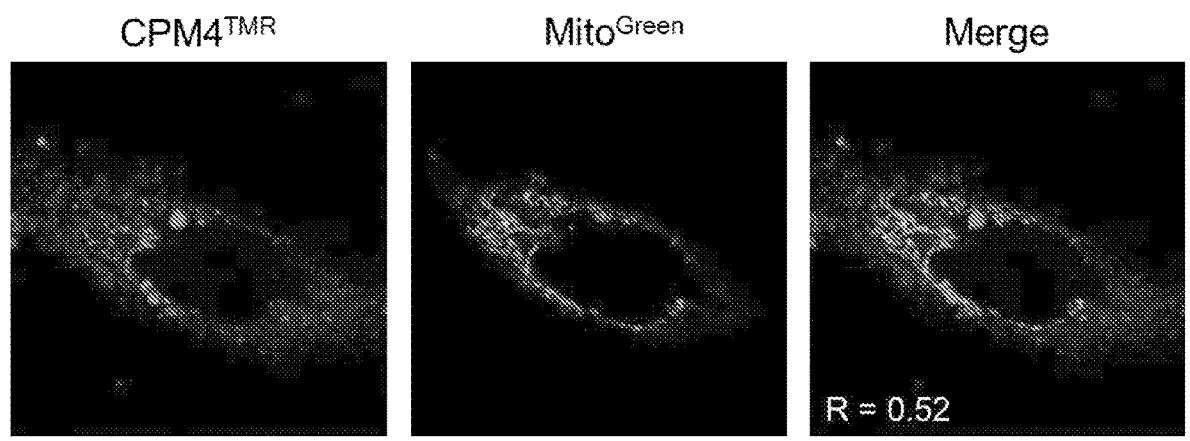
FIG. 5 shows the co-localization of TMR-labeled CPM4 (CPM4$^{TMR}$) and MitoTracker Green in HeLa cells. HeLa cells were treated for 2 h with 2 μM CPM4$^{TMR}$ and then for 15 min with MitoTracker Green before being subjected to live-cell confocal microscopic imaging. A Pearson's coefficient of 0.52 was observed.
Figure 6:
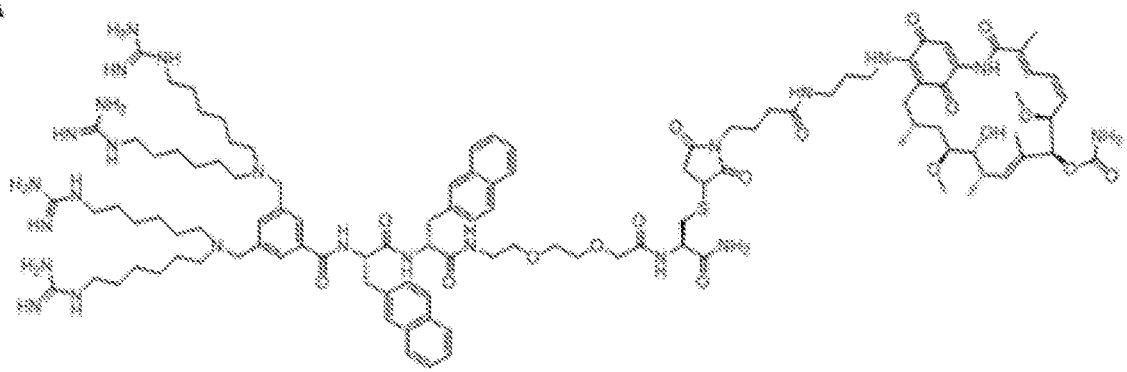
FIG. 6 shows the delivery of small-molecule Hsp90 inhibitor into the mitochondrial matrix of HeLa cells by CPM3 and the apoptosis that results; A) Structure of CPM3-GA. B) Effect of GA, CPM3, and CPM3-GA on HeLa cell viability as measured by the MTT assay. C) Live-cell confocal microscopic images of HeLa cells after 2 h treatment with 2 μM CPM3-GA$^{TMR}$ (red) and 15 min incubation with MitoTracker Green. A merged image is shown on the right with the R value representing Pearson's correlation coefficient for co-localization. D) Apoptosis assay control—untreated HeLa cells stained with annexin V and propidium iodide (PI); E) Apoptosis assay—CPM3-GA treated HeLa cells stained with annexin V and propidium iodide (PI).
Figure 6:
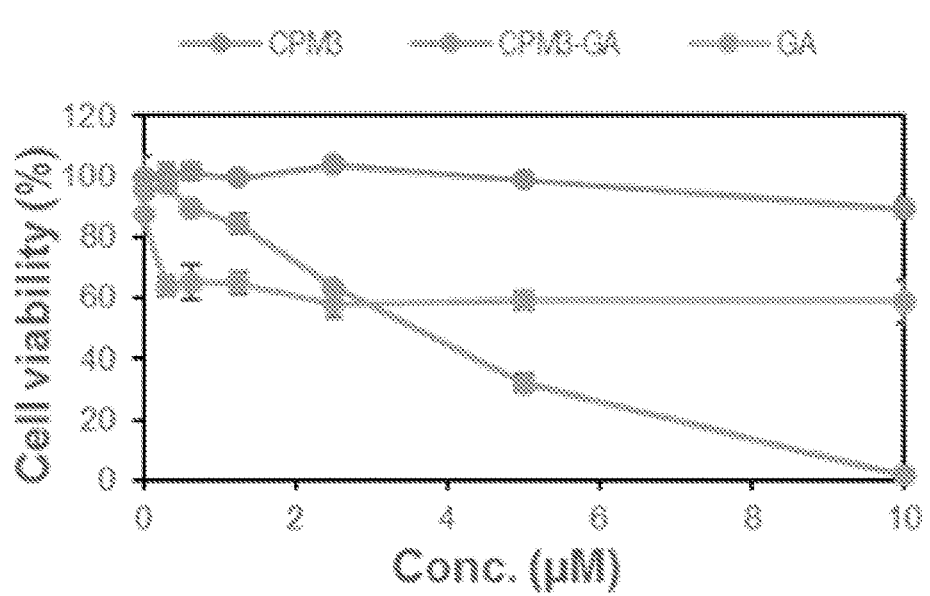
Figure 6:
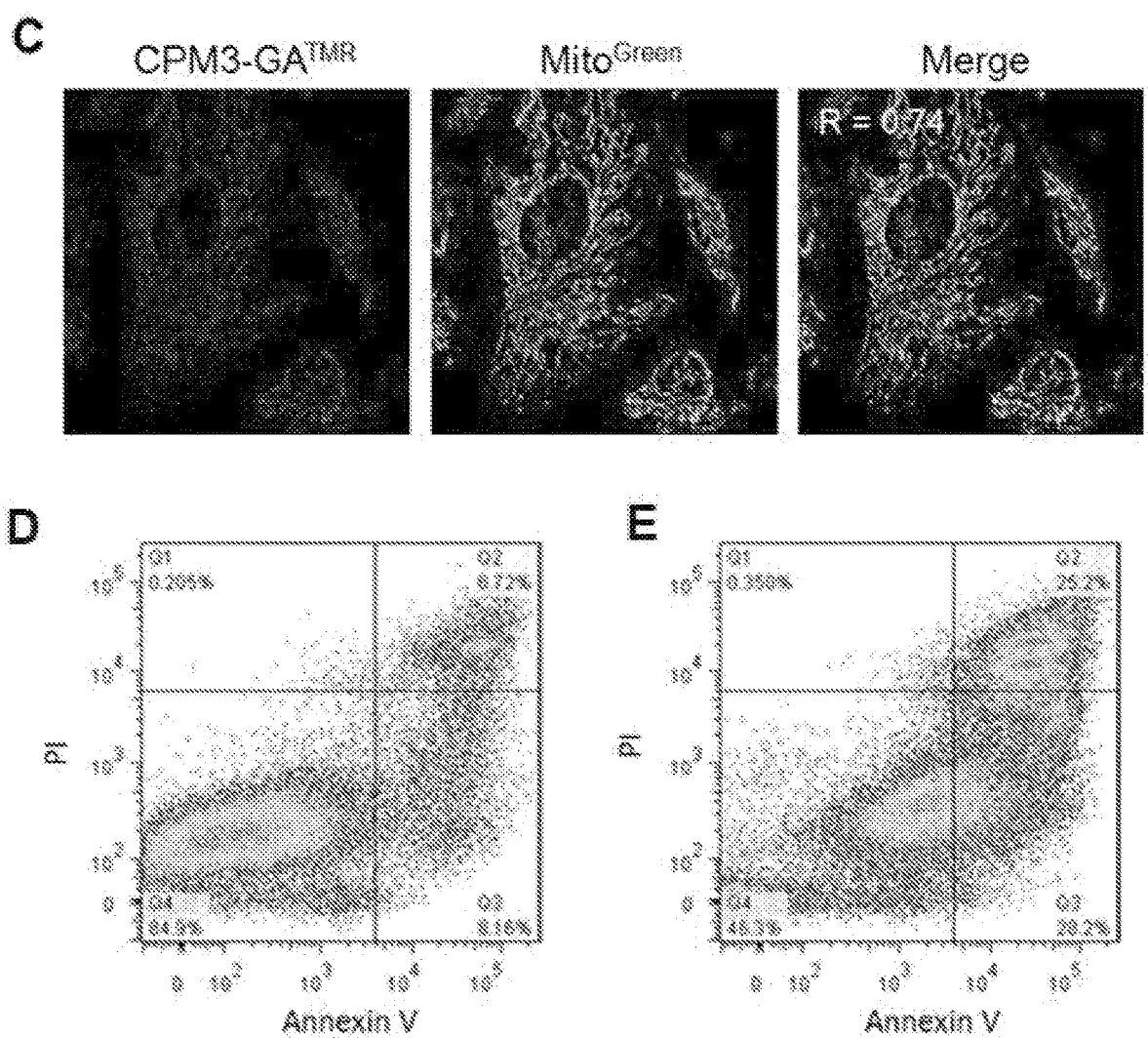

Flow cytometry analysis of HeLa cells treated for 2 h with 2 μM NF-labeled CPM1-4 gave relative MFI values of 179%, 247%, 295%, and 72%, respectively (relative to $CPP9^{NF}$), confirming the important role of hydrophobic moieties for efficient cellular entry (FIG. 1B(i)). Live-cell confocal microscopy of HeLa cells treated with 2 μM $CPM2^{TMR}$ or $CPM3^{TMR}$ and MitoTracker Green revealed excellent overlap between the red and green fluorescence, producing correlation coefficients of 0.73 and 0.89, respectively (FIG. 1B(iii), 1B(iv)). While every MitoTracker Green signal was matched by a corresponding $CPM^{TMR}$ signal, the reverse was not true. A small number of $CPM2^{TMR}$ (and CPM3 TMR) fluorescence spots were not matched by corresponding MitoTracker Green signals. Without being bound by theory, these signals were caused by CPMs still entrapped inside the endosomal/lysosomal compartments. CPM3 appears to be more efficient in endosomal escape than CPM1 and CPM2, resulting in higher cytosolic entry efficiency (FIG. 1a) and greater co-localization with MitoTracker than the latter (FIG. 1B(ii)-(iv)). As the control, CPM4 produced both weaker intracellular fluorescence and poorer overlap with the MitoTracker Green signals (R=0.52; FIG. 1B(i) and FIG. 5). Because of its overall properties (cellular uptake efficiency, mitochondrial-targeting specificity, and good aqueous solubility), CPM3 was selected for further studies.

Delivery of Therapeutic Agents to Mitochondria of Cells

To address whether the CPMs are located inside the mitochondrial matrix or simply bound to the outer (or inner) mitochondrial membrane and test the feasibility of using the CPMs to specifically deliver therapeutic agents into the mitochondrial matrix, a small-molecule inhibitor against molecular chaperon heat shock protein 90 (Hsp90), geldanamycin (GA) was attached to CPM3 (FIG. 6A) and examined its anti-proliferative activity against cancer cells. Hsp90 inhibitors are promising therapeutic agents for cancer treatment, and several Hsp90 inhibitors have transitioned to clinical trials, including GA and its derivatives. A class of GA analogues that inhibit the Hsp90 network in tumor mitochondria has been established. Inhibiting mitochondrial Hsp90 was shown to induce rapid tumor cell apoptosis and complete tumor cell killing.

Anti-cancer activity of Hsp90 inhibitors. HeLa cells ($3 \times 10^3$ cells/well) were seeded in a 96 well plate in 100 μL DMEM with 10% FBS, and 1% penicillin/streptomycin the day before treatment. After overnight attachment, cells were washed once with PBS and then treated with various concentrations of CPM3, CPM3-GA, or GA in full growth medium (DMEM, 10% FBS, 1% penicillin/streptomycin) for 24 h. Cell viability was quantitated by 3-(4,5-dimethylthiazol-2-yl)-2,5-diphenyl tetrazolium bromide (MTT) assay according to manufacturer's protocol.

In this study, the C-terminal lysine of CPM3 was replaced with a cysteine and GA was covalently attached to the cysteine side chain via a maleimide-thiol reaction to produce CPM3-GA (FIG. 6A). The anti-proliferative activity of CPM3-GA, GA alone, or CPM3 alone was assessed by treating HeLa cells with varying concentrations of the inhibitor (0-10 µM) for 24 h followed by viability test using the 3-(4,5-dimethylthiazol-2-yl)-2,5-diphenyltetrazolium bromide (MTT) assay. The results show that GA caused a maximum of ~40% reduction in HeLa cell viability, although the maximal inhibition was reached at a very low inhibitor concentration (0.3 µM; FIG. 6B). In contrast, CPM3-GA reduced the viability of HeLa cells in a dose-dependent manner ($IC_{50}$~4 µM) and caused the complete loss of cell viability at 10 µM concentration, while CPM3 alone showed essentially no cytotoxicity up to 10 µM concentration. (FIG. 6B). Thus, the pharmacologic property of CPM3-GA is consistent with a GA derivative that is specifically delivered into the mitochondrial matrix.

To confirm mitochondrial delivery of GA by CPM3, CMP3-GA was labeled with TMR and examined HeLa cells treated with 2 µM CPM3-GA$^{TMR}$ and MitoTracker Green by live-cell confocal microscopy. CPM3-GA$^{TMR}$ co-localized with MitoTracker Green showing a correlation coefficient of 0.74 (FIG. 6C). These results strongly suggest that CPM3 delivered GA into the mitochondrial matrix.

Mitochondrial Delivery of CPM3-GA Causes Apoptotic Cell Death

Procedure: HeLa cells were cultured in 12-well plates ($1\times10^5$ cells per well) a day before the experiment. The cells were incubated with 20 µM of CPM3-GA in full growth medium (DMEM, 10% FBS, 1% penicillin/streptomycin) and incubated at 37° C. for 48 h. The cells were washed with PBS twice, harvested with 0.25% trypsin, mixed with DMEM containing 10% FBS, and pelleted by centrifuge at 200 g for 5 min. The cell pellets were washed twice with DPBS and resuspended in annexin V/PI for 15 min (according to manufacturer's protocol). Stained cells were analyzed on a BD LSRFortessa flow cytometer.

Figure 7:
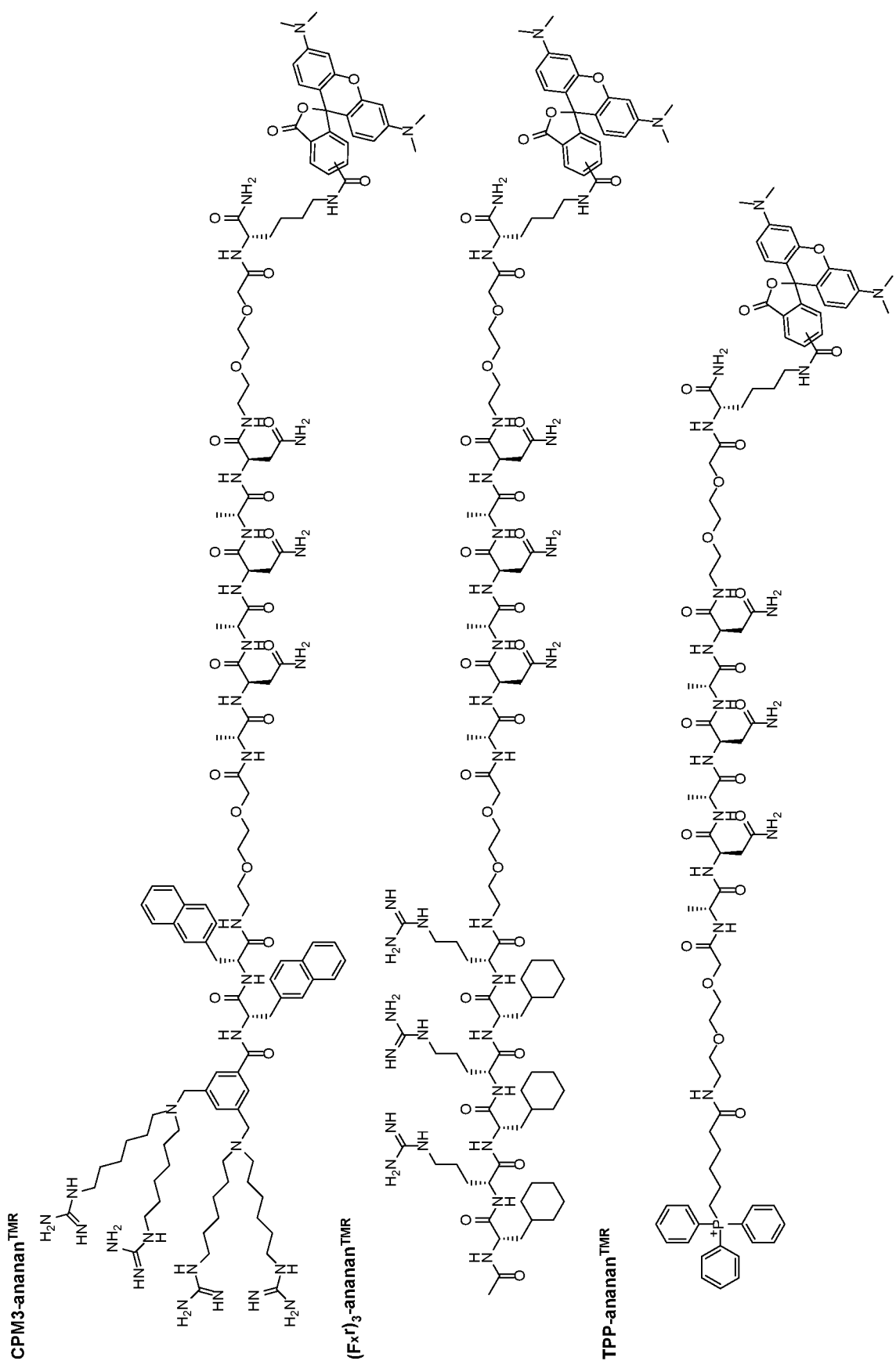
FIG. 7 shows the structure of CPM3-ananan$^{TMR}$ compared to (F$_x$r)$_3$-ananan$^{TMR}$ and TPP-ananan$^{TMR}$. TMR=tetramethylrhodamine, a pH-insensitive dye; a=alanine and n=asparagine; F$_x$=cyclohexylalanine and r=D-arginine; TPP=triphenylphosphonium.
Figure 8:
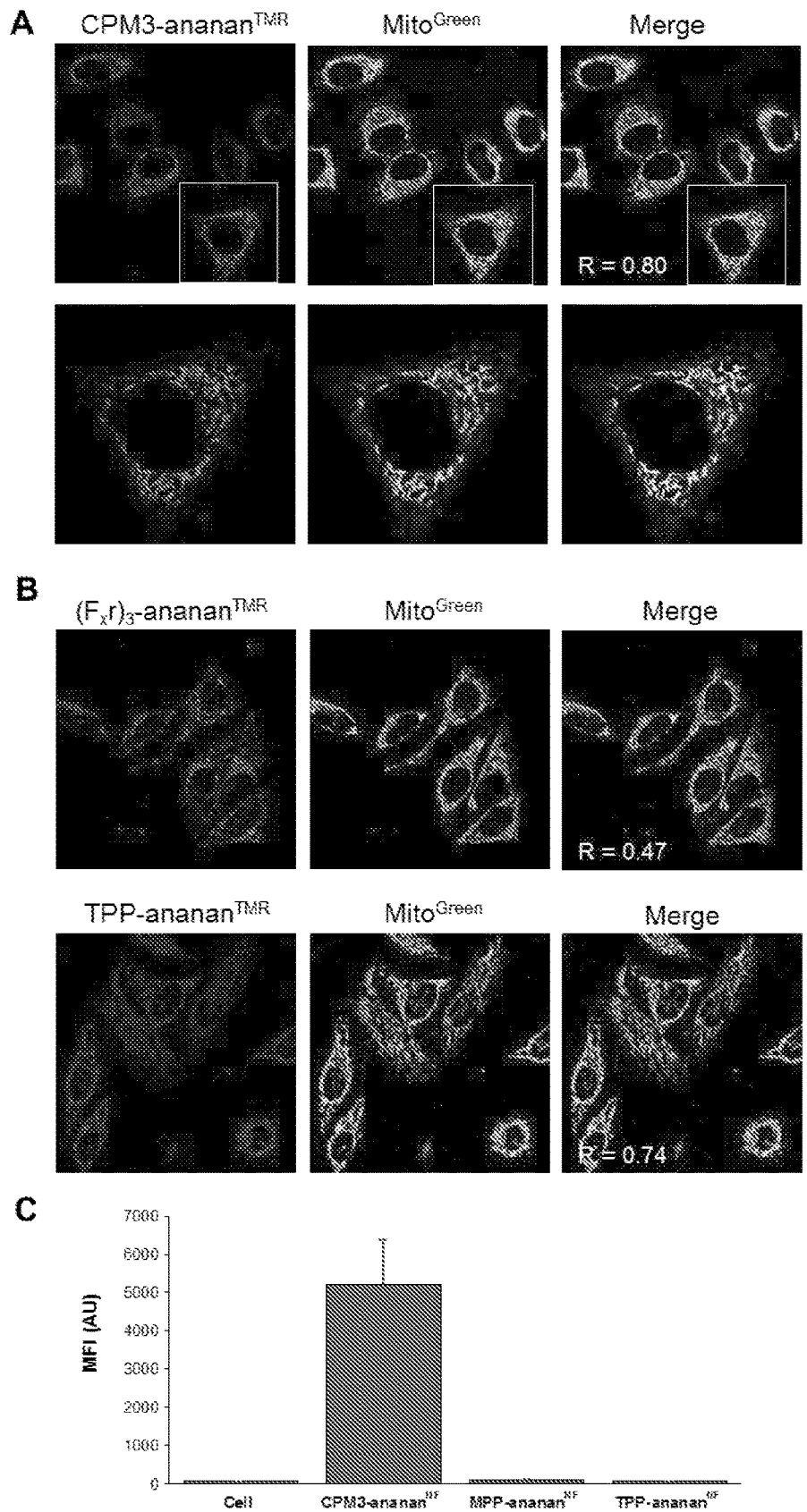
FIG. 8 shows a comparison of CPM3, (F$_x$r)$_3$ and TPP for their ability to deliver peptidyl cargoes into the mitochondria; A) Live-cell confocal microscopic images of HeLa cells after 2 h treatment with 2 µM CPM3-ananan$^{TMR}$ (red) and 15 min incubation with MitoTracker Green. Boxed regions are magnified in the lower panels to show colocalization; B) Live-cell confocal microscopic images of HeLa cells after 2-h treatment with 2 µM (F$_x$r) 3-ananan$^{TMR}$ or TPP-ananan$^{TMR}$ (red) and 15 min incubation with MitoTracker Green; C) Cytosolic entry efficiency of CPM3-ananan$^{NF}$, MPP-ananan$^{NF}$, and TPP-ananan$^{NF}$ as determined by flow cytometry analysis of HeLa cells after 2-h treatment with 5 µM NF-labeled peptides. Data reported are the mean±SD of three independent experiments. TMR=tetramethylrhodamine, a pH-insensitive dye; a=alanine and n=asparagine; F$_x$=cyclohexylalanine and r=D-arginine; TPP=triphenylphosphonium; MPP=mitochondrial-penetrating peptides.

Results: Annexin V and propidium iodide staining of treated HeLa cells showed that the treated cells died via apoptosis (FIG. 6E). Inhibition of mitochondria Hsp90 by CPM3-GA causes apoptotic cell death. This is in contrast to what is observed from the flow cytometry data for untreated HeLa cells (FIG. 6D). Q1 shows the necrotic cells; Q2 shows the late-apoptotic or necrotic cells; Q3 shows the early apoptotic cells; and Q4 shows the viable cells Delivery of Cell-Impermeable Cargoes in the Mitochondrial Matrix To test whether the CPMs are capable of delivering otherwise impermeable cargoes into the mitochondrial matrix, CPM3 was appended to the N-terminus of a D-peptide cargo, ala-asn-ala-asn-ala-asn-miniPEG-Lys, and labeled the adduct with TMR at the C-terminal lysine side chain (FIG. 7). The choice of a D-peptide was to minimize any proteolytic degradation during cellular assays, which can complicate the data interpretation. For comparison, the D-peptide containing an N-terminal TPP or Kelley's MPP, $(F_xr)_3$ (where $F_x$ is cyclohexylalanine and r is D-arginine; FIG. 7) were also synthesized, which are known mitochondrion-targeting agents. HeLa cells were treated with the peptides (2 µM) for 2 h and examined by live-cell confocal microscopy. The CPM3-conjugated peptide (CPM3-ananan$^{TMR}$) produced punctate fluorescence which overlapped well with that of MitoTracker Green, with a correlation coefficient of 0.80 (FIG. 8A). Without being bound to theory, again, a small amount of the peptide was believed to be still inside the endosomal/lysosomal compartments at the time of experiment, causing the correlation coefficient to be <1. This data demonstrates that the CPMs are capable of efficiently and specifically delivering peptidyl cargoes into the mitochondria. In contrast, the MPP-conjugated peptide, $(F_xr)_3$-ananan$^{TMR}$, entered the cell with low efficiency, was largely entrapped inside the endosomes/lysosomes, and had poor co-localization with MitoTracker Green (correlation coefficient=0.47; FIG. 8B). The TPP-conjugated D-peptide (TPP-ananan$^{TMR}$) produced very weak intracellular fluorescence which overlapped with that of MitoTracker Green (correlation coefficient=0.74). Finally, all three peptides were labeled with NF and their cytosolic entry efficiencies were assessed by flow cytometry. CPM3-ananan$^{NF}$ entered the cytosol of HeLa cells with much greater efficiency than MPP-ananan$^{NF}$, TPP-ananan$^{NF}$, and Tat-ananan$^{NF}$ (FIG. 8C).

The sub-mitochondrial localization of the CPMs was also evaluated by high-resolution 3D-SIM imaging of HeLa cells treated with CPM3-ananan$^{TMR}$ (see FIG. 7 for chemical structure) and transfected with the mitochondrial marker Grx2-mito-roGFP. Grx2-mito-roGFP produces a green fluorescent protein (GFP) inside the mitochondrial matrix.

Procedure: Cell preparation for structured illumination microscopy imaging. HeLa cells ($4\times10^4$ cells) were seeded in poly-D-lysine coated and clean cover glasses (25 mm diameter) mounted on Attofluor™ Cell Chamber (Invitrogen™) and cultured for 24 h. Cells were then transfected with 1 µg of DNA (pGrx2-mito-roGFP) using Lipofectamine 2000 CD reagent (Thermo Fisher) according to the manufacturer's instructions. 48 h post-transfection, HeLa cells were treated with CPM3-ananan$^{TMR}$ at a final concentration of 2 µM in DMEM supplemented with 1% FBS and 1% penicillin/streptomycin for 2 h at 37° C. in the presence of 5% $CO_2$. Fifteen min prior to imaging, cells were washed once with PBS and then treated with 5 µg/ml Hoechst 33342 dye. Immediately before imaging, cells were washed twice with PBS and kept in imaging media.

Structured illumination microscopy: Super-resolution images were acquired using a Nikon Ti-E super-resolution microscope (Nikon Instruments Inc., NY) in 3D structured illumination microscopy (SIM) mode. The light sources were 488 nm and 561 nm laser for GFP and TMR-labelled probes, respectively. Cells were imaged with a 100×, oil-based objective (Nikon Apo TIRF 100×/1.49 (Nikon Instruments Inc., NY, USA). The imaging experiments were performed at 37° C. with 5% $CO_2$ for 30 min. Fifteen images of several µm thickness were acquired with a CCD detector (Model iXon Ultra 897, Andor, Belfast, UK) with 0.125-µm z-steps. Image stacks were reconstructed in NIS-Elements Advanced Research (Nikon Instruments Inc., NY). Image processing was performed using ImageJ software[j] and scale bars were added using the FigureJ plugin of the ImageJ software6. Images were further processed and annotated in Adobe Photoshop CS4.

Figure 9:
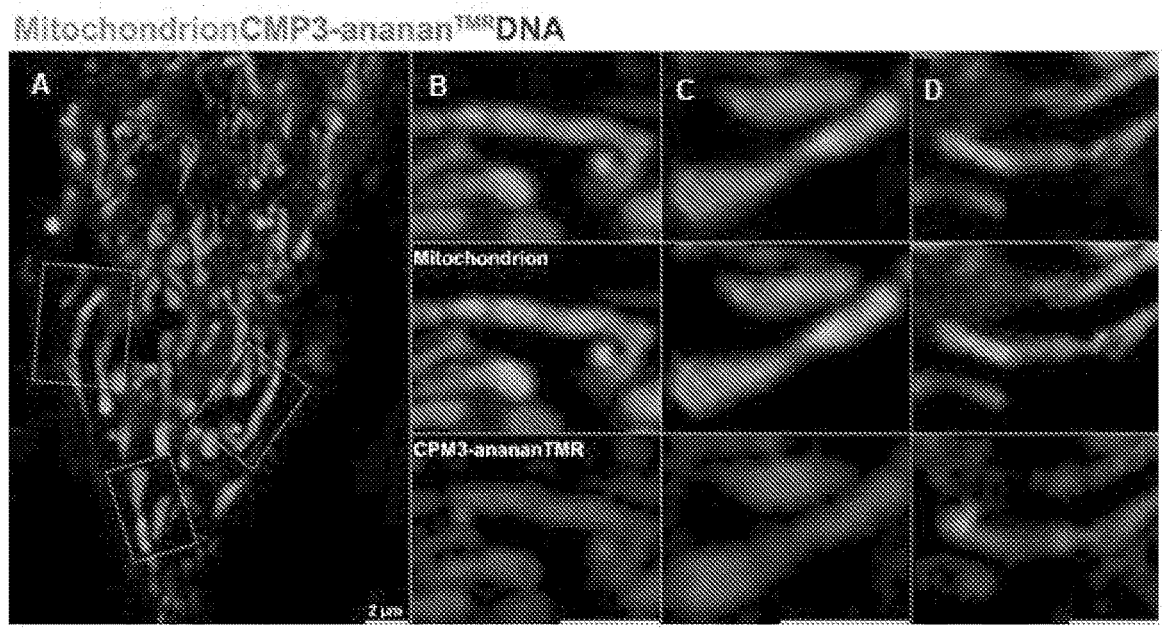
FIG. 9 shows high-resolution fluorescence images showing the mitochondrial distribution of CPM3-ananan$^{TMR}$; A) 3D-SIM reconstructed image of HeLa cells 48 h post-transfection with pGrx2-mito-roGFP (green) and treated with 2 µM CPM3-ananan$^{TMR}$ (red) for 2 h and 5 µg/ml Hoechst 33342 dye (blue) for 15 min prior to imaging. (B-D) Zoom-in images of the boxed areas from (A) showing detailed mitochondrial structures. Top panel, zoom-in images of the boxed areas in (A); middle panel, localization of the mitochondrion marker (gray) within the stroma; and bottom panel, localization of CPM3-ananan$^{TMR}$ (gray) at both the periphery (which corresponds to the mitochondrial membrane) and the interior of mitochondria (which correspond to the cristae). Scale bars: 2 µm.

Results: CPM3-ananan$^{TMR}$ appeared to be highly distributed throughout the mitochondrial network (FIG. 9A). The zoomed insets (FIGS. 9B-9D) showed highly similar fluorescence patterns for CPM3-ananan$^{TMR}$ and mitochondrial GFP. Inner lamellar membrane accumulation is observed with dark regions and internal thin fluorescent gaps, corresponding to the structure of mitochondrial cristae (FIGS. 9B-9D; bottom panels). Treatment of HEK293 cells with CPM3-ananan$^{TMR}$ and Grx2-mito-roGFP exhibited similar mitochondrial fluorescence patterns (data not shown). Similar mitochondrial structures were also previously observed where different mitochondrion probes and markers were analyzed by SD-SIM imaging. These data demonstrate that CPM3-ananan$^{TMR}$ is efficiently delivered into the mitochondrial matrix.

Example 3

Evaluation of Stability of CPMs in Serum

Figure 10:
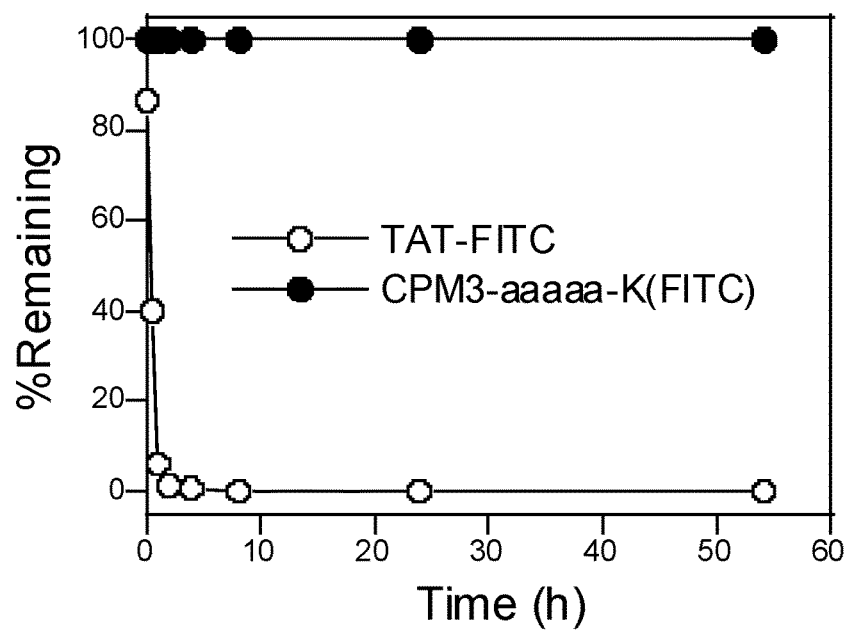
FIG. 10 shows a graph comparing the serum stability of CPM3 and TAT-FITC.

CPM3 covalently conjugated to a penta(D-alanine)-Lys (FITC) cargo (CPM3-aaaaa-Lys(FITC), 100 µM) was incubated in 25% human serum at 37° C. Aliquots were withdrawn at indicated time points, quenched by the addition of trichloroacetic acid, and analyzed by reversed-phase HPLC equipped with an analytical $C_{18}$ column. CPM3-aaaaa-Lys (FITC) showed no detectable degradation after 54 h, whereas Tat-FITC was completely degraded within 2 h (FIG. 10). Tat=Ac-YGRKKRRQRRR

Example 4

Evaluation of CPM Cytotoxicity

Procedure: Mitochondria membrane potential assay. Experiments were carried out by using JC-10 Mitochondrial Membrane Potential Assay kit (Abcam, ab112134) according to the manufacturer's manual. Briefly, HeLa cells ($2 \times 10^4$ cells/well) were seeded in a 96-well plate (black wall clear bottom) in 90 µL of DMEM containing 10% FBS and 1% penicillin/streptomycin and allowed to attach overnight. Ten µL of a 10× stock solution of test compounds were added to the cells to give the desired final concentration and the cells were incubated for 24 h. Without washing, cells were treated with 50 µL of a JC-10 dye solution (30 µM in buffer A) for 60 min. Fifty µL of buffer B was added and the fluorescence intensities at $E_x/E_m$=490/520 nm and 540/590 nm were recorded on a microplate reader (Infinite M1000Pro).

Figure 11:
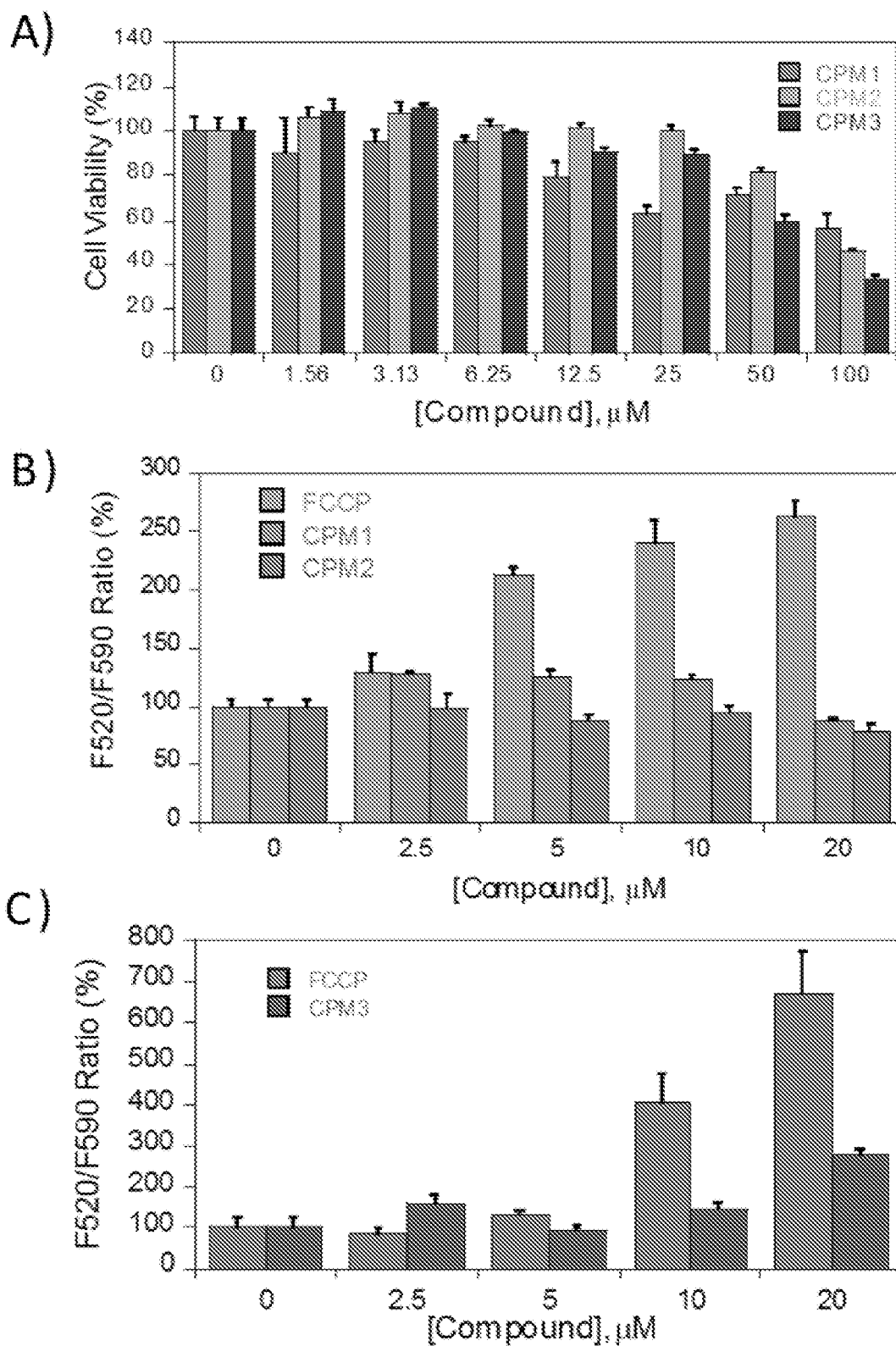
FIG. 11 shows a series of graphs measuring the cytotoxicity of CPMs; A) Effect of CPM1-3 on the viability of HeLa cells as monitored by the MTT assay. (B,C) Effect of CPM1-3 and FCCP on the mitochondrial membrane potential in HeLa cells. All values are relative to that of the untreated control (100%). The Data reported are the mean±SD of at least three independent experiments (n=3-10.

Results: In MTT assays, up to 10 µM CPMs did not significantly affect the viability/proliferation of HeLa cells (FIG. 11A). At 100 µM, CPM1-3 (FIG. 1A) reduced the viability of HeLa cells by 40-60%. CPM1-3 was next tested for a potential effect on mitochondrial membrane potential, a key indicator of cell health or injury. HeLa cells untreated or treated with CPM were labeled with JC-10, a dye molecule which emits green fluorescence inside the cytosol but red fluorescence inside the mitochondria. The ratio of green/red fluorescence (F520/F590) provides an indicator of the mitochondrial membrane potential. Treatment of HeLa cells with a known mitochondrial membrane depolarizer, p-trifluoromethoxy carbonyl cyanide phenyl hydrazone (FCCP), caused retention of JC-10 in the cytosol and dose-dependent increase of the F520/F590 ratio, to up to 7-fold above the normal value at 20 µM FCCP concentration (FIGS. 11B and 11C). On the other hand, CPM1-3 did not perturb the membrane potential at ≤10 µM concentration. At 20 µM, only CPM3 caused a small (2.5-fold) increase in the F520/F590 ratio. These results indicate that the CPMs are relatively nontoxic to mammalian cells.

What is claimed is:

1. A compound having a structure according to Formula I or II

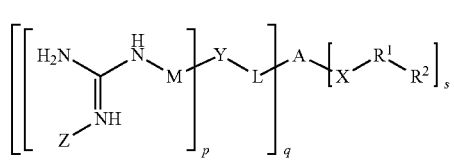
(I)

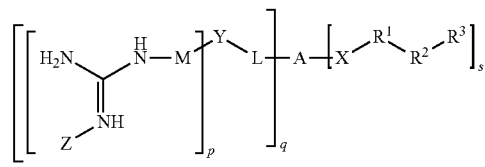
(II)

or pharmaceutically acceptable salt thereof,
wherein:
A is a non-peptidic multivalent moiety, wherein A is selected from the group consisting of:
 (a) a carbocyclyl;
 (b) a heterocyclyl;
 (c) an aryl;
 (d) a heteroaryl; and
 (e) a sugar alcohol;
each L is independently a bond, or an alkylene, alkenylene, alkynylene, carbocyclyl, heterocyclyl, or —$R^c$—$X^1$—$R^d$—, wherein $R^c$ and $R^d$ are independently selected from alkylene, alkenylene, alkynylene, carbocyclyl, or heterocarbocyclyl, each of which are optionally substituted, and $X^1$ is O, NH, or S;
each M is independently a bond, or an alkylene, alkenylene, alkynylene, carbocyclyl, heterocyclyl, or —$R^e$—$X^2$—$R^f$—, wherein $R^e$ and $R^f$ are independently selected from alkylene, alkenylene, alkynylene, carbocyclyl, or heterocarbocyclyl, each of which are optionally substituted, and $X^2$ is O, NH, or S;
each X is independently a first bonding group that links $R^1$ to A, wherein X is a divalent group;
each Y is a second bonding group that directly or indirectly links A to a guanidine group, wherein the guanidine group refers to the structure:

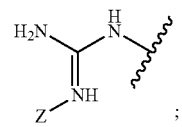

each Z is a lone pair;
each $R^1$ is independently a hydrophobic amino acid residue, or analog thereof, having an aromatic side chain;
each $R^2$ is independently absent or a moiety comprising hydrophobic residue;
each $R^3$ is independently a cargo moiety;
each p is independently 1 to 3;
each q is independently 2 to 7; and
each s is independently an integer from 1 to 3.
2. The compound of claim 1, wherein A is an aryl.
3. The compound of claim 1, wherein A is:

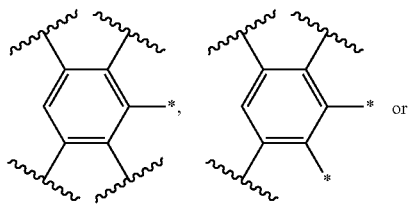

-continued

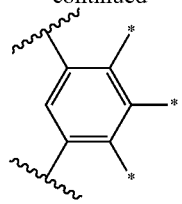

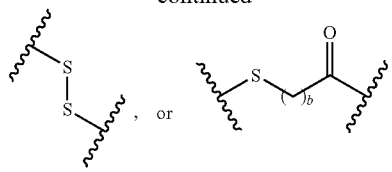

wherein:
each wavy line denotes the point of attachment to L and each asterisk denotes the point of attachment to X.

4. The compound of claim 1, wherein X is a bonding group selected from,

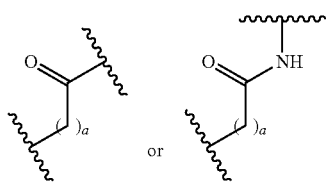

wherein each a is independently number from 0 to 10.

5. The compound of claim 1, wherein Y is selected from N, S,

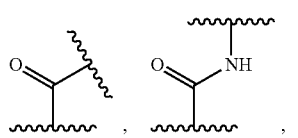

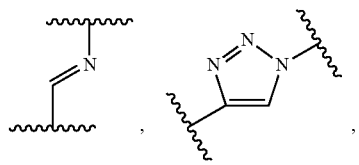

wherein each b is independently a number from 0 to 10.

6. The compound of claim 1, wherein $R^2$ is independently selected from the group consisting of:

(a) a moiety comprising an aryl or heteroaryl moiety and
(b) an amino acid residue or analog thereof, having an aromatic side chain.

7. The compound of claim 1, wherein $R^1$ and $R^2$ are each independently an amino acid selected from the group consisting of phenylalanine, tryptophan, naphthylalanine, phenylglycine, homophenylalanine, tyrosine, cyclohexylglycine, piperidine-2-carboxylic acid, cyclohexylalanine, 3-(3-benzothienyl)-alanine, 3-(2-quinolyl)-alanine, O-benzylserine, 3-(4-(benzyloxy)phenyl)-alanine, S-(4-methylbenzyl) cysteine, N-(naphthalen-2-yl) glutamine, and 3-(1,1'-biphenyl-4-yl)-alanine, each of which is optionally substituted with one or more substituents.

8. The compound of claim 1, wherein p is 2 or 3.

9. The compound of claim 1, wherein Y is N and p is 2.

10. The compound of claim 1, wherein q is 2 or 3.

11. The compound of claim 1, wherein s is 1.

12. The compound of claim 1, wherein the cargo moiety comprises a therapeutic agent.

13. The compound of claim 12, wherein the therapeutic agent is an anticancer agent.

14. The compound of claim 1, wherein the compound is a compound of the formula:

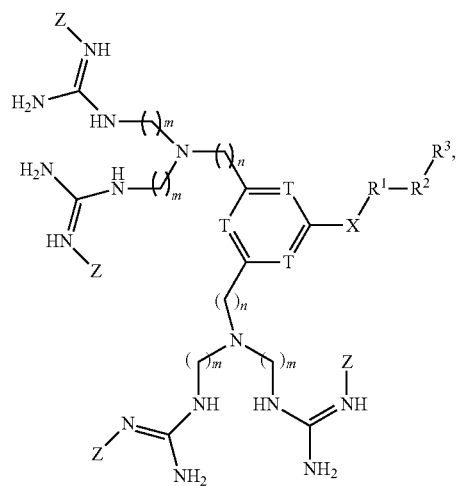

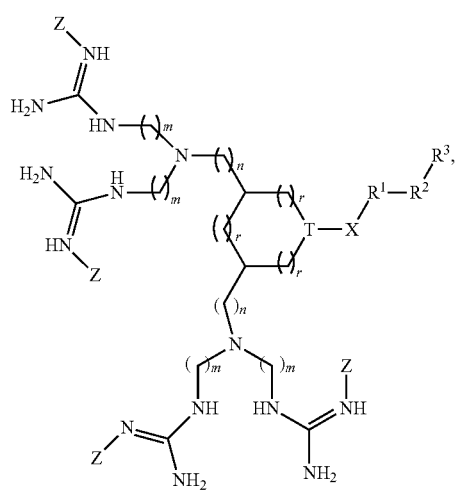

IV

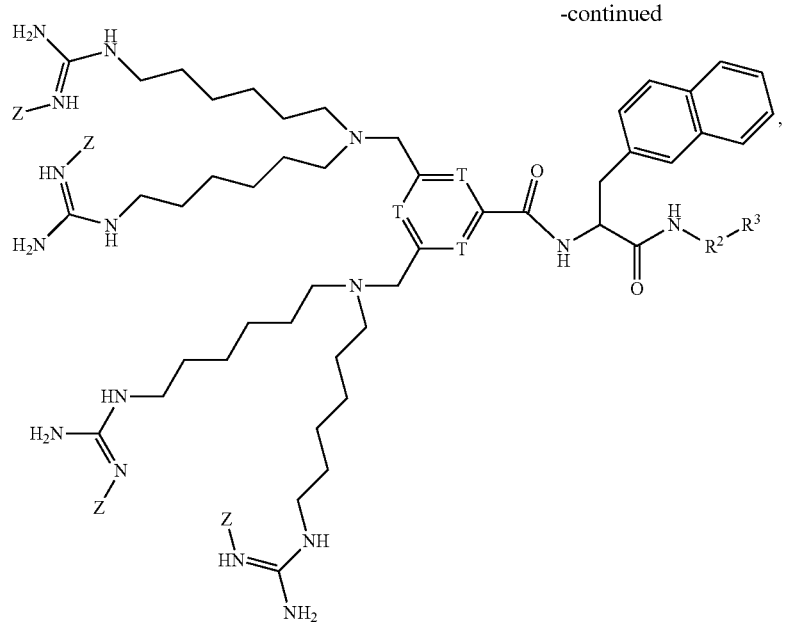
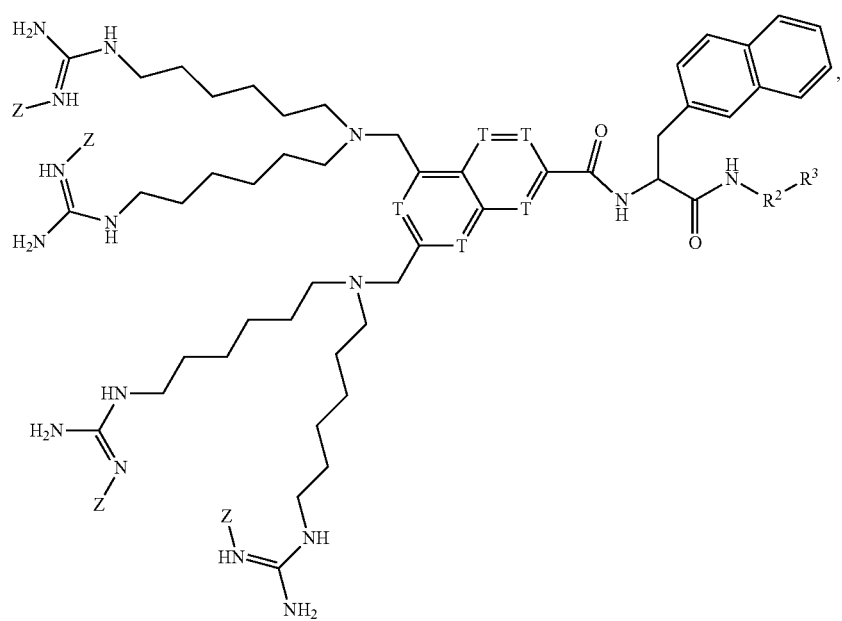

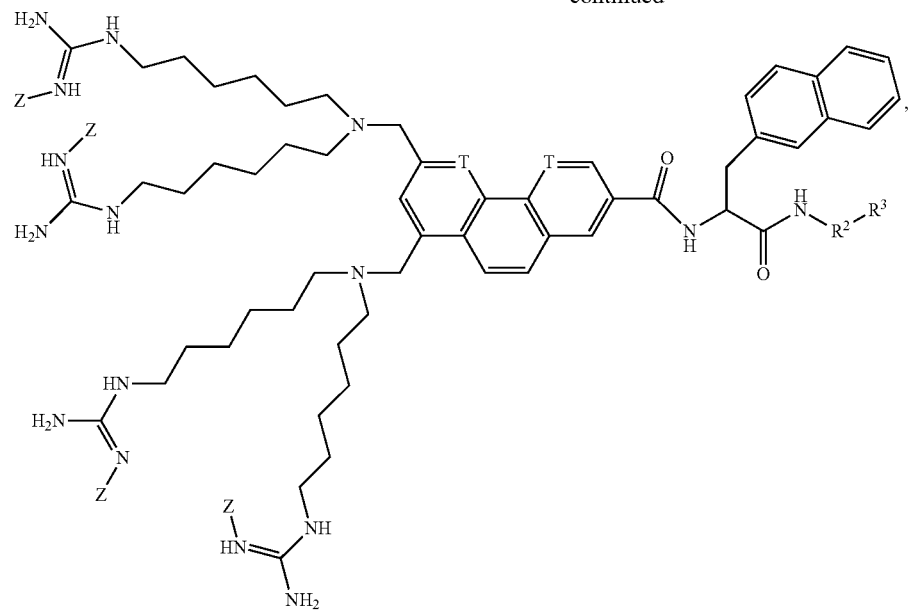
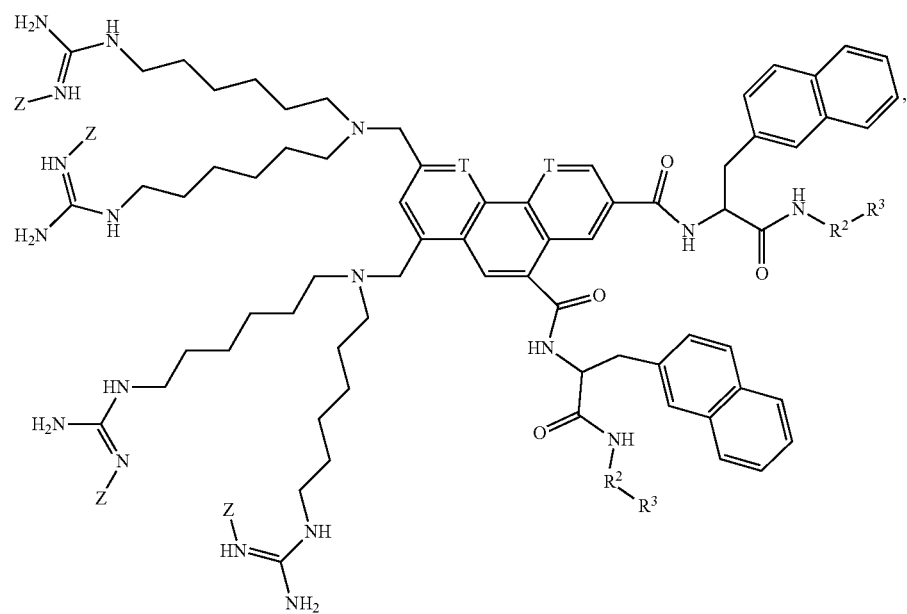

-continued
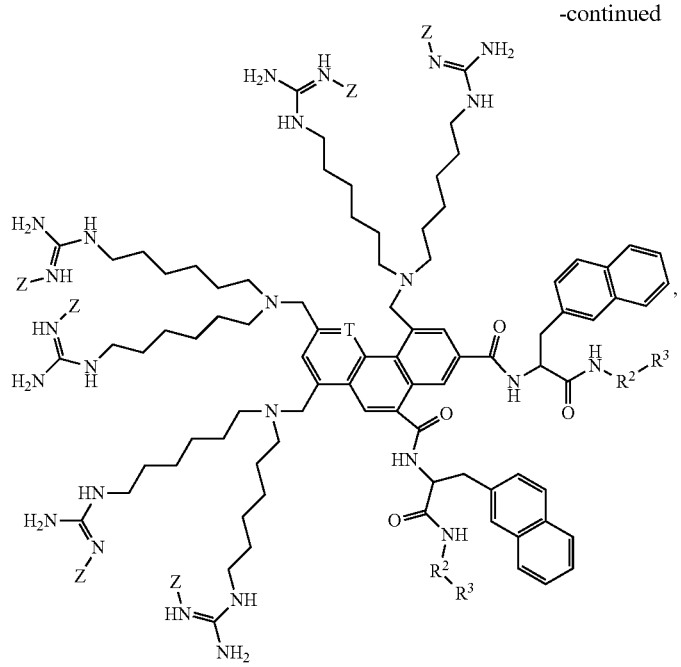
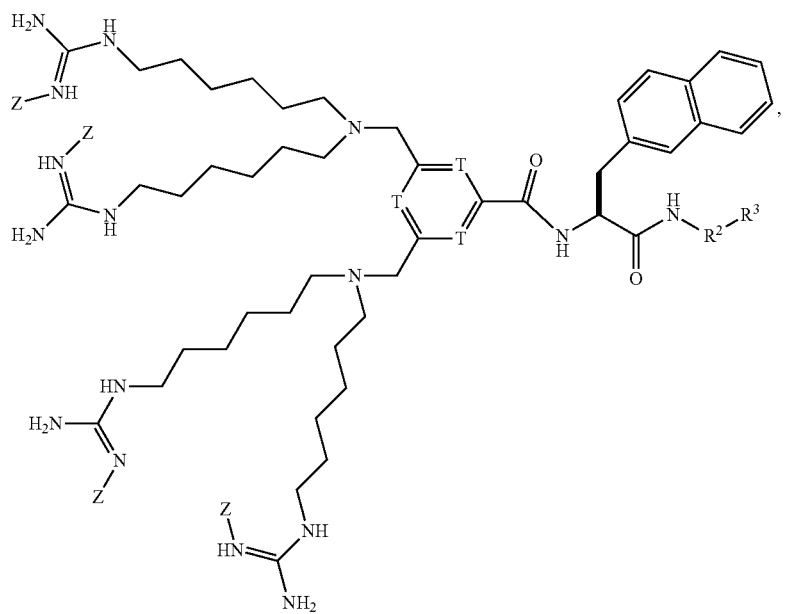

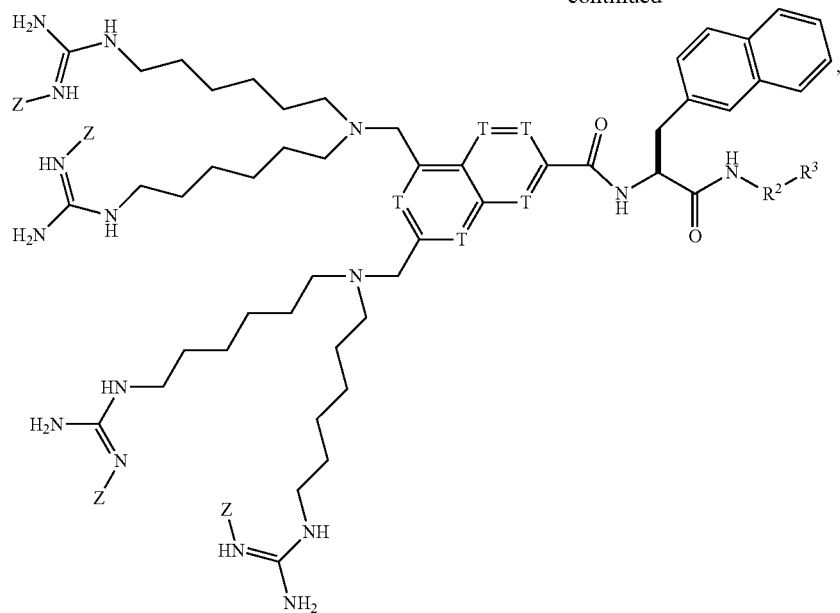
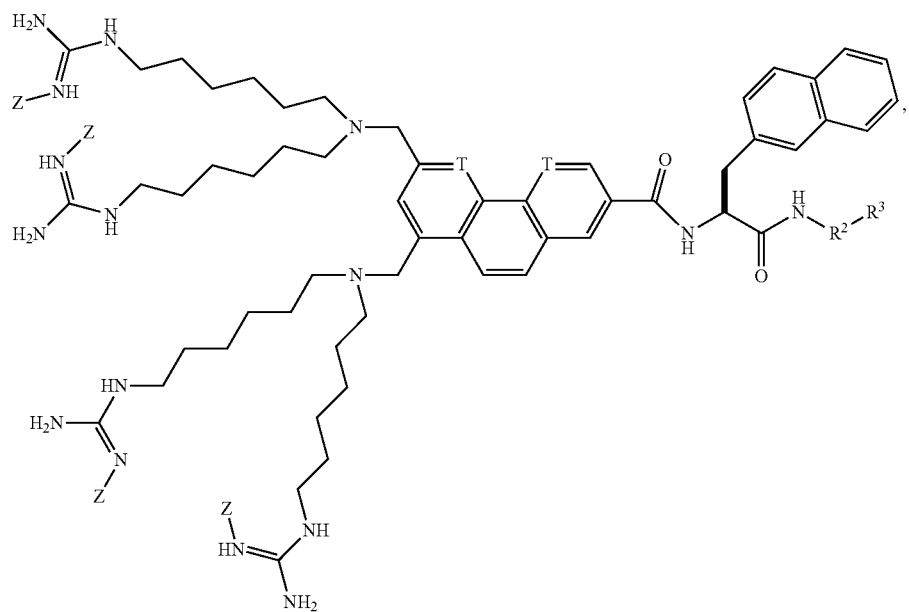

91
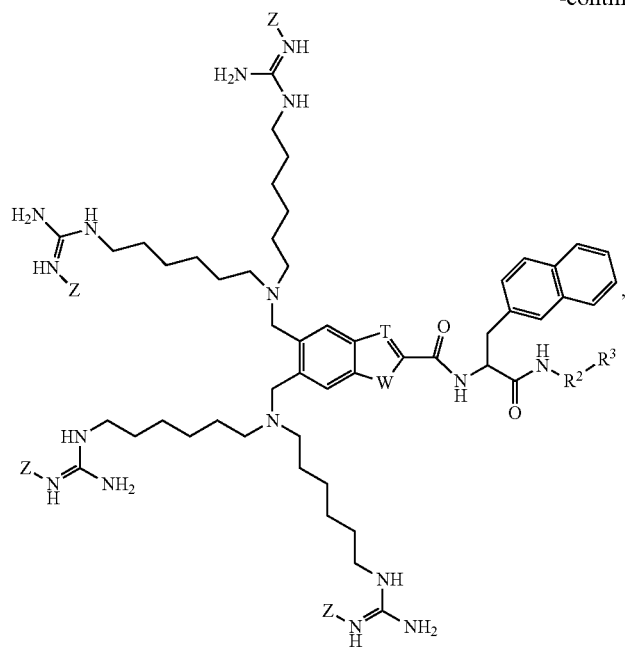
92
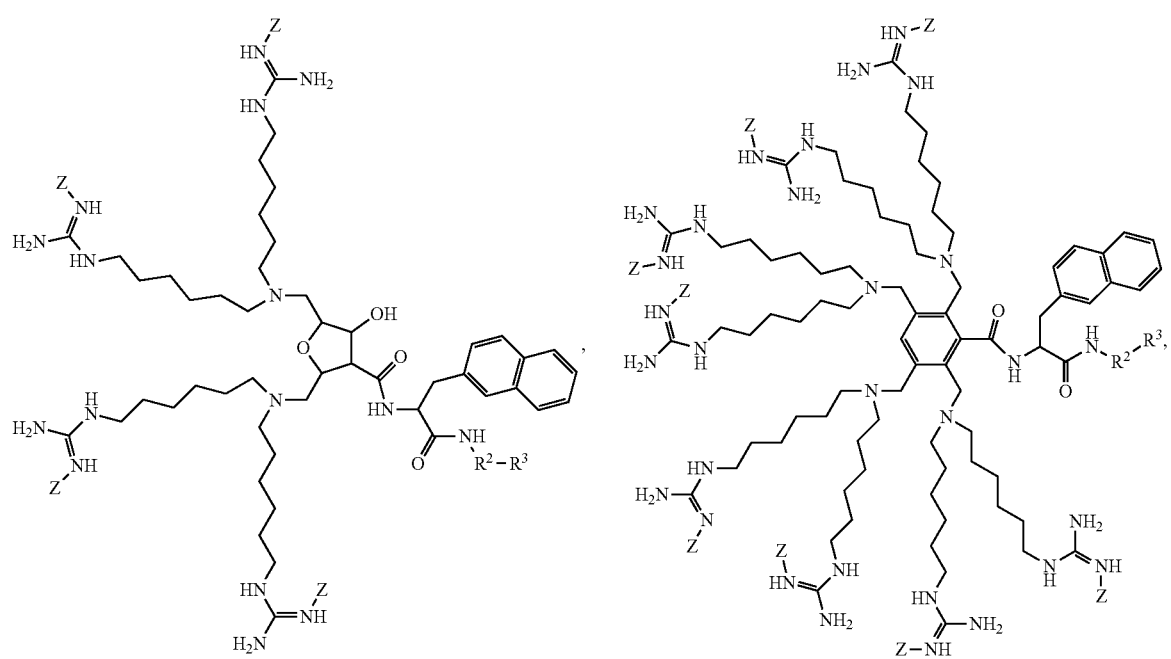

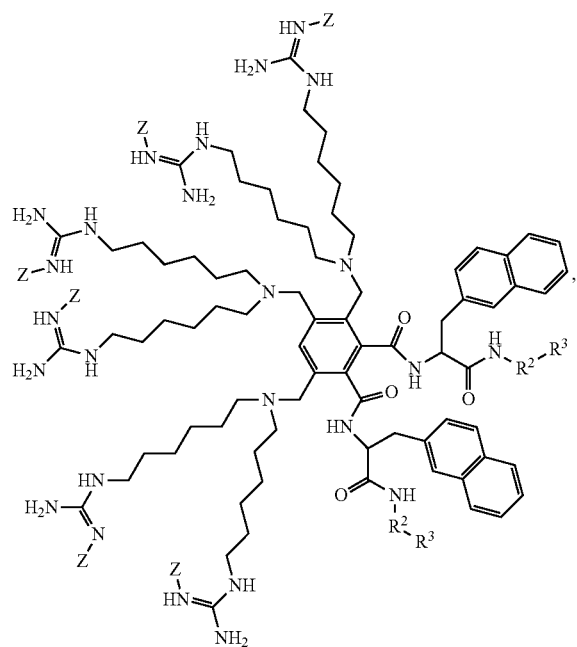
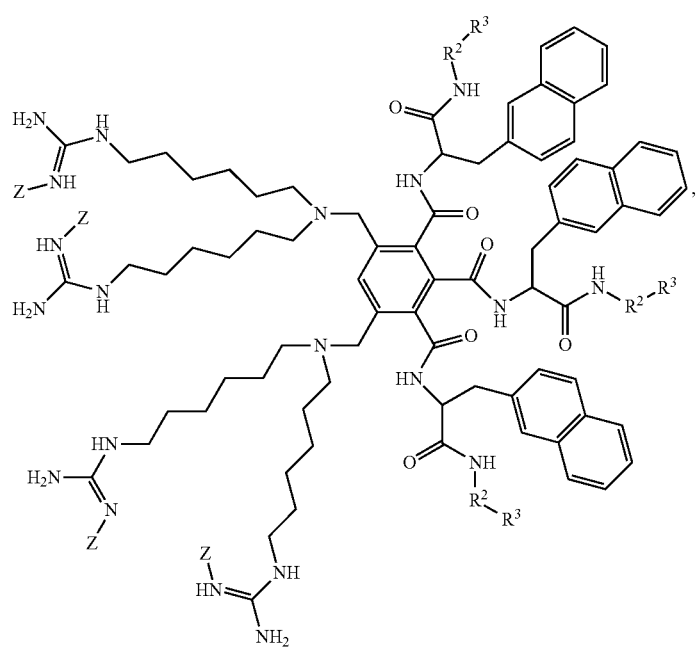

-continued
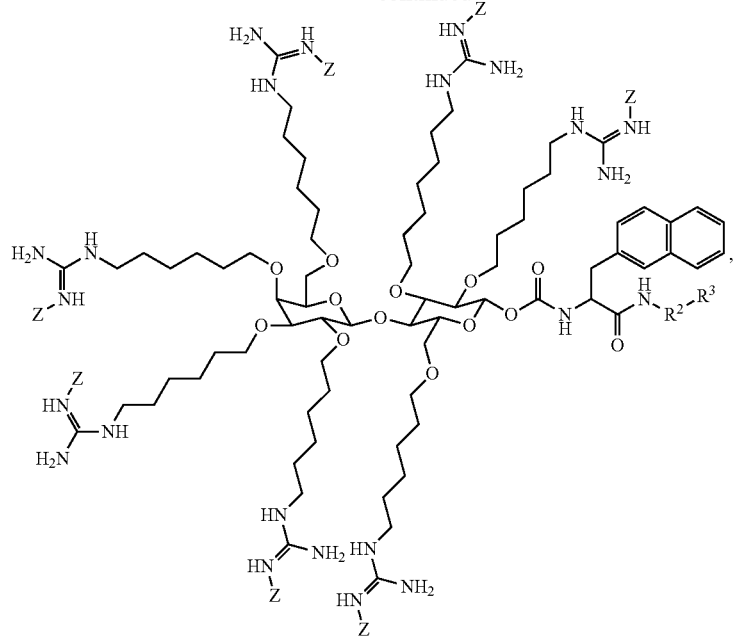
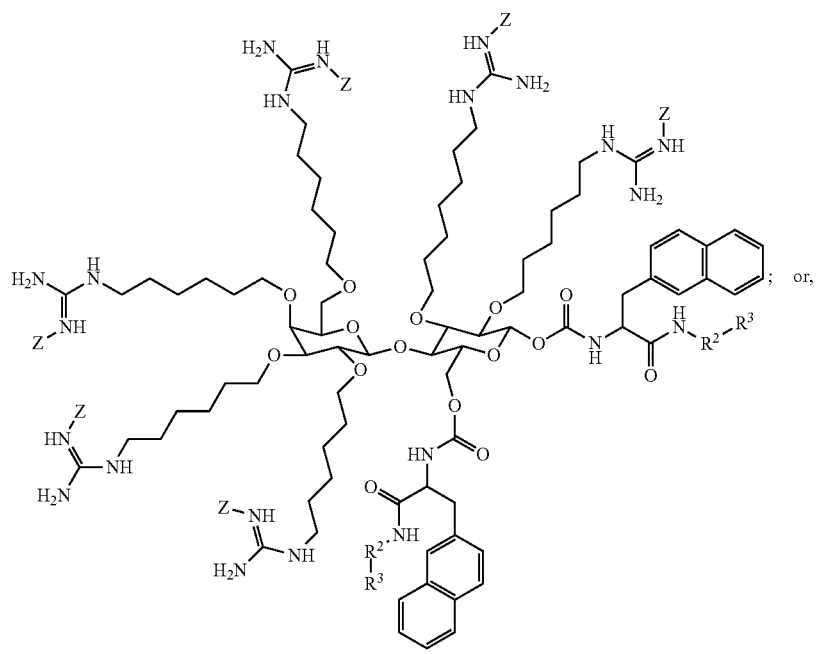

-continued
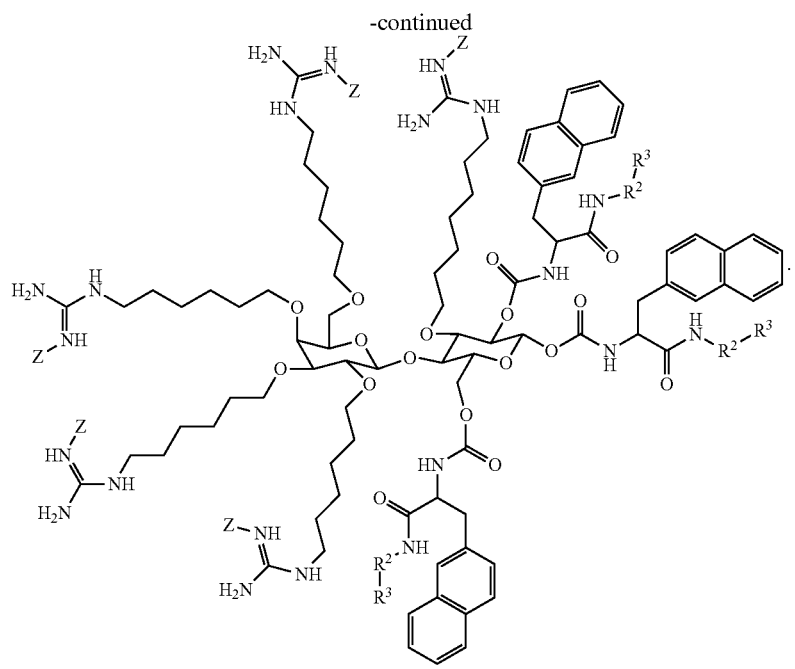
15. The compound of claim 1, wherein $R^1$ is a D-amino acid residue.
16. A pharmaceutical composition comprising a compound of claim 1.
* * * * *